(12) United States Patent
Landthaler et al.

(10) Patent No.: US 10,731,163 B2
(45) Date of Patent: Aug. 4, 2020

(54) OLIGONUCLEOTIDE TARGETED TO THE A20-3' UNTRANSLATED REGION

(71) Applicant: Max-Delbrück-Centrum für Molekulare Medizin in der Helmholtz-Gemeinschaft, Berlin (DE)

(72) Inventors: Markus Landthaler, Berlin (DE); Yasuhiro Murakawa, Berlin (DE)

(73) Assignee: Max-Delbrück-Centrum für Molekulare Medizin in der Helmholtz-Gemeinschaft, Berlin (DE)

( * ) Notice: Subject to any disclaimer, the term of this patent is extended or adjusted under 35 U.S.C. 154(b) by 0 days.

(21) Appl. No.: 15/508,424

(22) PCT Filed: Sep. 2, 2015

(86) PCT No.: PCT/EP2015/070014
§ 371 (c)(1),
(2) Date: Mar. 2, 2017

(87) PCT Pub. No.: WO2016/034611
PCT Pub. Date: Mar. 10, 2016

(65) Prior Publication Data
US 2017/0298359 A1      Oct. 19, 2017

(30) Foreign Application Priority Data
Sep. 2, 2014   (EP) .................................... 14183220

(51) Int. Cl.
*C12N 15/113* (2010.01)
*C12Q 1/6897* (2018.01)

(52) U.S. Cl.
CPC ........ *C12N 15/1137* (2013.01); *C12Q 1/6897* (2013.01); *C12Y 304/19012* (2013.01); *C12N 2310/11* (2013.01); *C12N 2310/14* (2013.01); *C12N 2310/315* (2013.01); *C12N 2310/3231* (2013.01)

(58) Field of Classification Search
CPC . C12N 15/111; C12N 15/113; C12N 15/8218; C12N 2310/11; C12N 2310/31; C12N 2310/332
USPC ......... 435/6.11, 6.13, 91.1, 91.31, 375, 455; 514/44; 536/23.1, 24.5
See application file for complete search history.

(56) References Cited

U.S. PATENT DOCUMENTS

| | | | | |
|---|---|---|---|---|
| 5,616,488 A * | 4/1997 | Sullivan | ............. | C07K 14/4702 435/320.1 |
| 7,618,814 B2 * | 11/2009 | Bentwich | ............. | C12N 15/113 435/320.1 |
| 7,655,785 B1 * | 2/2010 | Bentwich | ............. | C12N 15/113 435/320.1 |
| 8,090,542 B2 * | 1/2012 | Khvorova | ............. | A61K 31/713 435/6.1 |
| 8,178,503 B2 * | 5/2012 | Rigoutsos | ............. | G16B 30/00 514/44 A |
| 2004/0023908 A1 * | 2/2004 | Bennett | ............. | C12N 15/113 514/44 A |
| 2004/0241651 A1 * | 12/2004 | Olek | ............. | C07K 14/4703 435/6.16 |
| 2007/0031844 A1 * | 2/2007 | Khvorova | ............. | A61K 31/713 435/6.11 |
| 2007/0207974 A1 * | 9/2007 | Khvorova | ............. | A61K 31/713 514/44 A |
| 2011/0171633 A1 * | 7/2011 | Cowens | ............. | C12Q 1/6886 435/6.1 |
| 2011/0191912 A1 * | 8/2011 | Alexandrov | ......... | C07K 14/415 800/298 |
| 2014/0336237 A1 * | 11/2014 | Swayze | ............. | C07H 21/00 514/44 A |

FOREIGN PATENT DOCUMENTS

| | | | |
|---|---|---|---|
| WO | WO 01/00873 A1 | | 1/2001 |
| WO | WO 02/20545 A1 | | 3/2002 |
| WO | WO 2009121152 | * | 10/2009 |
| WO | WO 2013082448 | * | 6/2013 |

OTHER PUBLICATIONS

Balkhi, et al. 2013 "miR-29 acts as a decoy in sarcomas to protect the tumor suppressor A20 mRNA from degradation by HuR" *Science Signaling* 6(286): 1-22.

Kim, et al. 2012 "MicroRNAs miR-125a and miR-125b constitutively activate that NF-κb pathway by targeting the tumor necrosis factor alpha-induced protein 3 (*TNFAIP3, A20*)," *PNAS* 109(20): 7865-7870.

Murakawa, et al. 2014 "RC3H1 post-transcriptionally regulates A20 mRNA and modulates the activity of the IKK/NF-κB" *Nature Communications* 6: 7367 (in 11 pages).

Wang, et al. 2011 "miR-29c targets TNFAIP3, inhibits cell proliferation and induces apoptosis in hepatitis B virus-related hepatocellular carcinoma" *Biochemical and Biophysical Research Communications* 411: 586-592.

Zhang, et al. 2014 "Induction of the cellular miR-29c by influenza virus inhibits the innate immune response through protection of A20 mRNA" *Biochemical and Biophysical Research Communications* 450: 755-761.

* cited by examiner

*Primary Examiner* — Jane J Zara
(74) *Attorney, Agent, or Firm* — Knobbe, Martens, Olson & Bear, LLP

(57) ABSTRACT

An antisense oligonucleotide comprising a sequence targeted to the 3' untranslated region (3' UTR) of the TNFAIP3 (A20) transcript and its use as a medicament, for example in the treatment of cancer or an autoimmune disease.

Figure 1:
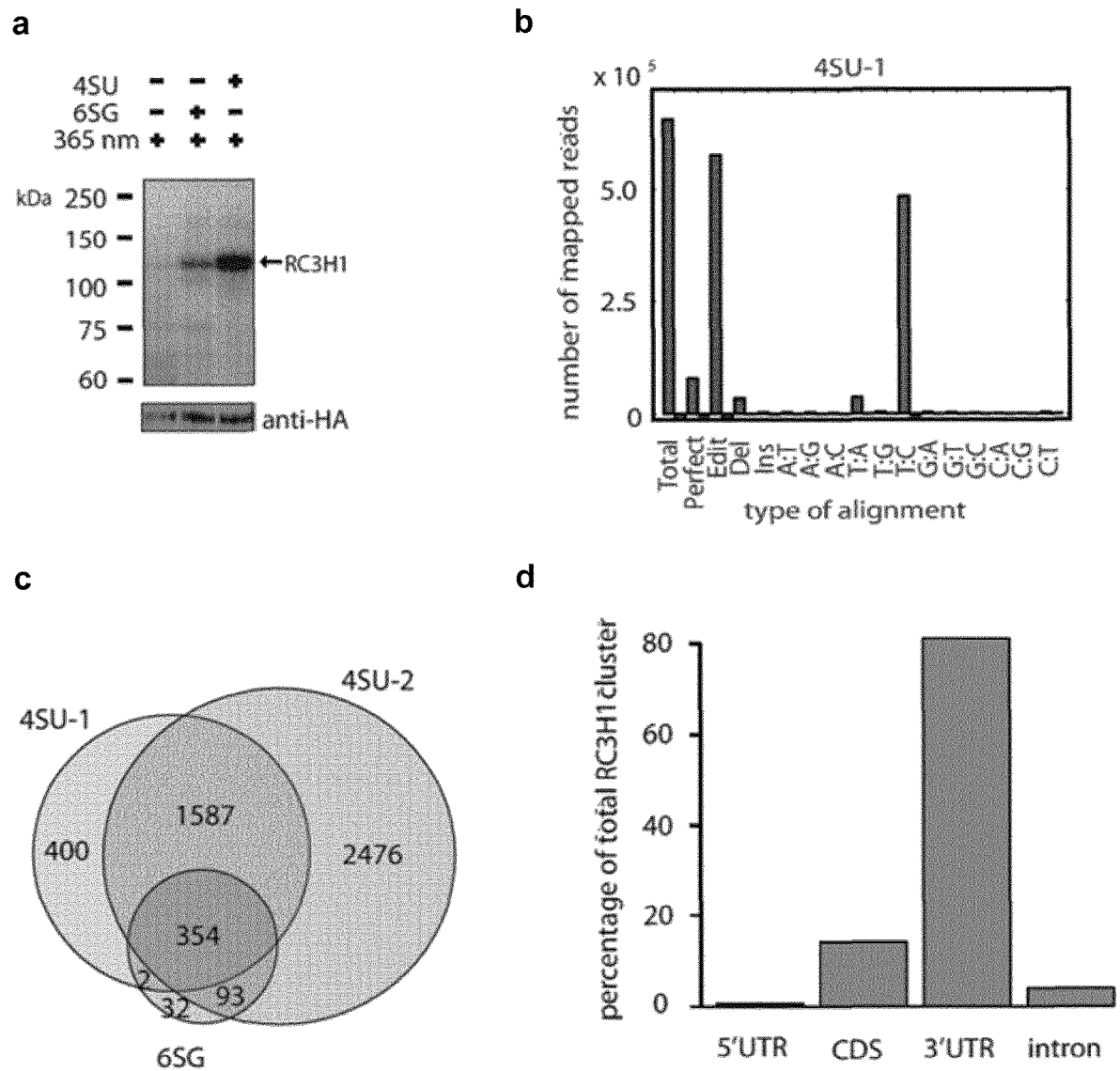

11 Claims, 20 Drawing Sheets
Specification includes a Sequence Listing.

a b a b c d b

```
                             stem      loop    stem
Wt   CATATATAATATACCCTTACATTATGTATGAGGGA
Mut1 CATATATAATATACCCTTACATAATCTATCAGCGA
Mut2 CAAAAAAAAAAAAACCCTTACATAATCTATCAGCGA
Mut3 CAAAAAAAAAAAAACCCTTACATTATGTATGAGGGA
Mut4 CATGTACGATCTGCCCTTACATTATGTATGAGGGA
Mut5 CATGTACGATCTGCCCTTACATAATCTATCAGCGA
Mut6 CATGTACGATCTGCCCTTACAAAATCTATGAGGGA
``` e a b c d f g h a b a b

OLIGONUCLEOTIDE TARGETED TO THE A20-3' UNTRANSLATED REGION

The invention relates to an antisense oligonucleotide comprising a sequence targeted to the 3' untranslated region (3' UTR) of the TNFAIP3 (A20) transcript and its use as a medicament.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 25383421_1.TXT, the date of creation of the ASCII text file is Mar. 2, 2017, and the size of the ASCII text file is 14.2 KB.

BACKGROUND OF THE INVENTION

In the search for novel factors that play important roles in modulating clinically relevant biological processes, innovative strategies must be applied that interrogate the physical and functional interactions between biological molecules. Examples of such techniques relate to those capable of interrogating the myriad of physical interactions between multiple proteins, or in an emerging field of technology, between specific nucleic acids and proteins. Such technologies provide insight into the roles that protein-nucleic acid interactions play in modulating gene expression in the context of biological pathways. In particular, significant effort is required to identify the factors involved in controlling gene expression in disease-relevant in vivo processes, and furthermore, to identify novel means for modulating said factors.

Posttranscriptional regulation of gene expression by RNA-binding proteins (RBPs) controls a variety of cellular processes. Especially, the modulation of messenger RNA (mRNA) stability is of critical importance for the dynamic regulation of genes including transcription factors and cytokines that need to be switched on and off rapidly[1,2].

The present invention has been developed through an approach interrogating protein-mRNA interactions, based on the technology PAR-CLIP (Photoactivatable-Ribonucleoside-Enhanced Crosslinking and Immunoprecipitation). PAR-CLIP has been applied in identifying the mRNA molecules that physically interact with the immune regulator RC3H1 (also known as Roquin).

Roquin is an RNA-binding protein with a central role in repressing autoimmunity[3]. Originally, a missense mutation in the Rc3h1 gene encoding the Roquin protein was identified as the cause of systemic lupus erythematosus-like autoimmunity phenotype in sanroque mice[3]. Roquin binds to the 3' untranslated region (3' UTR) of inducible costimulator (ICOS) mRNA to posttranscriptionally repress its expression[4,5]. Furthermore, Roquin, as well as its paralog roquin-2, interacts with 3'UTR of TNFRSF4 and TNFalpha mRNAs, and modulates immune responses[6,7]. Recent studies showed that roquin protein interacts through its ROQ domain with a constitutive decay element (CDE) in the 3' UTR of TNF mRNA and promotes the decay of this transcript by recruiting the Ccr4-Caf1-Not deadenylase complex[8]. The CDE of TNF folds into a characteristic stem-loop structure containing a specific trinucleotide loop, which is highly similar to the roquin RNA recognition element in the ICOS 3'UTR[8]. Latest structural analyses showed the ROQ domain in complex with a prototypical CDE RNA stem-loop revealing recognition of the RNA stem and its triloop[9,10].

Leppek and colleagues further identified additional Rc3h1 target transcripts by RIP-seq analysis, including regulators of the NF-κB pathway[8]. However, a recognizable CDE was absent in the majority of Rc3h1-bound mRNAs, suggesting other modes of RNA recognition[8]. In line with these findings Schlundt and coworkers showed by mutational and structural analyses of RNA ligands that relaxed CDE consensus sequences can mediate Roquin-dependent regulation[9]. In addition to the ROQ domain, RC3H1 possesses an N-terminal RING finger with a potential E3 ubiquitin-ligase function[11] as well as a CCCH-type zinc finger that is potentially involved in RNA recognition. CCCH-type zinc-finger RNA-binding proteins typically contact AU-rich elements (ARE)[12,13]. AREs are conserved cis-regulatory elements, originally discovered in the 3'UTRs of short-lived mRNAs, encoding cytokines and early expressed immune response genes[14-16].

As is described in more detail herein, RC3H1 contacts mRNAs through structure-sequence elements located in 3'UTRs. The binding sites are composed of a hairpin with embedded AU-rich, or U-rich, sequences but only to a minor extent CDE consensus sequences. RC3H1-bound mRNA targets are short-lived, and RC3H1 depletion resulted in increased protein synthesis of its target mRNAs. RC3H1 target transcripts are significantly enriched for mRNAs that are induced upon DNA damage, amongst them A20 (also known as TNFAIP3) mRNA.

The zinc finger protein A20 codes for a ubiquitin-editing enzyme, which inhibits activation of NF-κB[18,19]. A20 is an important negative regulator of inflammation[19] and several studies have highlighted the clinical and biological importance of A20. Vande Walle and colleagues recently showed that negative regulation of the NLRP3 inflammasome by A20 protects against arthritis[39].

Chronic inflammatory diseases, such as rheumatoid arthritis, inflammatory bowel disease, systemic lupus erythematosus, multiple sclerosis, and type-1 diabetes, among others, are of particular importance and affect more than 50 million individuals in North America alone. Many of these diseases are debilitating and are becoming increasingly common in an aging society.

In light of the significant number of medical conditions associated with inflammation, novel means for the modulation of inflammation, in particular the reduction of inflammation associated with pathological conditions, are required in the medical field.

Antisense oligonucleotides that are capable of modulating A20 expression have been disclosed previously, for example in WO 02/20545, which discloses a number of oligonucleotides capable of inhibiting A20 expression. MicroRNA molecules have also been described that potentially bind the 3' UTR of the A20 transcript and reduce A20 activity (Kim et al, PNAS, May 15, 2012, 109:20, 7865 and Wang et al, Biochemical and Biophysical Research Communications 411 (2011), 586). Other publications have disclosed alternative microRNA molecules that potentially protect A20 from degradation, for example by inhibiting ELAVL1/HuR binding (Balkhi et al, Sci Signal, 6(286) Jan. 9, 2014, and Zhang et al, Biochemical and Biophysical Research Communications 450 (2014), 755. None of the art in this field discloses a physical interaction between RC3H1 and A20 or whether disruption of this interaction could lead to increased A20 levels and/or activity.

The present invention therefore provides novel antisense oligonucleotides comprising a sequence targeted to the 3' untranslated region (3' UTR) of the TNFAIP3 (A20) transcript, capable of disrupting the RC3H1-A20 interaction, thereby increasing A20 levels and/or activity.

SUMMARY OF THE INVENTION

The RNA-binding protein RC3H1 (also known as ROQUIN) promotes constitutive mRNA decay via a constitutive decay element in 3'UTRs. Here, the inventors applied PAR-CLIP to human RC3H1 to identify ~16000 binding sites mapping to ~3800 mRNA targets in human embryonic kidney cells. Computational analyses revealed a structure-sequence motif with AU-rich sequences frequently present in hairpins located in 3'UTRs. RC3H1 binds preferentially short-lived and DNA damage induced mRNAs, such as A20, a ubiquitin-editing enzyme and a major negative regulator of NF-κB signaling. RC3H1 interacts with the A20 3'UTR. Overexpression of RC3H1 results in a reduced A20 protein expression level and increased IκB kinase activation, indicating a role of the RNA-binding protein in the posttranscriptional regulation of the DNA damage response and the IKK/NF-κB pathway. On the other hand depletion of RC3H1 resulted in an upregulation of A20 protein expression which resulted in decreased phosphorylation of IKK and reduced NF-κB DNA-binding activity.

TNFAIP3 is associated with a number of inflammation-associated conditions, such as autoimmune diseases and hematological malignancies. The present invention is based on the surprising finding that RC3H1 regulates the expression level of TNFAIP3 at the post-transcriptional level. In particular, the expression of RC3H1 leads to the down-regulation of TNFAIP3 via physical interaction between RC3H1 protein and the TNFAIP3 3' UTR. On the basis of the newly identified specific RC3H1 target sequence in the 3' UTR of the TNFAIP3 mRNA molecule, oligonucleotides have been developed that interact with the binding site, thereby disrupting the RC3H1-TNFAIP3 mRNA interaction and leading to increased TNFAIP3 levels, assumedly resulting in a reduction in NFKB expression.

In light of the prior art the technical problem underlying the present invention is to provide novel therapeutic compounds that provide an increase in TNFAIP3 (A20) expression and associated therapeutic effects.

This problem is solved by the features of the independent claims. Preferred embodiments of the present invention are provided by the dependent claims.

The invention therefore relates to an antisense oligonucleotide of 8 to 50 nucleobases in length comprising a sequence targeted to the 3' untranslated region (3' UTR) of a TNFAIP3 (A20) transcript.

As demonstrated herein, RC3H1 has been shown to bind the TNFAIP3 3' UTR, acting as a negative regulator of TNFAIP3, thereby maintaining a certain level of expression and/or reducing expression of TNFAIP3. The oligonucleotides of the present invention disrupt the RC3H1 binding to the TNFAIP3 3' UTR, thereby relieving TNFAIP3 of the negative regulation provided by RC3H1. The effect of this disruption in negative regulation may ultimately play a role in NFKB and/or TNF down-regulation, as NFKB is negatively regulated by TNFAIP3. Inhibition of the RC3H1-A20 transcript interaction may in itself be sufficient to provide beneficial anti-inflammatory effects.

The oligonucleotides of the present invention preferably exhibit a length of 8 to 50 nucleobases. In preferred embodiments the length of the nucleotide may be preferably 10 to 45, 12 to 40, 15 to 30 or 17 to 25, more preferably 18, 19, 20, 21, 22, 23 or 24 nucleobases in length, most preferably 21 nucleobases in length.

Oligonucleotides as of 8 nucleobases in length have been demonstrated to be functional in vivo in binding RNA targets (as described in detail in Obad et al, Nature Genetics, 43, 371-378, 2011).

In some embodiments of the invention the oligonucleotides of the present invention exhibit a length of 8 to 200 nucleobases, 8 to 150 nucleobases, 8 to 100 nucleobases or 8 to 80 nucleobases. The length of the oligonucleotide best suited for binding can be determined by assessing the binding or hybridization, for example in an in vitro assay, or by testing the functional effects of RC3H1-A20 transcript disruption, for example according to those experiments as described herein.

In one embodiment of the invention the antisense oligonucleotide as described herein is characterized in that said oligonucleotide specifically hybridizes or binds to the 3' UTR of a TNFAIP3 (A20) transcript, wherein the 3' UTR comprises a sequence according to SEQ ID No. 1, or a sub-sequence of SEQ ID NO 1 functionally involved in RC3H1-binding.

The sequence of SEQ ID No. 1 corresponds to the entire 3' UTR of the human TNFAIP3 transcript. Due to the potentially complex and three-dimension folded structure of a 3' UTR sequence, the oligonucleotides of the invention directed to any region of this sequence may be capable of disrupting the interaction between RC3H1 and TNFAIP3 transcript.

In one embodiment the invention therefore relates to an oligonucleotide that specifically hybridizes or binds to the 3' UTR of a TNFAIP3 (A20) transcript, wherein the 3' UTR comprises a sequence according to SEQ ID No. 1, or a sub-sequence of SEQ ID NO 1 functionally involved in RC3H1-binding as disclosed herein, wherein said binding leads to a disruption in the physical interaction between RC3H1 and the TNFAIP3 transcript.

In a preferred embodiment the oligonucleotide of the present invention directly interacts with and/or binds to the hairpin loop structure of the 3' UTR of the human TNFAIP3 transcript. The hairpin loop structure can be defined by the sequence SEQ ID No. 8 (CCCUUACAUUAU-GUAUGAGGG)

In a preferred embodiment the oligonucleotide of the present invention directly interacts with and/or binds to one or more AU-motifs in the 3' UTR of the human TNFAIP3 transcript. In a preferred embodiment the oligonucleotide of the present invention directly interacts with and/or binds to one or more AU-motifs directly upstream (in the 5' direction) of the hairpin loop structure in the 3' UTR of the human TNFAIP3 transcript.

In a preferred embodiment the oligonucleotide of the present invention directly interacts with and/or binds to one or more AU- or U-motifs in the loop of the hairpin loop structure present in the 3' UTR of the human TNFAIP3 transcript.

According to this invention the term AU-motif relates to an AU sequence, comprising adjacent A and U residues. The relevant preferred AU-motifs are underlined in SEQ ID No. 9 with respect to the corresponding DNA sequences, as provided for the corresponding reporter assay. The AT sequences in the DNA sequence correspond to the relevant AU sequence of the RNA target. Additionally, reference to FIG. 5d shows the AU (or AT) motifs important in oligonucleotide interaction with the 3' UTR of the A20 transcript. These sequence variants are encompassed by SEQ ID No. 10 to 15.

In one embodiment of the invention the antisense oligonucleotide as described herein is characterised in that said oligonucleotide binds to (or specifically hybridizes with) an at least 8-nucleobase portion of the RC3H1 binding site of the 3' UTR of a TNFAIP3 (A20) transcript according to SEQ ID No. 2, SEQ ID No. 3, SEQ ID No. 4, SEQ ID No. 77 and/or SEQ ID No. 5.

The sequence of SEQ ID NO. 2 corresponds to the RC3H1 binding site in the 3' UTR of human TNFAIP3 (A20) transcript according to PAR-CLIP reads.

The sequence of SEQ ID NO. 3 corresponds to the RC3H1 binding site in the 3' UTR of human TNFAIP3 (A20) transcript according to gel-shift assays.

The sequence of SEQ ID NO. 4 corresponds to the RC3H1 binding site in the 3' UTR of human TNFAIP3 (A20) transcript according to PAR-CLIP reads, with an additional 50 nucleotides flanking either side of the binding site. Due to the potentially complex folded structure of a 3' UTR sequence and the physical interaction between proteins and RNA, the oligonucleotides of the invention directed to this region are assumedly capable of disrupting the interaction between RC3H1 and the TNFAIP3 transcript. If, for example, oligonucleotides are applied that comprise more than 20 nucleobases, such as 21 to 40, preferably 21 to 30, or up to 50, or 100 nucleobases, the targeted RNA sequence may lie partially outside the specific RC3H1-binding sequence identified via PAR-CLIP, thereby incorporating flanking sequences into the binding target, as described herein.

The sequence of SEQ ID NO. 77 corresponds to the RC3H1 binding site in the 3' UTR of human TNFAIP3 (A20) transcript according to PAR-CLIP reads, with an additional 20 nucleotides flanking either side of the binding site. Due to the potentially complex folded structure of a 3' UTR sequence and the physical interaction between proteins and RNA, the oligonucleotides of the invention directed to this region are assumedly capable of disrupting the interaction between RC3H1 and the TNFAIP3 transcript. If, for example, oligonucleotides are applied that comprise more than 20 nucleobases, such as 21 to 40, preferably 21 to 30, or up to 50, or 100 nucleobases, the targeted RNA sequence may lie partially outside the specific RC3H1-binding sequence identified via PAR-CLIP, thereby incorporating flanking sequences into the binding target, as described herein.

The sequence of SEQ ID NO. 5 corresponds to the RC3H1 binding site in the 3' UTR of human TNFAIP3 (A20) transcript used in some of the experimental examples.

These sequences have been verified as directly interacting with RC3H1, both in vivo and in vitro, and an oligonucleotide targeted to this region may disrupt the binding of RC3H1 to the TNFAIP3 (A20) transcript as shown as in FIG. 5C.

The oligonucleotides preferably specifically hybridize (or bind to) an at least 8-nucleobase portion of any one of these RC3H1 binding sites, or in other embodiments a 9, 10, 11, 12, 13, 14, 15, 16, 17, 18, 19, 20, 21, 22, 23, 24, 25, 26, 27, 28, 29, or 30-nucleobase portion. The oligonucleotide as described herein may be longer than the portion of its sequence that hybridizes to the target sequence. The oligonucleotide as described herein may essentially bind any given region of the indicated target sequences, preferably according to SEQ ID 1, 2, 3, 4 and/or 5, so that a disruption in the binding of RC3H1 to the TNFAIP3 transcript occurs.

In one embodiment of the invention the antisense oligonucleotide as described herein is characterised in that said oligonucleotide of 8 to 50 nucleobases in length comprises a sequence of at least 80%, preferably more than 90%, more preferably more than 95% sequence identity to SEQ ID No. 1, SEQ ID No. 2, SEQ ID No. 3, SEQ ID No. 4 and/or SEQ ID No. 5 and/or complementary sequence thereof and hybridizes/binds to the 3' UTR of a TNFAIP3 (A20) transcript.

In one embodiment of the invention the antisense oligonucleotide as described herein is characterised in that said oligonucleotide of 8 to 50, preferably 12 to 40, 15 to 30 or 18 to 25, more preferably 21, nucleobases in length and comprises a sequence that is fully complementary to an at least 8-nucleobase portion, preferably a 12, 15, 18, or more preferably a 21-nucleobase portion, of the RC3H1 binding site according to SEQ ID No. 2, 3, 4 and/or 5 or complement of SEQ ID No. 2, 3, 4 and/or 5.

In a preferred embodiment the antisense oligonucleotide as described herein is characterised in that the oligonucleotide comprises 12 to 40 nucleobases in length, preferably 15 to 30 nucleobases in length, and the oligonucleotide comprises a sequence that is fully complementary to an at least 12 nucleobase portion, preferably a 15, 18, or 21-nucleobase portion, of the RC3H1 binding site according to SEQ ID No. 2, SEQ ID No. 3 and/or SEQ ID No. 5.

In one embodiment of the invention the antisense oligonucleotide as described herein is characterised in that said oligonucleotide consists of a sequence according to SEQ ID No. 3 or 5 or complement, DNA or LNA counterpart thereof.

The sequence of SEQ ID NO. 6 corresponds to the LNA oligonucleotide targeted against the RC3H1 binding site in the 3' UTR of human TNFAIP3 (A20) transcript. This LNA was used in the experimental examples and shown to exhibit the desired effect regarding RC3H1-A20 disruption.

In one embodiment of the invention the antisense oligonucleotide as described herein is characterised in that said oligonucleotide of 8 to 50 nucleobases in length comprises a sequence of SEQ ID No. 6, or a sequence of at least 80%, preferably more than 90%, more preferably more than 95% sequence identity to SEQ ID No. 6 and/or complementary sequence thereof and preferably disrupts the interaction between RC3H1 and the TNFAIP3 (A20) transcript.

The oligonucleotides comprising SEQ ID No. 6 (or sequence of 80%, 90% or 95% identity or more to SEQ ID No. 6) of the present invention preferably exhibit a length of 8 to 50 nucleobases. In preferred embodiments the length of the nucleotide may be preferably 10 to 45, 12 to 40, 15 to 30 or 17 to 25, more preferably 18, 19, 20, 21, 22, 23 or 24 nucleobases in length, most preferably 21 nucleobases in length. In some embodiments of the invention the oligonucleotides of the present invention comprising SEQ ID No. 6 (or sequence of 80%, 90% or 95% identity or more to SEQ ID No. 6) exhibit a length of 8 to 200 nucleobases, 8 to 150 nucleobases, 8 to 100 nucleobases or 8 to 80 nucleobases. The length of the oligonucleotide best suited for binding can be determined by assessing the binding or hybridization, for example in an in vitro assay, or by testing the functional effects of RC3H1-A20 transcript disruption, for example according to those experiments as described herein.

In one embodiment of the invention the antisense oligonucleotide as described herein is characterised in that said oligonucleotide consists of a sequence according to SEQ ID No. 6 or complement, RNA or LNA counterpart thereof.

In one embodiment of the invention the antisense oligonucleotide as described herein is characterised in that said oligonucleotide comprises at least one structural modification, for example of the backbone, linkage, nucleobases and/or sugar structure, that provides improved stability and/or half-life of said oligonucleotide post-administration in a cell and/or organism compared to a structurally unmodified oligonucleotide of the same sequence. Structural modifications capable of enhancing in vivo stability are known to those skilled in the art and may be applied in the present invention.

In one embodiment of the invention the antisense oligonucleotide as described herein is characterised in that said oligonucleotide comprises a modified internucleoside linkage, such as a phosphorothioate linkage. Nuclease stability is important for antisense and RNAi applications where oligonucleotides are exposed to exonucleases and endonucleases within cells. The modification of oligonucleotides by exchanging a non-bridging oxygen on the phosphate backbone to form a phosphorothioate (PS) linkage is well known in the art. A phosphorothioate linkage is capable of protecting antisense oligonucleotides from nuclease degradation, prolonging their lifetime in serum. It is an inexpensive option and is effective, and nuclease resistance may be further enhanced when optionally combined with a 2' O-methyl or 2'-O-methoxyethyl modification.

In one embodiment of the invention the antisense oligonucleotide as described herein is characterised in that said oligonucleotide comprises at least one modified sugar moiety, such as a 2'-O-methyl (2'-O-Me) or 2'-O-methoxyethyl (2'-O-MOE) sugar moiety or a bicyclic sugar moiety. The modified oligonucleotides may contain 2'-O-(2-methoxyethyl) (2'-O-MOE) ribose sugar modifications on all or a portion of the nucleotides in the antisense sequence. The 2' O-Methyl modification is characterized as an RNA analogue that offers stability against general base hydrolysis and nucleases. The 2'-O-MOE-modified oligonucleotides are typically more resistant to nuclease metabolism in both plasma and tissue post-administration.

In one embodiment of the invention the antisense oligonucleotide as described herein is characterised in that the modified sugar moiety is a bicyclic sugar moiety that has a (—CH$_2$—)n group forming a bridge between the 2' oxygen and the 4' carbon atoms of the sugar ring, wherein n is 1 or 2. This embodiment relates to a locked nucleic acid (LNA), often referred to as inaccessible RNA, which is a modified RNA nucleotide. The ribose moiety of an LNA nucleotide is modified with an extra bridge connecting the 2' oxygen and 4' carbon. The bridge "locks" the ribose in the 3'-endo conformation. LNA nucleotides can be mixed with DNA or RNA residues in the oligonucleotide whenever desired. Such oligomers are synthesized chemically and are commercially available. The locked ribose conformation enhances base stacking and backbone pre-organization. This significantly increases the hybridization properties (melting temperature) of oligonucleotides and assists against nuclease degradation.

The oligonucleotide of SEQ ID No. 6 may in one embodiment relate to an LNA molecule with one or more Locked Nucleic Acid modified residues within the oligonucleotide. In a preferred embodiment the sequence relates to +AA+AT+CC+CT+CA+TA+CA+TAA+T. Note that + indicates that the following nucleobase is present as a Locked Nucleic Acid (LNA) modified residue.

According to the present invention the term "oligonucleotide" encompasses compounds that comprise naturally and/or non-naturally occurring building blocks, such as nucleobases, nucleosides and/or nucleotides, and/or modified nucleobases, modified nucleosides and/or modified nucleotides, or oligonucleotides with any given structural modification, for example those described herein used for increasing in vivo half-life of the molecule, whereby the oligonucleotide is capable of biding the A20 3' UTR sequences described herein.

The invention also encompasses a nucleic acid molecule, such as a vector, a plasmid, virus, or other nucleic acid expression construct, which encodes the anti-sense oligonucleotide described herein. The invention also relates to a cell, for example a bacterial or mammalian cell, comprising said nucleic acid molecule, useful in for example propagating the nucleic acid or for expression or production of the oligonucleotide, for example in vitro, or in vivo, for example in the context of gene or cell therapy.

In one embodiment of the invention the antisense oligonucleotide as described herein is characterised in that said oligonucleotide:
  a. inhibits or disrupts the binding of RC3H1 protein to the 3' UTR of a TNFAIP3 (A20) transcript,
  b. increases expression, amount of and/or activity of TNFAIP3 (A20), and/or
  c. increases IκB kinase activity;
upon binding of said oligonucleotide to its target.

As described in more detail herein, the oligonucleotides of the present invention may be characterised by their functional attributes with respect to disruption of the binding of RC3H1 protein to the 3' UTR of a TNFAIP3 (A20) transcript, the subsequent increase in expression and/or activity of TNFAIP3 or the ultimate modulation in NFKB and/or TNF expression and/or activity.

The antisense oligonucleotide of the present invention may be used as a medicament. The treatment of any given medical condition is encompassed. Until the present time a medical use of such oligonucleotides has been neither disclosed nor suggested in the art.

The antisense oligonucleotide of the present invention may be used as a medicament in the treatment of a medical condition associated with inflammation, such as rheumatoid arthritis or psoriasis, or of an autoimmune disease, such as systemic lupus erythematosus (SLE) or Crohn's disease.

The antisense oligonucleotide of the present invention may be used as a medicament in the treatment of a medical condition associated with an unwanted cell proliferation, preferably cancer, such as B-cell lymphoma.

In a further aspect of the invention a pharmaceutical composition is provided comprising the antisense oligonucleotide as described herein or a pharmaceutically acceptable salt thereof and a pharmaceutically acceptable carrier.

In a further aspect of the invention a reporter system is provided which has been specifically developed for measuring the binding of an oligonucleotide to the 3' UTR of TNFAIP3.

In a preferred embodiment the invention provides a method for detecting and/or measuring the binding of a candidate molecule, preferably a candidate oligonucleotide, to the 3' UTR of TNFAIP3 (A20), comprising
  providing a nucleic acid reporter construct comprising the 3' UTR of TNFAIP3 functionally linked to a marker molecule, such as GFP or luciferase,
  bringing a candidate molecule, preferably a candidate oligonucleotide, into contact and/or into proximity with said reporter construct, preferably in a cell, and
  assessing reporter activity via expression of said marker molecule, for example by detection of fluorescence of GFP or light emission from luciferase.

In a preferred embodiment the method for detecting and/or measuring the binding of a candidate molecule, preferably a candidate oligonucleotide, to the 3' UTR of TNFAIP3 as described herein is characterised in that the nucleic acid reporter construct comprising the 3' UTR of TNFAIP3 comprises of a nucleic acid molecule that comprises or consists of a sequence of at least 80%, preferably more than 90%, more preferably more than 95% sequence identity to SEQ ID No. 1 to 5 and/or complementary sequence thereof.

The method and reporter construct described herein relate to means for carrying out a screening method for candidate molecules, such as oligonucleotides, small molecules, natural products or other potential inhibitors, that exhibit beneficial properties of interruption or inhibition of the physical interaction and/or the binding between RC3H1 protein to the 3' UTR of a TNFAIP3 (A20) transcript. Chemical libraries may be applied, for example using high throughput screening, in order to interrogate potential desired activity of a large number of compounds.

The reporter construct of the present invention comprises essentially of a marker molecule that can be assessed during a corresponding method due its expression level. Such a reporter may relate to either GFP, or luciferase, or other fluorescent or light emitting molecule. Other reporter molecules that may enable simple assessment of their expression are also encompassed herein. Essentially any given protein may be used, for which suitable detection reagents (either microscopic or molecular, such antibodies or similar reagents) are available.

The reporter construct also comprises the 3'UTR harboring the RC3H1 A20 binding site including the upstream AU-rich sequence and/or stem-loop structure.

This construct can be transfected into (preferably HEK293) cells. Candidate compounds, to be tested for a potential interaction or disruption of the A20 transcript-RC3H1 binding, may be applied to the cell or introduced into the cell and the marker molecule subsequently assessed to examine whether changes in expression of the marker molecule have occurred.

Determination of an interaction between the mRNA corresponding to the reporter construct and the candidate molecule may also be carried out outside a cell, for example in in vitro.

In a preferred embodiment the reporter constructs utilises a destabilized GFP (d2GFP) reporter construct with a 3'UTR harboring the RC3H1 A20 binding site including the upstream AU-rich sequence and stem-loop structure.

Since the d2GFP protein half-life is shortened to about 2 hours by a C-terminal fusion to a PEST domain, the expression level of d2GFP measured by FACS analysis likely approximates the abundance of d2GFP mRNA. As shown in the examples below, insertion of the A20 site into the 3'UTR of the reporter construct reduced d2GFP expression, indicating a repressive effect in HEK293 cells.

The invention therefore encompasses the reporter construct itself as described herein, in addition to any screening method based on the use of said reporter construct.

DETAILED DESCRIPTION OF THE INVENTION

The sequences provided herein may relate to DNA, RNA, LNA or other nucleic acid variant sequences, or combinations thereof, for example to other structural variants described herein. The complementary sequences are also encompassed in the scope of the invention. If RNA sequences are provided, the corresponding specific DNA sequences are also provided within the scope of the invention, so that for example uracil (U) may be exchanged with thymine (T) as required to encompass both RNA and DNA sequences.

TABLE 1a

Preferred sequences of the invention.

| SEQ ID NO. | Sequence (5'-3') | Description |
|---|---|---|
| 1 | CCGGAAACAGGUGGGU CACCUCCUGCAAGAAG UGGGGCCUCGAGCUGU CAGUCAUCAUGGUGCU AUCCUCUGAACCCCUC AGCUGCCACUGCAACA GUGGGCUUAAGGGUGU CUGAGCAGGAGAGGAA AGAUAAGCUCUUCGUG GUGCCCACGAUGCUCA GGUUUGGUAACCCGGG AGUGUUCCCAGGUGGC CUUAGAAAGCAAAGCU UGUAACUGGCAAGGGA UGAUGUCAGAUUCAGC CCAAGGUUCCUCCUCU CCUACCAAGCAGGAGG CCAGGAACUUCUUUGG ACUUGGAAGGUGUGCG GGGACUGGCCGAGGCC CCUGCACCCUGCGCAU CAGGACUGCUUCAUCG UCUUGGCUGAGAAAGG GAAAAGACACACAAGU CGCGUGGGUUGGAGAA GCCAGAGCCAUUCCAC CUCCCCUCCCCCAGCA UCUCUCAGAGAUGUGA AGCCAGAUCCUCAUGG CAGCGAGGCCCUCUGC AAGAAGCUCAAGGAAG CUCAGGGAAAAUGGAC GUAUUCAGAGAGUGUU UGUAGUUCAUGGUUUU UCCCUACCUGCCCGGU UCCUUUCCUGAGGACC CGGCAGAAAUGCAGAA CCAUCCAUGGACUGUG AUUCUGAGGCUGCUGA GACUGAACAUGUUCAC AUUGACAGAAAAACAA GCUGCUCUUUAUAAUA UGCACCUUUUAAAAAA UUAGAAUAUUUUACUG GGAAGACGUGUAACUC UUUGGGUUAUUACUGU CUUUACUUCUAAAGAA GUUAGCUUGAACUGAG GAGUAAAAGUGUGUAC AUAUAUAAUAUACCCU UACAUUAUGUAUGAGG GAUUUUUUUAAAUUAU AUUGAAAUGCUGCCCU AGAAGUACAAUAGGAA GGCUAAAUAAUAAUAA CCUGUUUUCUGGUUGU UGUUGGGGCAUGAGCU UGUGUAUACACUGCUU GCAUAAACUCAACCAG CUGCCUUUUUAAAGGG AGCUCUAGUCCUUUUU GUGUAAUUCACUUUAU UUAUUUUAUUACAAAC UUCAAGAUUAUUUAAG UGAAGAUAUUUCUUCA GCUCUGGGGAAAAUGC CACAGUGUUCUCCUGA GAGAACAUCCUUGCUU UGAGUCAGGCUGUGGG CAAGUUCCUGACCACA GGGAGUAAAUUGGCCU CUUUGAUACACUUUUG CUUGCCUCCCCAGGAA AGAAGGAAUUGCAUCC | 3' UTR of human TNFAIP3 (A20) transcript |

TABLE 1a-continued

Preferred sequences of the invention.

| SEQ ID NO. | Sequence (5'-3') | Description |
|---|---|---|
| | AAGGUAUACAUACAUA UUCAUCGAUGUUUCGU GCUUCUCCUUAUGAAA CUCCAGCUAUGUAAUA AAAAACUAUACUCUGU GUUCUGUUAAUGCCUC UGAGUGUCCUACCUCC UUGGAGAUGAGAUAGG GAAGGAGCAGGGAUGA GACUGGCAAUGGUCAC AGGGAAAGAUGUGGCC UUUUGUGAUGGUUUUA UUUUCUGUUAACACUG UGUCCUGGGGGGCUG GGAAGUCCCCUGCAUC CCAUGGUACCCUGGUA UUGGGACAGCAAAAGC CAGUAACCAUGAGUAU GAGGAAAUCUCUUUCU GUUGCUGGCUUACAGU UUCUCUGUGUGCUUUG UGGUUGCUGUCAUAUU UGCUCUAGAAGAAAAA AAAAAAAGGAGGGGAA AUGCAUUUUCCCCAGA GAUAAAGGCUGCCAUU UUGGGGGUCUGUACUU AUGGCCUGAAAAUAUU UGUGAUCCAUAACUCU ACACAGCCUUUACUCA UACUAUUAGGCACACU UUCCCCUUAGAGCCCC CUAAGUUUUUCCCAGA CGAAUCUUUAUAAUUU CUUUCCAAAGAUACCA AAUAAACUUCAGUGUU UUCAUCUAAUUCUCUU AAAGUUGAUAUCUUAA UAUUUUGUGUUGAUCA UAUUUCCAUUCUUAA UGUGAAAAAAGUAAU UAUUUAUACUUAUUAU AAAAAGUAUUUGAAAU UUGCACAUUUAAUUGU CCCUAAUAGAAAGCCA CCUAUUCUUUGUUGGA UUUCUUCAAGUUUUUC UAAAUAAAUGUAACUU UUCACAAGAGUCAACA UUAAAAAAUAAAUUAU UUAAGAACAGAAAAAA AAAAAAAAA | |
| 2 | UACAUAUAUAAUAUAC CCUUACAUUAUGUAUG AGGGAUUUUUUAAAU UAUAUUGAAAU | RC3H1 binding site in the 3' UTR of human TNFAIP3 (A20) transcript according to PAR-CLIP reads |
| 3 | AUAUAUAAUAUACCCU UACAUUAUGUAUGAGG GAUUU | RC3H1 binding site in the 3' UTR of human TNFAIP3 (A20) transcript according to gel-shift assays; Anti-sense oligonucleotide |
| 4 | ACUGUCUUUACUUCUA AAGAAGUUAGCUUGAA CUGAGGAGUAAAAGUG UGUACAUAUAUAAUAU ACCCUUACAUUAUGUA UGAGGGAUUUUUUAA AUUAUAUUGAAAUGCU GCCCUAGAAGUACAAU AGGAAGGCUAAAUAAU AAUAACCUGUUUUCU | RC3H1 binding site in the 3' UTR of human TNFAIP3 (A20) transcript according to PAR-CLIP reads with 50 nucleotides flanking either side of the identified binding region |
| 77 | AACUGAGGAGUAAAAG UGUGUACAUAUAUAAU AUACCCUUACAUUAUG UAUGAGGGAUUUUUUU AAAUUAUAUUGAAAUG CUGCCCUAGAAGUACA AUA | RC3H1 binding site in the 3' UTR of human TNFAIP3 (A20) transcript according to PAR-CLIP reads with 20 nucleotides flanking either side of the identified binding region |
| 5 | ACCCUUACAUUAUGUA UGAGGGA | RC3H1 binding site in the 3' UTR of human TNFAIP3 (A20) transcript; Anti-sense oligonucleotide |
| 6 | AAATCCCTCATACATA AT | LNA (DNA) sequence used in the experimental examples shown to disrupt the Rc3H1-A20 transcript interaction; Anti-sense oligonucleotide |
| 7 | TGTACATATATAATAT ACCCTTACATTATGTA TGAGGGATTTT | Regulatory Sequence of the d2EGFP Reporter; Stems of the hairpin loop are displayed as underlined |
| — | TGTACATATATAATAT ACCCTTACATTATGTA TGAGGGATTTTTAATA CATACTCCCTAAA | Shown schematically is the potential interaction between the LNA of SEQ ID No. 6 (in reverse; from 3' to 5') and the regulatory Sequence of the d2EGFP Reporter (SEQ ID No. 7) that corresponds to the A20 3' UTR hairpin loop |
| 8 | CCCUUACAUUAUGUAU GAGGG | hairpin loop sequence of the 3' UTR of human TNFAIP3 (A20) transcript |
| 9 | CATATATAATATACCC TTACATTATGTATGAG GGA | WT stem loop sequence; underline indicates sequence corresponding to AU-rich sequences of interest |
| 10 | CATATATAATATACCC TTACATAATCTATCAG CGA | Mut1 stem loop sequence |
| 11 | CAAAAAAAAAAAACCC TTACATAATCTATCAG CGA | Mut2 stem loop sequence |
| 12 | CAAAAAAAAAAAACCC TTACATTATGTATGAG GGA | Mut3 stem loop sequence |
| 13 | CATGTACGATCTGCCC TTACATTATGTATGAG GGA | Mut4 stem loop sequence |
| 14 | CATGTACGATCTGCCC TTACATAATCTATCAG CGA | Mut5 stem loop sequence |
| 15 | CATGTACGATCTGCCC TTACAAATCTATGAG GGA | Mut6 stem loop sequence |

With respect to the preferred oligonucleotides of the invention, it is preferred to target specific nucleic acids to their antisense sequence. "Targeting" an antisense compound to a particular nucleic acid, in the context of this invention, is a multistep process. The process usually begins with the identification of a nucleic acid sequence whose function is to be modulated. In the present invention, the target is a nucleic acid molecule of the 3' UTR of TNFAIP3. The targeting process also includes determination of a site or sites within this gene for the antisense interaction to occur such that the desired effect, e.g., detection or modulation of expression of the protein, will result. Within the context of the present invention, a preferred site is the region of the TNFAIP3 3' UTR that is bound directly or interacts with RC3H1. The sequences may be disclosed herein as targets, or as anti-sense oligonucleotides. A skilled person is aware that the targets may also be used as anti-sense oligonucleotides through appropriate selection of the reverse-complement sequence that binds the corresponding target.

An oligonucleotide "targeted" to any given nucleic acid region refers to an oligonucleotide capable of specifically binding to (or hybridizing) to the particular target nucleic acid sequence. Specific binding does not refer to absolute absence of binding to other targets. Although some cross-specificity may be found, whereby a nucleotide may bind to additional sequences than the preferred target sequence, the specific binding is considered to encompass binding events that occur more preferentially under either in vivo or in vitro conditions compared to binding to other target sequences.

In the context of this invention, "hybridization" (also referred to as binding) means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds.

Hybridization may be assessed by a hybridization assay, as are well known in the art (for example in Human Molecular Genetics—Tom Strachan, Andrew Read, 4th Ed.). Nucleic acid hybridization is a fundamental property known in molecular genetics which relates to the ability of individual single-stranded nucleic acid molecules to form double-stranded molecules (that is, to hybridize to each other). For this to happen, the interacting single-stranded molecules must have a sufficiently high degree of base complementarity. Standard nucleic acid hybridization assays involve using a labeled nucleic acid probe to identify related DNA or RNA molecules (that is, ones with a significantly high degree of sequence similarity) within a sample of potential target nucleic acid molecules. Nucleic acid hybridization involves mixing single strands of two sources of nucleic acids, a probe (e.g. chemically synthesized oligonucleotides) and a target. If either the probe or the target is initially double-stranded, the individual strands must be separated, generally by heating or by alkaline treatment. After mixing single strands of probe with single strands of target, strands with complementary base sequences can be allowed to reassociate. Complementary probe strands can reanneal to form homoduplexes, as can complementary target DNA strands. However, it is the annealing of a probe DNA strand and a complementary target DNA strand to form a labeled probe-target heteroduplex that defines the usefulness of a nucleic acid hybridization assay. The rationale of the hybridization assay is to use the probe to assess binding to the target DNA.

"Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target.

It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention which hybridize to the target and inhibit expression of the target are identified through experimentation, and the sequences of these compounds are herein identified as preferred embodiments of the invention. The target sites to which these preferred sequences are complementary may herein be referred to as "active sites" and are therefore preferred sites for targeting. Therefore another embodiment of the invention encompasses compounds which hybridize to these active sites.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use. For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimens for treatment of cells, tissues and animals, especially humans.

In the context of this invention, the term "oligonucleotide" refers to an oligomer or polymer of ribonucleic acid (RNA) or deoxyribonucleic acid (DNA) or any mimetic or structurally modified nucleic acid thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention encompasses other oligomeric antisense compounds, including but not limited to oligonucleotide mimetics such as are described below. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases.

The oligonucleotides of the present invention therefore encompass oligonucleotides comprising 8 to 200, 8 to 150 8 to 80 or preferably 8 to 50 nucleobases, 9 to 45, 10 to 40, 11 to 35, 12 to 30, 13 to 29, 14 to 28, 15 to 27, 16 to 26, or 17 to 25 nucleobases in length.

The oligonucleotides of the present invention therefore encompass oligonucleotides described herein, such as according to SEQ ID No. 3, 5 or 6, may in some embodiments be characterized by a 0 to 10 nucleobase addition or deletion, preferably a 0 to 5 nucleobase addition or deletion, at the 5' and/or 3' end of a sequence.

As used herein the term "a 0 to 5 nucleobase addition or deletion at the 5' and/or 3' end of a sequence" means that the oligonucleotide or nucleic acid, preferably according to SEQ ID No. 3, 5 or 6, may have a) 0, 1, 2, 3, 4, 5, 6, 7, 8, 9, or 10 additional nucleobases at its 5' end and 0, 1, 2, 3, 4, 5, 6, 7, 8, 9 or 10 nucleobases deleted at its 3' end orb) 0, 1, 2, 3, 4, 5, 6, 7, 8, 9 or 10 additional nucleobases at its 3' end and 0, 1, 2, 3, 4, 5, 6, 7, 8, 9 or 10 nucleobases deleted at its 5' end, c) 0, 1, 2, 3, 4, 5, 6, 7, 8, 9 or 10 additional nucleobases at its 5' end and 0, 1, 2, 3, 4, 5, 6, 7, 8, 9 or 10 additional nucleobases at its 3' end or d) 0, 1, 2, 3, 4, 5, 6, 7, 8, 9 or 10 nucleobases deleted at its 5' end and 0, 1, 2, 3, 4, 5, 6, 7, 8, 9 or 10 nucleobases deleted at its 3' end. Minor changes in the length of the oligonucleotides described herein may be carried out by a skilled person without undue effort.

In one embodiment the method of the present invention is characterized in that the one or more oligonucleotides comprises a nucleotide sequence with more than 80% sequence identity, preferably more than 85%, preferably more than 90%, preferably more than 95% sequence identity, to the sequences provided herein, for example, 80, 81, 82, 83, 84, 85, 86, 87, 88, 89, 90, 91, 92, 93, 94, 95, 96, 97, 98, 99% sequence identity. The sequence variant with between 80% and 99% sequence identity is preferably functionally analogous, i. e. sequences that although exhibiting differences in DNA sequence, so that for example binding to the 3' UTR of an A20 transcript is similarly maintained, so that the function of the oligonucleotide in the context of the present invention is maintained. Functionally analogous sequences can be tested by one skilled in the art without inventive effort in light of the information provided within the application, for example by testing binding and/or hybridization properties as disclosed herein.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside.

Specific examples of preferred antisense compounds useful in this invention include oligonucleotides containing modified backbones or non-natural internucleoside linkages. The invention encompasses oligonucleotide with at least one structural modification that provides improved stability and/or half-life of said oligonucleotide post-administration in a cell and/or organism compared to a structurally unmodified oligonucleotide of the same sequence. Preferred modified oligonucleotide backbones include, for example, phosphorothioates, chiral phosphorothioates, phosphorodithioates, phosphotriesters, aminoalkylphosphotriesters, methyl and other alkyl phosphonates. Various salts, mixed salts and free acid forms are also included.

In other preferred oligonucleotide variants, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a (—CH2-)n group bridging the 2' oxygen atom and the 4' carbon atom wherein n is 1 or 2. LNAs and preparation thereof are described in WO 98/39352 and WO 99/14226.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). In the context of the present invention, reference to oligonucleotide sequences that use (U) in the context of an RNA sequence may also relate to the DNA counterpart of the sequence, thereby encompassing the same sequence in which (T) is present in place of (U), and vice versa.

Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound.

A skilled person is aware of appropriate methods of oligonucleotide synthesis. Modern techniques enable rapid and inexpensive custom-made oligonucleotides of a desired sequence. For example, a common process relates to solid-phase synthesis using phosphoramidite method and phosphoramidite building blocks derived from protected 2'-deoxynucleosides (dA, dC, dG, and T), ribonucleosides (A, C, G, and U), or chemically modified nucleosides, e.g. LNA, BNA. To obtain the desired oligonucleotide, the building blocks (modified or naturally occurring) are sequentially coupled to the growing oligonucleotide chain in the order required by the sequence of the product. Upon the completion of the chain assembly, the product is released from the solid phase to solution, deprotected, and collected. Products may be isolated by high-performance liquid chromatography (HPLC) to obtain the desired oligonucleotides in high purity, if required.

The antisense compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents. The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of TNFAIP3 is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Certain compositions of the present invention also incorporate carrier compounds in the formulation. As used herein, "carrier compound" or "carrier" can refer to a nucleic acid, or analogue thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on EC50s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

Rc3h1 (also known as Roquin), originally identified as the causative gene for autoimmunity in sanroque mice, is ubiquitously expressed RNA-binding-protein, whose functional role has mostly been studied in cells of the immune system. The inventors have applied PAR-CLIP to the human RC3H1 to identify transcriptome-wide around 16000 binding sites on about 3800 mRNA targets. RC3H1 binding sites are enriched for an U-rich motif embedded in the loop of RNA hairpin structures and are mainly located in the 3'UTR of target mRNAs. As demonstrated herein, RC3H1 is involved in the regulation of apoptosis and DNA damage response, in addition to NFKB regulation, through repression of TNFAIP3/A20 mRNA at the posttranscriptional level. The development of oligonucleotide molecules that disrupt the NF-κB protein-A20 mRNA interaction ultimately lead to an alleviation of A20 suppression and subsequently a reduction in NFKB levels.

Tumor necrosis factor, alpha-induced protein 3 (TNFAIP3 or A20, used interchangeably herein) is a protein that in humans is encoded by the TNFAIP3 gene. This gene was identified as a gene whose expression is rapidly induced by the tumor necrosis factor (TNF). The protein encoded by this gene is a zinc finger protein, and has been shown to inhibit NF-κB activation as well as TNF-mediated apoptosis. Knockout studies of a similar gene in mice suggested that this gene is critical for limiting inflammation by terminating TNF-induced NF-κB responses (see for example Opipari et al, J Biol Chem 265 (25): 14705-8; Heyninck et al, J. Cell Biol. 145 (7): 1471-82; Song et al, PNAS 93 (13): 6721-5).

TNFAIP3 is a known negative regulator of NF-κB (nuclear factor kappa-light-chain-enhancer of activated B cells), which is a protein complex that controls transcription of DNA. NF-κB is found in essentially all mammalian cells and is involved in a large number of cellular responses to stimuli such as stress, cytokine production and bacterial or viral antigens. NF-κB plays a key role in regulating the immune response to infection; incorrect regulation of NF-κB has also been linked to cancer, inflammatory and autoimmune diseases, such as septic shock, viral infection, inflammatory bowel disease, arthritis, gastritis, asthma and atherosclerosis. NF-κB controls many genes involved in inflammation and is found to be chronically active in a number of inflammatory diseases. NF-κB is also involved in eukaryotic cells as a regulator of cell proliferation and survival and therefore is found to be mis-regulated in a number of tumours. New approaches towards NF-κB modulation, in particular to suppression of unwanted NF-κB expression and/or activity are required in the art, in particular in medical fields regarding the treatment of inflammation and cancer.

TNFAIP3 has also been associated previously with various disorders known to relate to inflammatory process. Inflammation is part of the complex biological response of vascular tissues to harmful stimuli, such as pathogens, damaged cells, or irritants. The classical signs of acute inflammation are pain, heat, redness, swelling, and loss of function. Inflammation is a protective attempt by the organism to remove the injurious stimuli and to initiate the healing process. However, chronic inflammation can also lead to a host of diseases, such as hay fever, periodontitis, atherosclerosis, rheumatoid arthritis, and even cancer. It is for that reason that inflammation is normally closely regulated by the body. Inflammation in a patient can also be detected via molecular approaches, for example by monitoring biological molecules known to associate with inflammation. Examples of such tests relate to, for example, molecular assays such as immune based methods (for example ELISA) or other nucleic acid based techniques, such as RT-PCR, may be used. Markers for inflammation may include, but are not limited to, IL-6 (Interleukin-6), IL-8 (Interleukin-8), IL-18 (Interleukin-18), TNF-α (Tumor necrosis factor-alpha), CRP (C-reactive protein), Insulin, Blood glucose or Leptin.

Myeloid-cell-specific deletion of the rheumatoid arthritis susceptibility gene A20/Tnfaip3 in mice (A20(myel-KO) mice) triggers a spontaneous erosive polyarthritis that resembles rheumatoid arthritis in patients. Rheumatoid arthritis in A20(myel-KO) mice is not rescued by deletion of tumour necrosis factor receptor 1. Vande Walle and colleagues[39] show that it crucially relies on the Nlrp3 inflammasome and interleukin-1 receptor signalling. Macrophages lacking A20/Tnfaip3 have increased basal and lipopolysaccharide-induced expression levels of the inflammasome adaptor Nlrp3 and proIL-1β. As a result, A20-deficiency in macrophages significantly enhances Nlrp3 inflammasome-mediated caspase-1 activation, pyroptosis and interleukin-1β secretion. These results reveal A20/Tnfaip3 as a novel negative regulator of Nlrp3 inflammasome activation. The indication of inflammasome regulation by A20/Tnfaip3 provides sound support for anti-inflammatory properties of the oligonucleotides of the present invention, which block RC3H1-A20/TNFAIP3 transcript interaction and subsequently increase A20/Tnfaip3 levels, providing a basis for medical use of the present oligonucleotides in the treatment of inflammation or medical conditions associated with inflammation.

The term "inflammation" or "medical condition associated with inflammation" as used herein relates to inflammation as understood by one skilled in the art. Typically, the term "inflammation" as used in its art-recognized sense relates to a localized or systemic protective response elicited by injury, infection or destruction of tissues which serves to protect the subject from an injurious agent and the injured tissue. Inflammation is preferably characterized by fenestration of the microvasculature, leakage of the elements of blood into the interstitial spaces, and migration of leukocytes into the inflamed tissue, which may lead to an uncontrolled sequence of pain, heat, redness, swelling, and loss of function.

Inflammation can be classified as either acute or chronic. Acute inflammation is the initial response of the body to harmful stimuli and is achieved by the increased movement of plasma and leukocytes (especially granulocytes) from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells present at the site of inflammation and is characterized by simultaneous destruction and healing of the tissue from the inflammatory process. Chronic inflammation, or expression of pro-inflammatory cytokines and receptors at low levels over long periods of time, promotes various pathological conditions including allergies and asthma, cardiovascular system disorders (atherosclerosis), central nervous system disorders (Alzheimer's disease), fibrosis, and rheumatoid arthritis. The majority of cytokines are inflammatory, including classes such as chemokines, interferons, and interleukins. These cytokines bind and activate their respective receptors to promote inflammatory responses. Examples of pro-inflammatory cytokines are Interleukin (IL)-1, tumor necrosis factor (TNF) alpha and Interferon (IFN) gamma.

According to one embodiment of the present invention, there is provided a method for treating one or more than one inflammation-related condition or disease. As used in this disclosure, "inflammation-related" in connection with "condition or disease" or "conditions and diseases" means "caused by the inappropriate initiation of inflammation or the inappropriate lack of cessation of inflammation" rather than merely associated with inflammation.

The method may comprise first identifying a patient with an inflammation-related condition or disease suitable for treatment by the present method. In one embodiment, identifying the patient comprises diagnosing the patient with one or more than one inflammation-related condition or disease suitable for treatment by the present method. In one embodiment, diagnosing the patient comprises performing one or more than one of action selected from the group consisting of performing a physical examination, performing a non-invasive imaging examination (such as for example computerized tomography, magnetic resonance imaging and ultrasound), and identifying one or more than one marker for the inflammation-related condition or disease in the blood or other body fluid of the patient. In another embodiment, identifying the patient comprises consulting patient records to determine if the patient has an inflammation-related condition or disease suitable for treatment by the present method.

With regard to the claimed medical use of the compounds, chronic inflammatory diseases, such as rheumatoid arthritis, inflammatory bowel disease, systemic lupus erythematosus, multiple sclerosis, and type-1 diabetes, among others, are of particular importance and affect more than 50 million individuals in North America alone. Many of these diseases are debilitating and are becoming increasingly common in an aging society. Further examples of disorders associated with inflammation include but are not limited to: Acne vulgaris, Allergies, Atherosclerosis, Asthma, Autoimmune diseases, Cancer, Celiac disease, Chronic prostatitis, Glomerulonephritis, Hypersensitivities, Inflammatory bowel diseases, myopathies, Pelvic inflammatory disease, Reperfusion injury, Rheumatoid arthritis, Sarcoidosis, Transplant rejection, Vasculitis and Interstitial cystitis.

TNFAIP3 has also been described previously as a tumour suppressor gene involved in negatively regulating Hodgkin lymphoma and B cell lymphoma. Proliferation and survival of Hodgkin and Reed/Sternberg (HRS) cells, the malignant cells of classical Hodgkin lymphoma, are dependent on constitutive activation of NF-κB. NF-κB activation through various stimuli is negatively regulated by the zinc finger protein A20. As disclosed in Schmitz et al (J Exp Med. 2009 May 11; 206(5):981-9) TNFAIP3/A20 is identified as a key regulator of NF-κB activity and as a novel tumour suppressor gene in classical Hodgkin lymphoma and primary mediastinal B cell lymphoma. In light of these associations the oligonucleotides of the present invention may be applied in the treatment of cancer, in particular lymphomas, more preferably Hodgkin lymphoma and B cell lymphoma. Lymphoma is a type of blood cancer that occurs when B or T lymphocytes, the white blood cells that form a part of the immune system, divide faster than normal cells or show an extended life span. Lymphoma may develop in the lymph nodes, spleen, bone marrow, blood or other organs and eventually form a tumor. Lymphomas may relate to AIDS-related, Lymphoma, Burkitt, cutaneous T-Cell, Hodgkin's, Non-Hodgkin's or a lymphoma of the Primary Central Nervous System.

TABLE 1b

The following sequences are encompassed by the present invention, for example as demonstrated in the figures and examples as described herein.

| | |
|---|---|
| ucyryga | SEQ ID NO: 16 |
| gcugggaaauacaaaggaa | SEQ ID NO: 17 |
| ccaagaaauguguagaaga | SEQ ID NO: 18 |
| tggacaaccagaaccacaaa | SEQ ID NO: 19 |
| gctgatccatttggtacatcac | SEQ ID NO: 20 |
| tgcacactgtgtttcatcgag | SEQ ID NO: 21 |
| acgctgtgggactgactttc | SEQ ID NO: 22 |
| ggagagcacgccatgaag | SEQ ID NO: 23 |
| aagattcgcatgcggtagag | SEQ ID NO: 24 |
| agccacatcgctcagacac | SEQ ID NO: 25 |
| gcccaatacgaccaaatcc | SEQ ID NO: 26 |
| gagtcagagttcacggagttc | SEQ ID NO: 27 |
| catgttctttcagcccctttg | SEQ ID NO: 28 |
| ggcctgtacatatataatataccctttacattatgtatgagggatttt | SEQ ID NO: 29 |
| tcgaaaaatccctcatacataatgtaagggtatattatatatgtaca | SEQ ID NO: 30 |
| ggcctgtacatatataatataccctttacataatctatcagcgatttt | SEQ ID NO: 31 |
| tcgaaaaatcgctgatagattatgtaagggtatattatatatgtaca | SEQ ID NO: 32 |
| ggcctgtacaaaaaaaaaaaaccctttacataatctatcagcgatttt | SEQ ID NO: 33 |
| tcgaaaaatcgctgatagattatgtaagggtttttttttttgtaca | SEQ ID NO: 34 |
| ggcctgtacaaaaaaaaaaaaccctttacattatgtatgagggatttt | SEQ ID NO: 35 |
| tcgaaaaatccctcatacataatgtaagggtttttttttttgtaca | SEQ ID NO: 36 |
| ggcctgtacatgtacgatctgcccttacattatgtatgagggatttt | SEQ ID NO: 37 |
| tcgaaaaatccctcatacataatgtaagggcagatcgtacatgtaca | SEQ ID NO: 38 |
| ggcctgtacatgtacgatctgcccttacataatctatcagcgatttt | SEQ ID NO: 39 |
| tcgaaaaatcgctgatagattatgtaagggcagatcgtacatgtaca | SEQ ID NO: 40 |

TABLE 1b-continued

The following sequences are encompassed by the present invention, for example as demonstrated in the figures and examples as described herein.

SEQ ID NO: 41
ggcctgtacatgtacgatctgcccttacaaaatctatgagggatttt

SEQ ID NO: 42
tcgaaaaatccctcatagattttgtaagggcagatcgtacatgtaca

SEQ ID NO: 43
auuucugugaaau

SEQ ID NO: 44
tcgtatgccgtcttctgcttg

SEQ ID NO: 45
tctcgtatcgtatgccgtcttctgcttg

SEQ ID NO: 46
tctctgctcgtatgccgtcttctgcttg

SEQ ID NO: 47
rgrurucrargrargrururcrurarcrargrurcrcrgrarcrgraru
rc

SEQ ID NO: 48
uuuuuaa

SEQ ID NO: 49
uuuuaaa

SEQ ID NO: 50
uuuauuu

SEQ ID NO: 51
uuauuuu

SEQ ID NO: 52
uuuucuu

SEQ ID NO: 53
uauuuau

SEQ ID NO: 54
cugaacc

SEQ ID NO: 55
gguauau

SEQ ID NO: 56
uuuuguu

SEQ ID NO: 57
uuuaaaa

SEQ ID NO: 58
uuuuuua

SEQ ID NO: 59
uuuuuuu

SEQ ID NO: 60
auuuuuu

SEQ ID NO: 61
uauuuuu

SEQ ID NO: 62
aaauuuu

SEQ ID NO: 63
aauuuuu

SEQ ID NO: 64
uuuuauu

SEQ ID NO: 65
auuuuaa

SEQ ID NO: 66
auuuuau

SEQ ID NO: 67
tacatatataatataccctta cattatgtatgagggatttttttaaatta
tattgaaat

SEQ ID NO: 68
acuuacuacuugaaacuuuauuuauugcaccauguuggugu

SEQ ID NO: 69
aacauacuaacauuucuccuuuggaggaaguuuuaaucuac

SEQ ID NO: 70
gaggagggagaaguggga aguagcuugggaacugguuuguc

SEQ ID NO: 71
guaaaauaagcauuuggaagucuugggaggccugccugcua

SEQ ID NO: 72
ugugcaacacaggauuauuuuuaaaugauucugaauuugaa

SEQ ID NO: 73
gguuuacuauacaucagcauuuugcuguguugcaucuagaa

SEQ ID NO: 74
uucuagauacuuaaaaggcuuuugccuugcacaaaguaua

SEQ ID NO: 75
uauacacauacuuacauacuuauaugggu aucuguauagau

SEQ ID NO: 76
auauauaauauaccc uuacauuauguaugagggauuuuuuu

FIGURES

FIG. 1 PAR-CLIP identifies thousands of human mRNAs directly bound by RC3H1

(a) Phosphorimage of SDS-PAGE of radiolabeled FLAG/HA-RC3H1-RNA complexes from 365 nm UV crosslinked non-labeled, 6SG or 4SU-labeled cells. Crosslinked protein-RNA complexes were observed upon metabolic labeling with 4SU or 6SG. The lower panel shows an anti-HA Western blot, confirming correct size and equal loading of the IPed protein.

(b) Alignment statistics of PAR-CLIP reads prepared from 4SU-1 library. Sense mapping is shown above and antisense is shown below the horizontal axis. T to C transitions indicate cloning of crosslinked RNA fragments.

(c) A Venn diagram showing the overlap of target mRNA transcripts between PAR-CLIP experiments.

(d) Distribution of binding sites along mRNA transcripts based on consensus RC3H1 PAR-CLIP binding sites. The majority of binding sites are located in 3'UTR.

Figure 2:
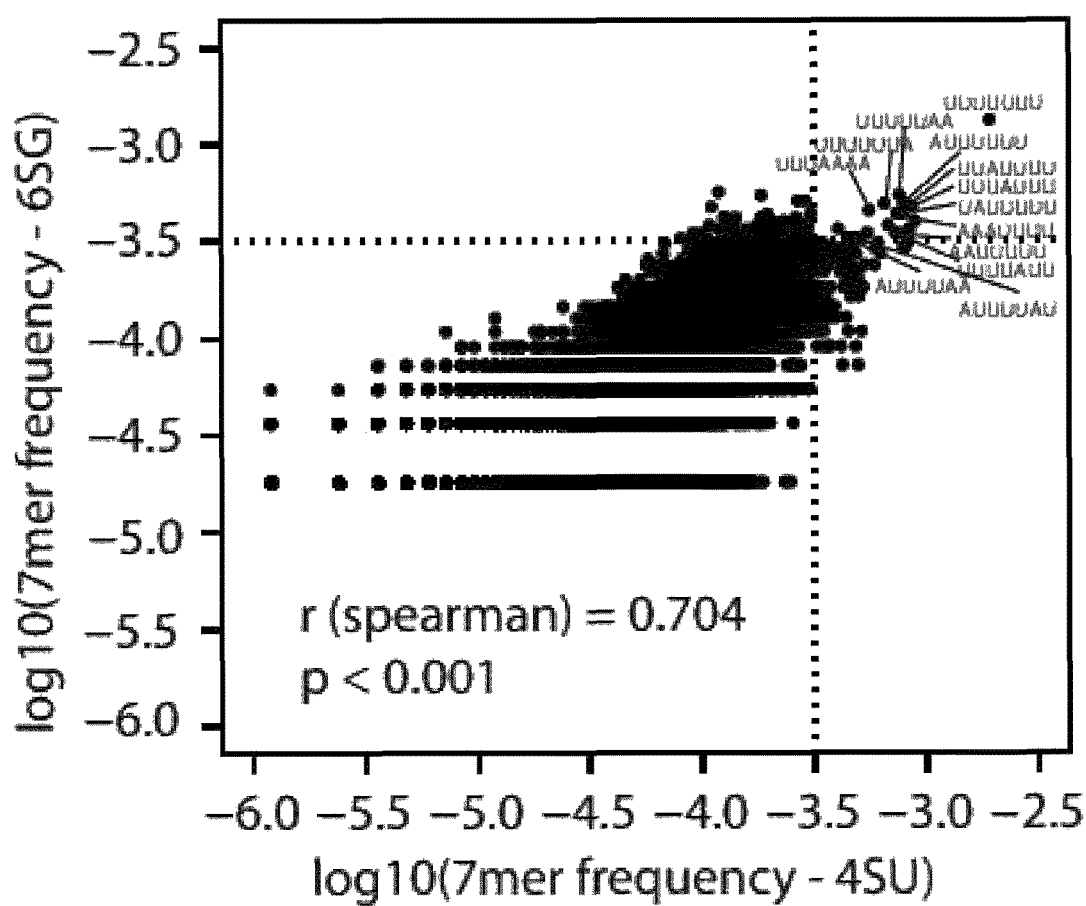
Figure 2:
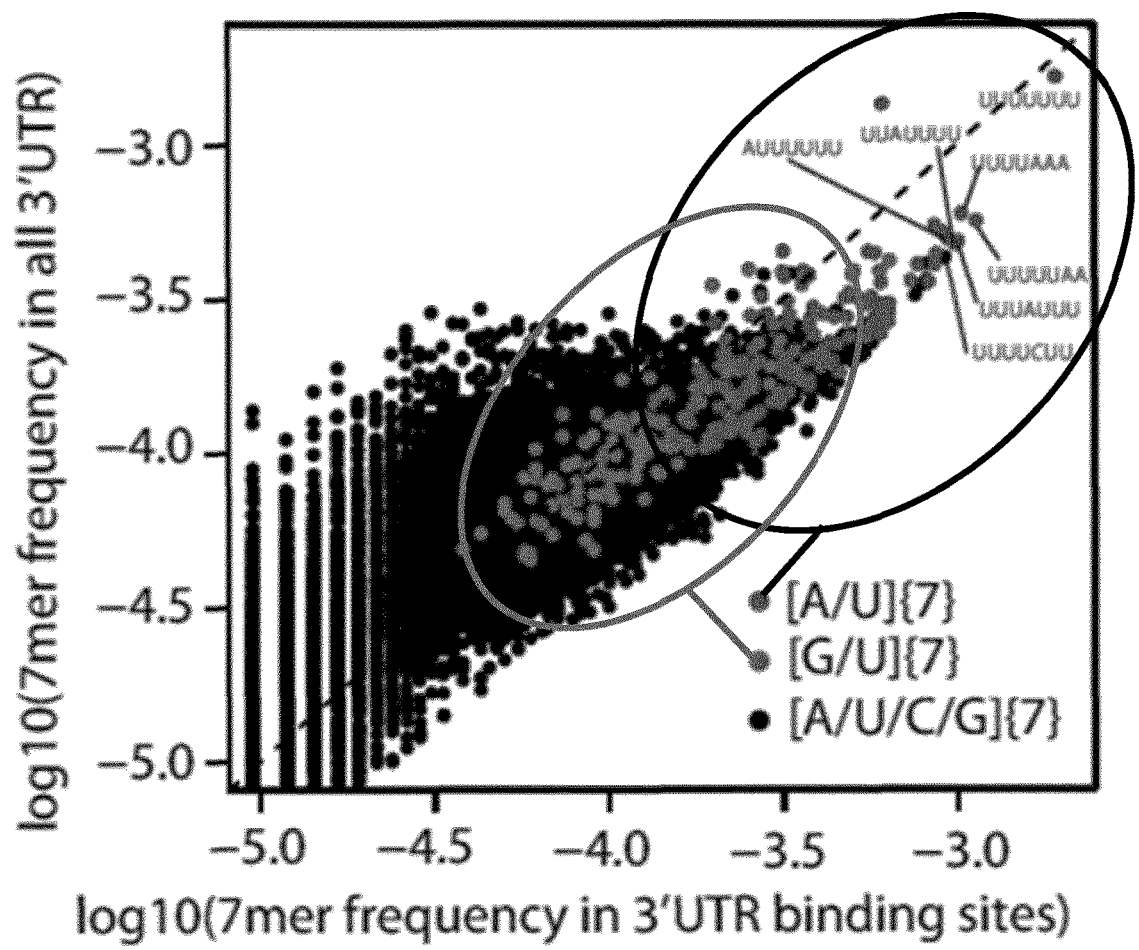
Figure 2:
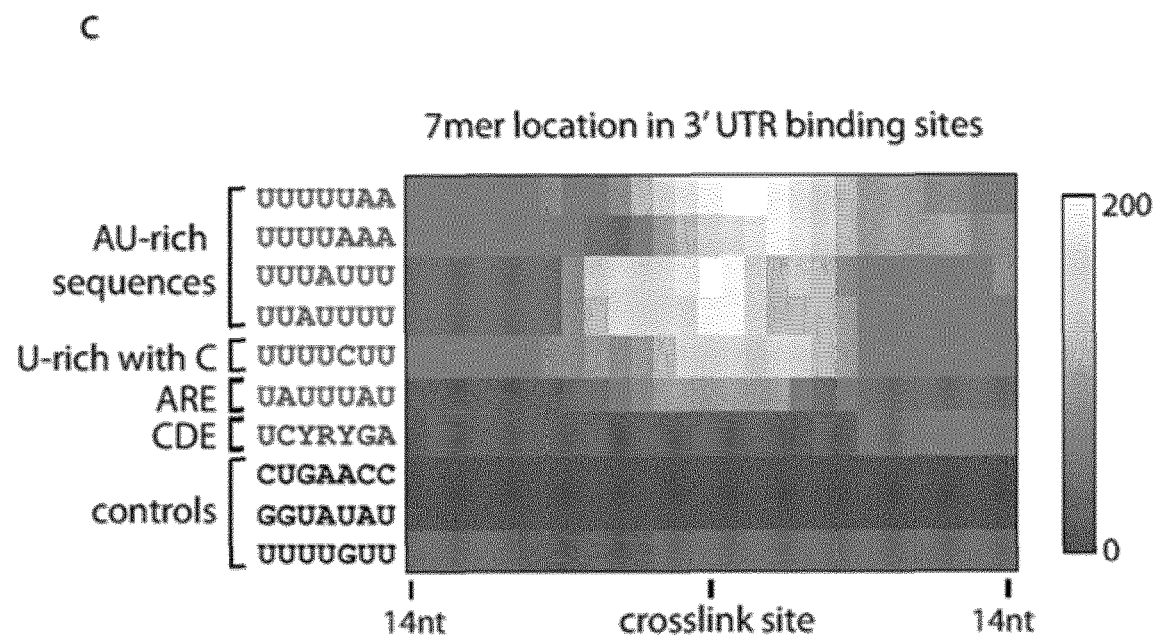
Figure 2:
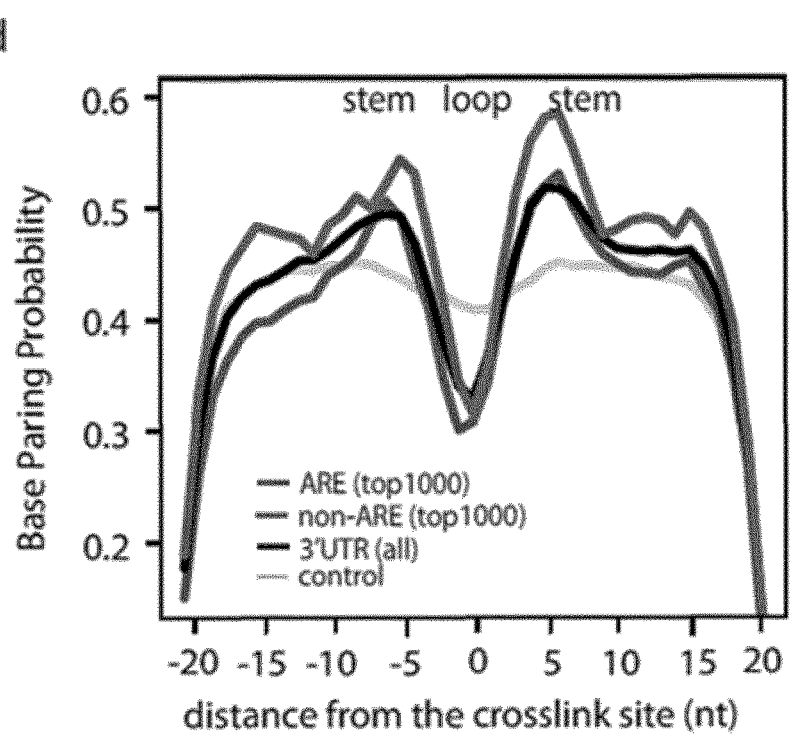

FIG. 2 Identification of AU-rich sequences and stem-loop secondary structure as recognition elements of RC3H1.

(a) log 10 frequencies of 7mers occurring in the 41 nt window around the RC3H1 preferred crosslink sites are shown for 4SU-2 and 6SG experiments. AU-rich sequences are frequently occurring in both 4SU and 6SG experiments.

(b) A scatter plot showing 7mers log 10 frequencies in the 41 nt window around the preferred crosslink sites of consensus 3'UTR RC3H1 binding sites versus 7mers log 10 frequencies in all 3'UTR sequences. 7mers comprising only A/U or G/U are plotted in the upper and lower circles, respectively. AU-rich sequences (upper) are more frequent and enriched over the background frequency whereas control 7mers made up of G/U are not.

(c) A heatmap showing the coverage of 7mers, indicated on the left, around the preferred crosslinks in 3'UTR RC3H1 consensus binding sites. AU-rich elements (AREs) and conserved decay element (CDE) are indicated. U-rich sequences are found in the close vicinity of crosslink sites, which is indicative of direct association of RC3H1 with U-rich sequences.

(d) RC3H1 binding sites tend to have stem-loop secondary structure. 41 nt sequences centered around RC3H1 crosslink site were computationally folded. Base pairing probability for each position around crosslink sites are averaged over top 1000 AU-rich sequences containing 3'UTR binding sites, top 1000 AU-rich sequences non-containing 3'UTR binding sites, all 3'UTR binding site and control 3'UTR sequences.

Figure 3:
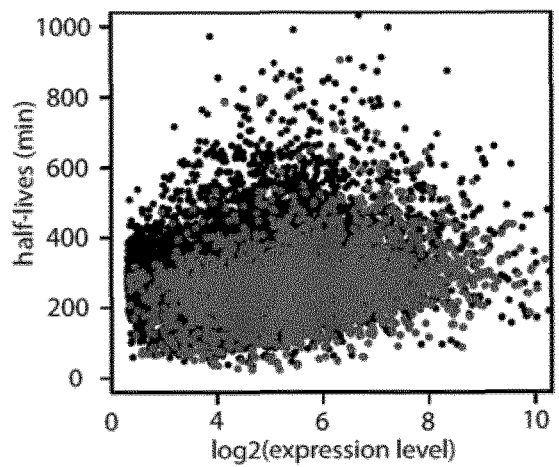
Figure 3:
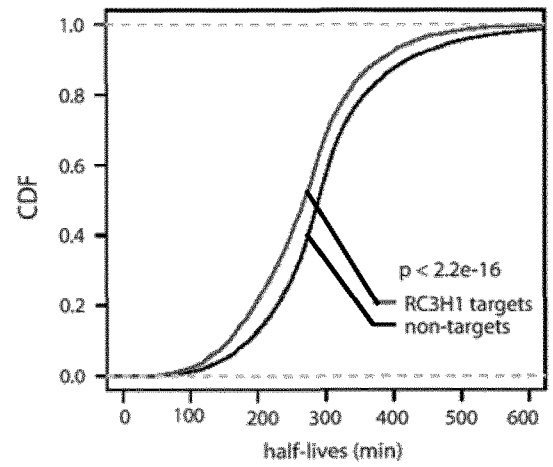
Figure 3:
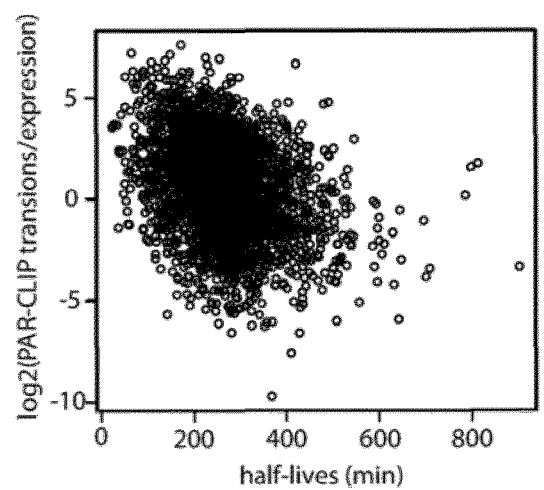
Figure 3:
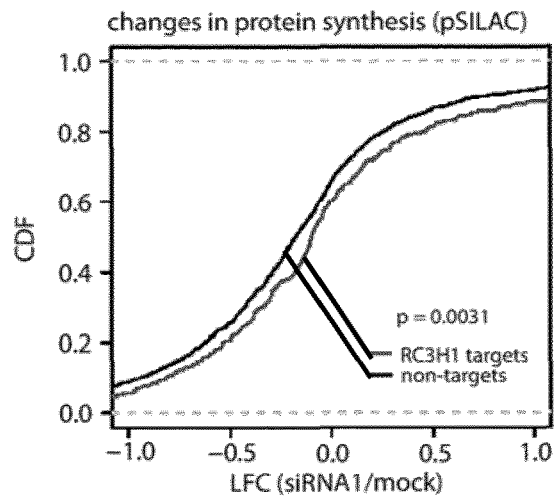

FIG. 3 RC3H1 target transcripts have shorter half-lives.

(a) RC3H1 target transcripts have shorter half-lives. Gray or black dots represent the 3'UTR RC3H1 consensus targets or non-targets, respectively. log 2 expression levels and half-lives (min) are blotted on x- and y-axis, respectively.

(b) A cumulative distribution function (CDF) plot of half-lives shown in (c). The mean half-lives of RC3H1 targets and non-targets are 269.9 min and 311.1 min, respectively. The difference is significant with p-value smaller than 2.2e−16 (Wilcoxon's rank sum test).

(c) Inverse correlation (Spearman r coefficient −0.33, p value <2.2e−16) between mRNA half-live against PAR-CLIP index, defined by number of RC3H1 PAR-CLIP transitions normalized for expression level for each gene.

(d) A CDF plot of log 2-fold changes of protein synthesis of consensus RC3H1 target transcripts that have more than 100 transitions on 3'UTR after siRNA-mediated RC3H1 depletion. Protein synthesis of RC3H1-bound mRNAs was significantly up-regulated upon RC3H1 knockdown (p-value 0.0031, Wilcoxon's rank sum test). The mean log 2 fold changes of RC3H1 targets (n=390) and non-targets (n=1279) are 0.001 and −0.116, respectively.

Figure 4:
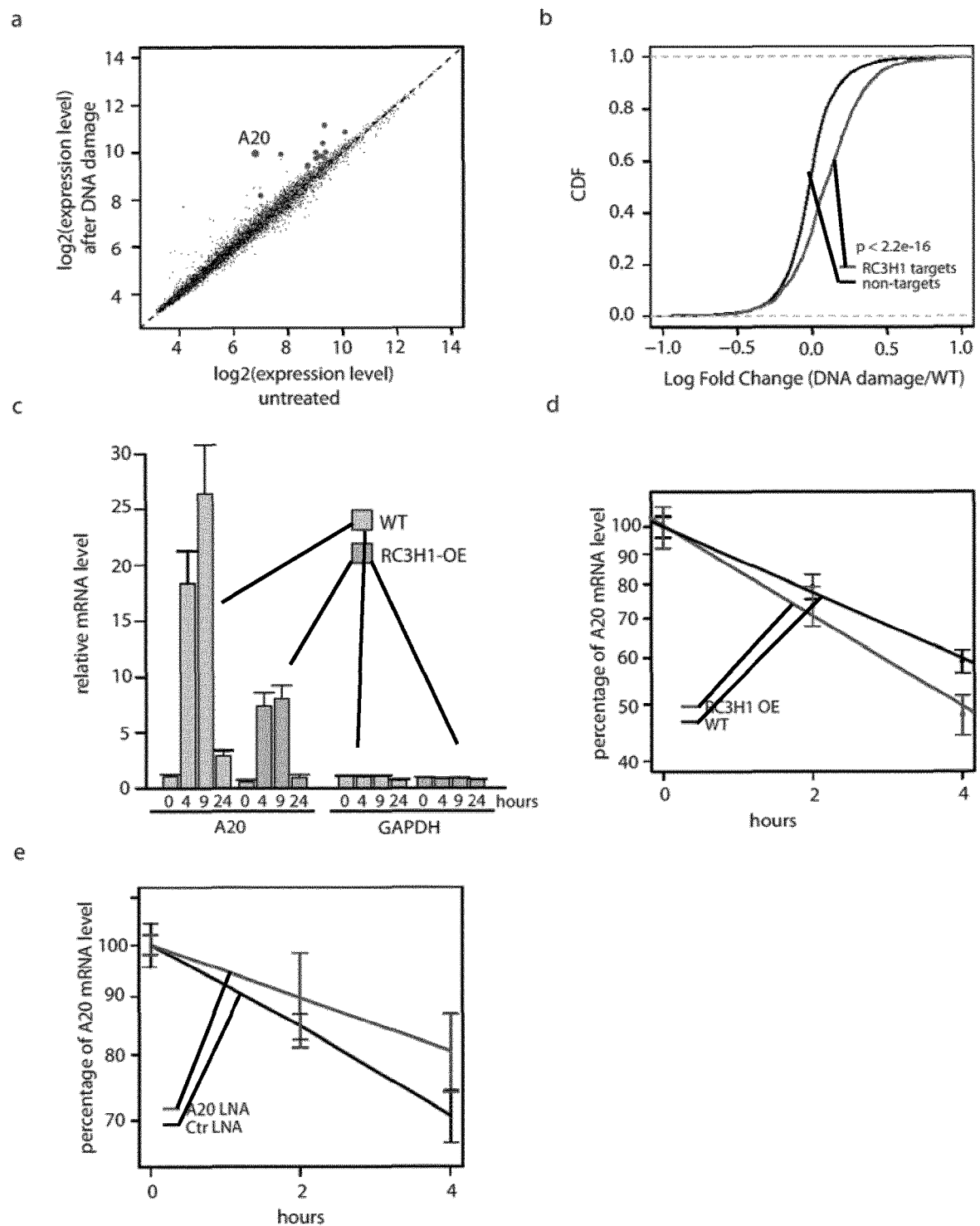

FIG. 4 RC3H1 target transcripts are enriched for mRNAs induced upon DNA damage, and RC3H1 negatively regulates A20 at the posttranscriptional level.

(a) A scatter plot of mRNA expression levels of untreated cells and cells treated for 4 hours with 200 ng/ml of NCS (data derived from[29]). RC3H1 3'UTR target transcripts are shown in grey and non-targets are shown in black. Among the RC3H1 targets, A20 was the most differentially expressed mRNA upon DNA damage.

(b) A CDF plot of log 2 fold changes upon DNA damage is shown for RC3H1 3'UTR targets in grey and for non-targets in black. The difference is significant with p-value smaller than 2.2e−16 (Wilcoxon's rank sum test).

(c) RC3H1 overexpression specifically leads to reduced expression of A20 at each time point. mRNA expression level of A20 and GAPDH (negative control) are measured by qPCR at 0, 4, 9 and 24 hours post DNA damage induced by 250 ng/ml of NCS. Average and standard deviation (error bar) from three technical replicates are shown. A representative data from two independent biological replicates are shown.

(d) Overexpression of RC3H1 leads to shorter half-life of A20 mRNA. At 4 hours post DNA damage induced by NCS (250 ng/ml), transcription was blocked with actinomycin D and mRNA decay was measure by qRT-PCR. Percentage of A20 mRNA amount at each time point relative to starting point is shown. Error bars indicate standard deviations calculated from three replicates.

(e) Transfection of antisense LNA oligonucleotide targeting the stem-loop structure in HEK293 cells leads to specific increase in A20 mRNA half-life (grey) in comparison to control LNA transfection (black). Representative data from two independent experiments are shown.

Figure 5:
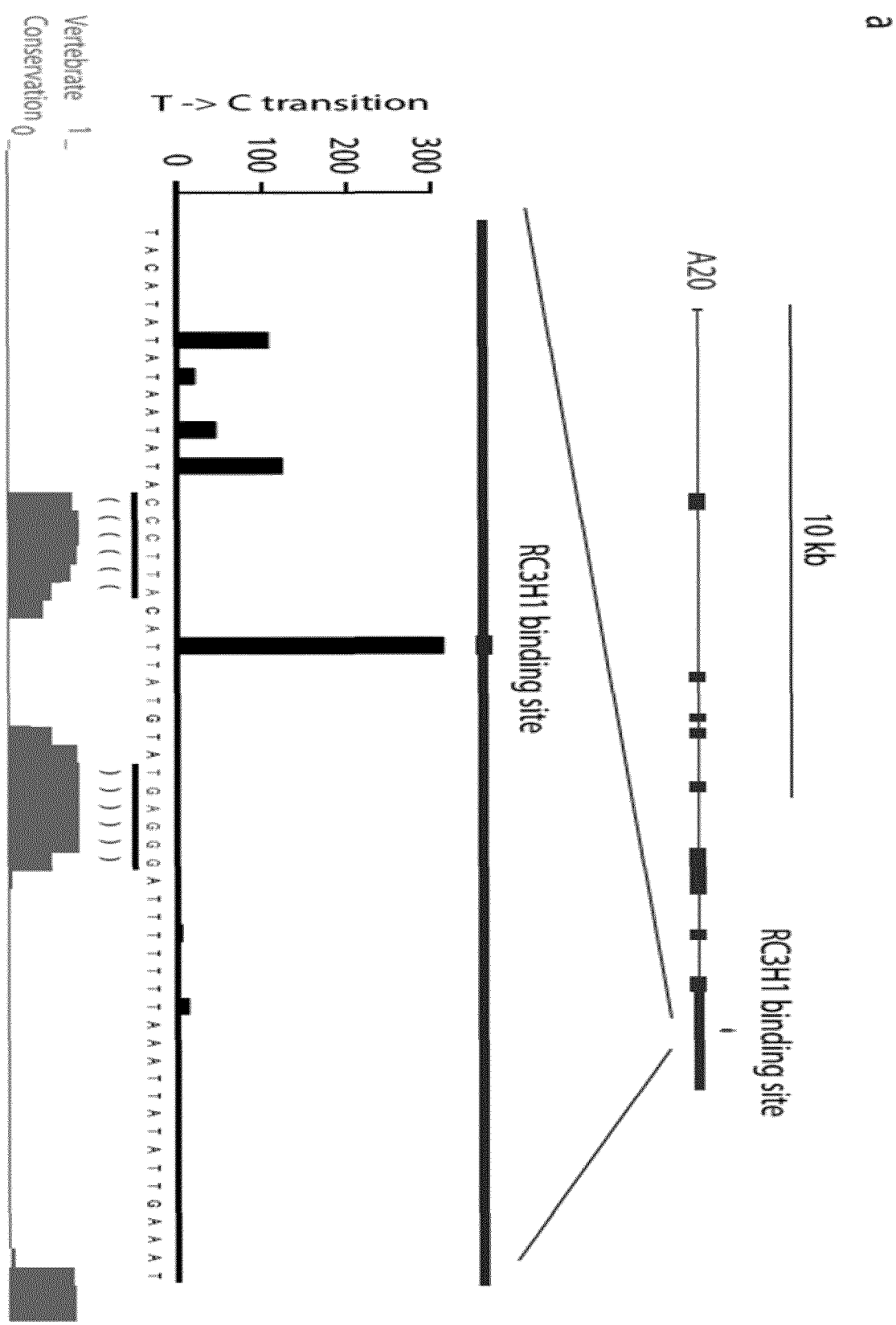
Figure 5:
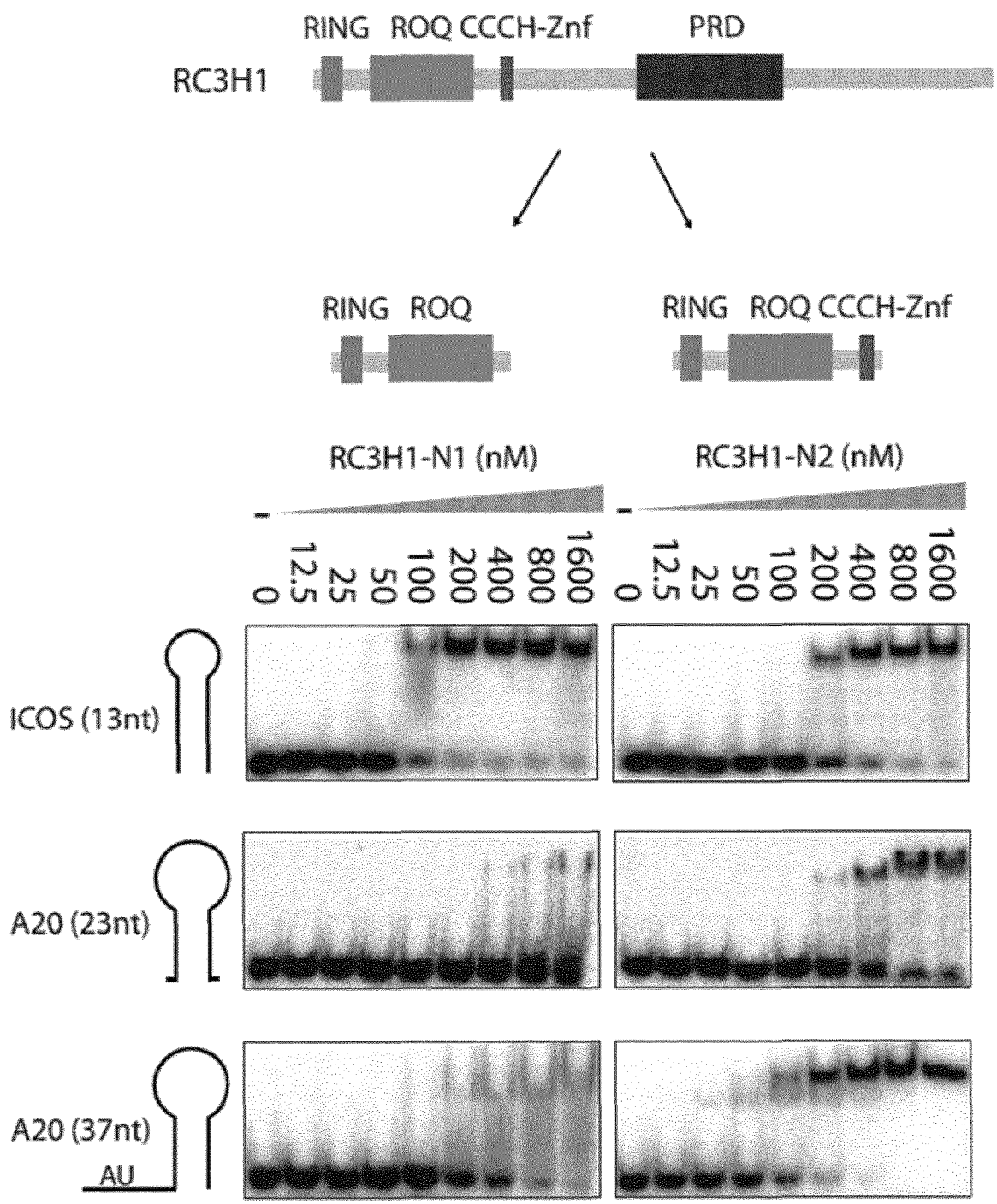
Figure 5:
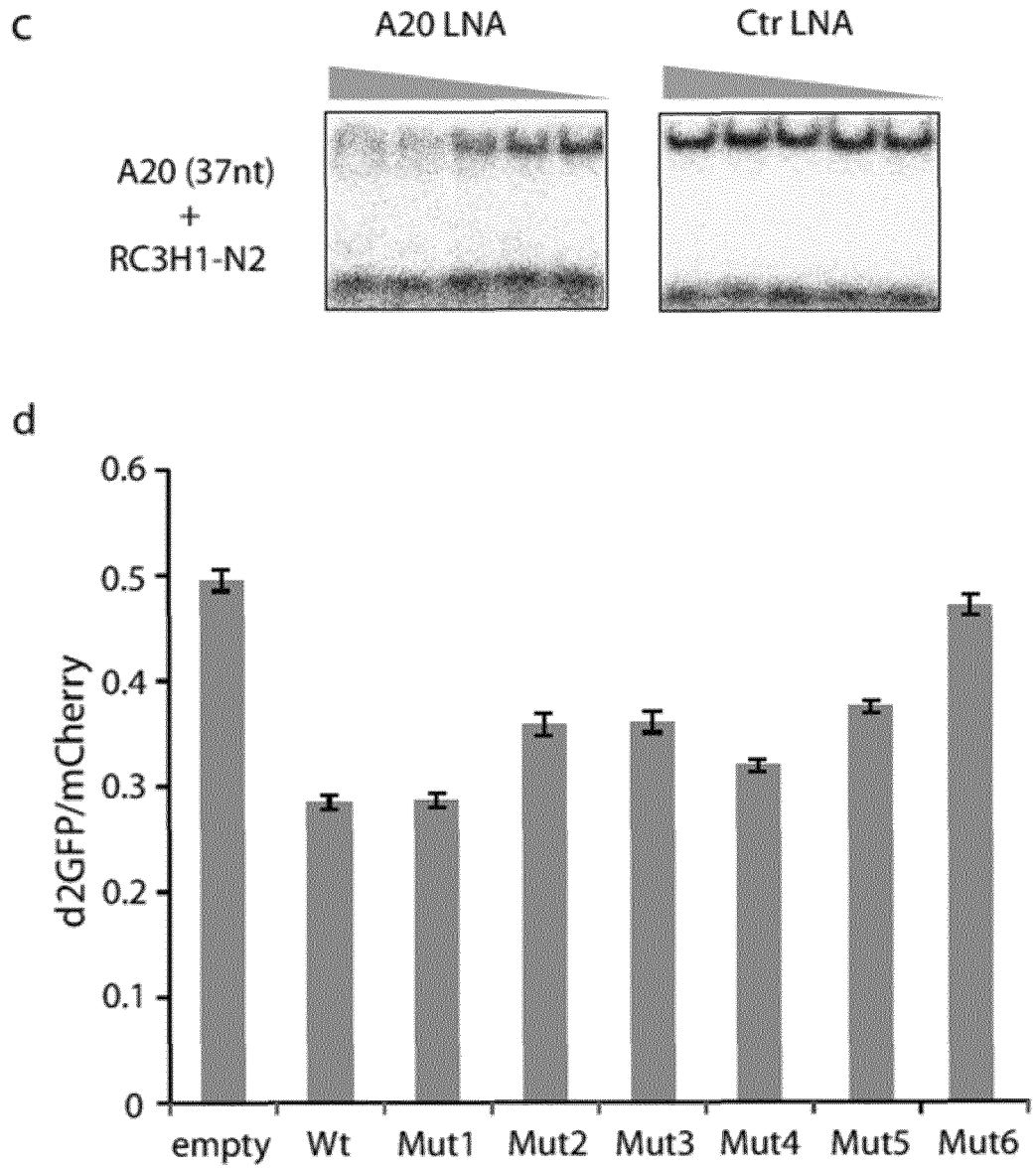
Figure 5:
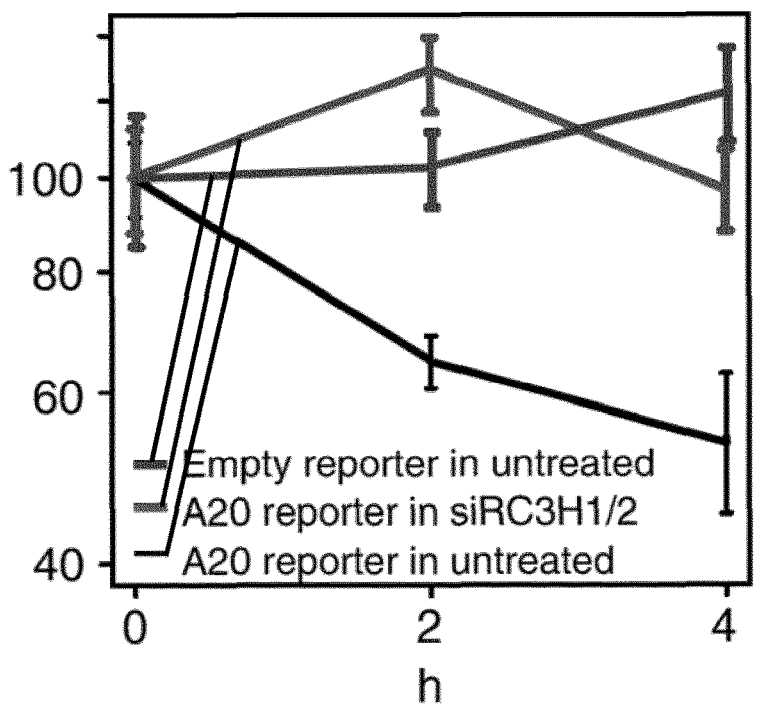

FIG. 5 RC3H1 binds to a composite structure-sequence motif in the 3'UTR of A20 mediated by the CCCH-type zinc finger domain.

(a) Illustration of the RC3H1 binding site in the A20 3'UTR. The binding sites of RC3H1 binding site in the 3'UTR of TNFAIP3 is shown and zoomed in below. Number of T to C transitions for indicated base positions are shown. Bases shown in underline are forming stem. Phastcon vertebrate conservation is shown underneath the underline.

(b) Electrophoreic mobility shift assay (EMSA) experiments to examine the binding mode of RC3H1 to the A20 target site. Increasing concentration of recombinant RC3H1-N1 (amino acids 2-399) or RC3H1-N2 containing additional CCCH-type zinc finger domain (amino acids 2-452) was incubated with radiolabeled ICOS (13 nt), A20 stem-loop (23 nt), and A20 ARE-stem-loop (37 nt), and free RNA was separated from RNA-protein complexes by native PAGE.

(c) Increasing concentration of antisense LNA oligonucleotide targeting the A20 stem-loop structure impairs the interaction of RC3H1-N2 and ARE-stem-loop (37 nt).

(d) The effect of different elements in the A20 ARE-stem-loop sequence was assayed by transiently transfecting HEK293 cells with the d2GFP reporter plasmid containing the RC3H1 binding site in the A20 3'UTR and variants thereof. Mean Fluorescence Intensity (MFI) of d2GFP obtained by flow cytometry was normalized against MFI of mCherry, which was used as transfection control. Wild-type (Wt) contains 37 nt A20 ARE-stem-loop sequence inserted into the 3'UTR of d2GFP, and each variant (Mut1-6) carries mutations. Average and standard deviation (error bar) from 3 biological replicates are shown.

(e) The effect of A20 AU-rich element (ARE)-stem-loop hairpin (37 nucleotide (nt)) was assayed by transiently transfecting HEK293 cells with the d2GFP reporter plasmid, which contains the 37-nt sequence inserted into the 30 UTR of d2GFP. mRNA decay of the reporter transcripts were measured in mock and RC3H1/RC3H2 knockdown cells. Average and s.d.'s (error bar) from three technical replicates are shown.

Figure 6:
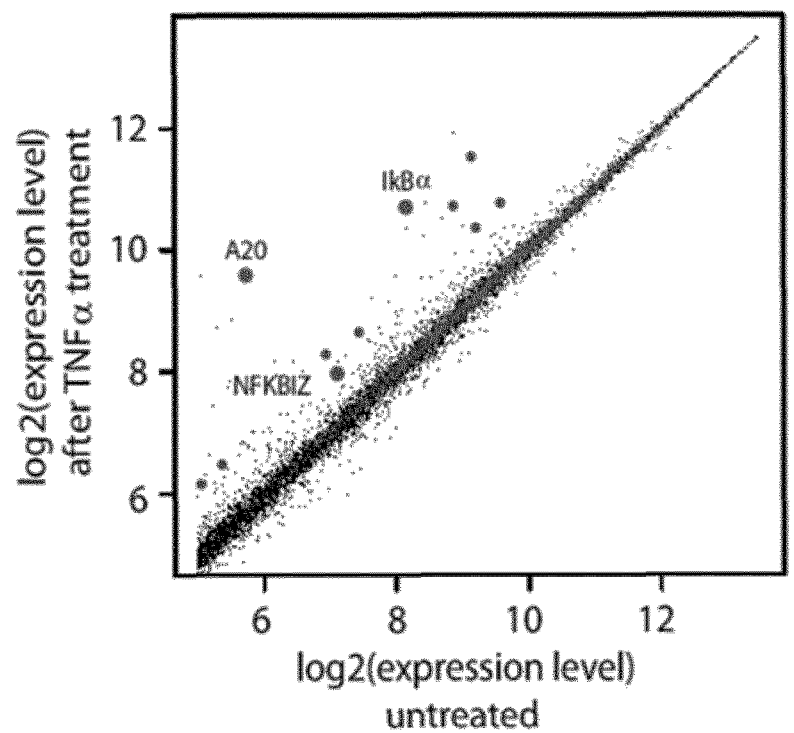
Figure 6:
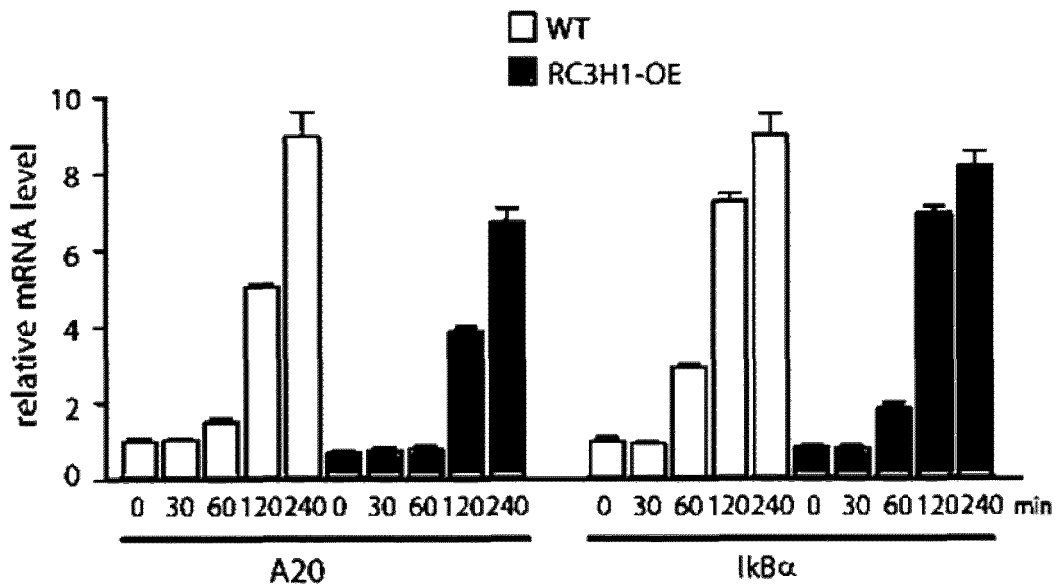
Figure 6:
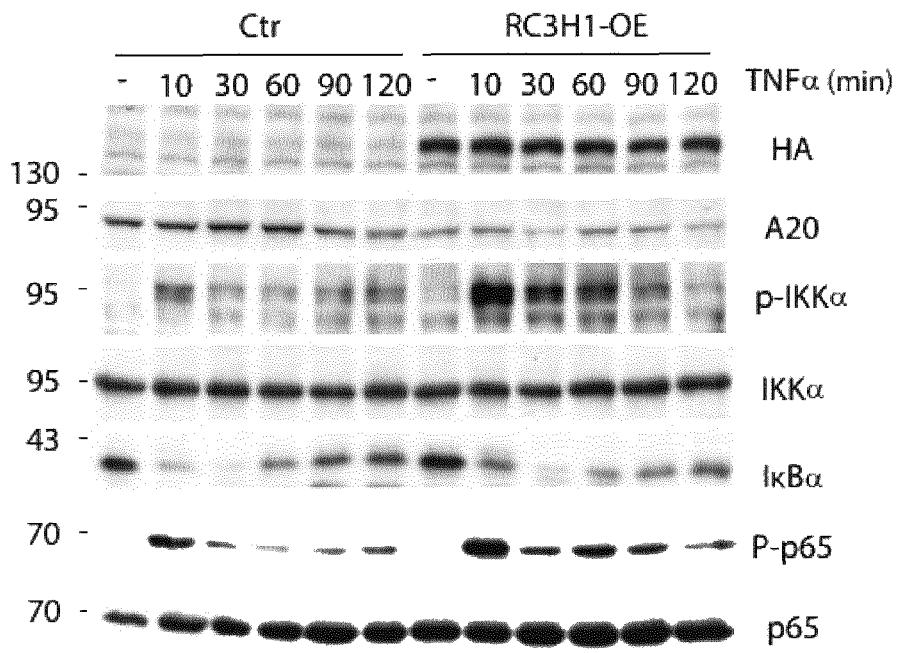
Figure 6:
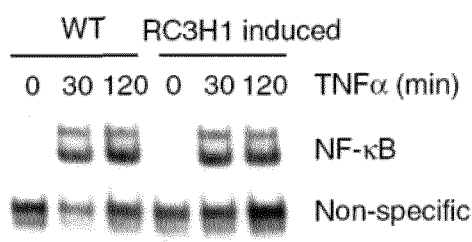
Figure 6:
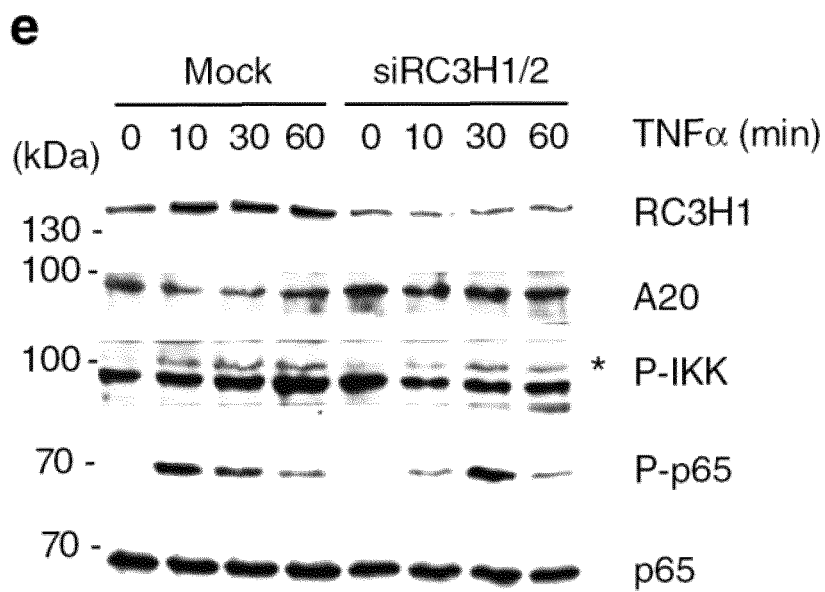
Figure 6:
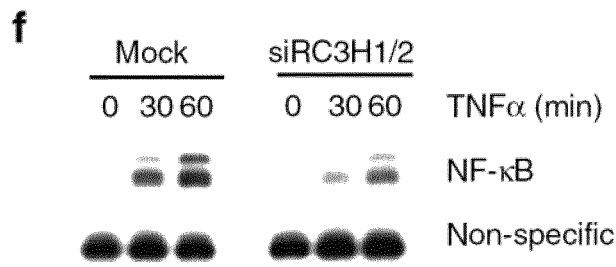

FIG. 6 RC3H1 modulates the activation of IKK by TNFα.

(a) A scatter plot of mRNA expression levels of untreated cells and cells treated for 4 hours with 10 ng/ml of TNFalpha (data is derived from [35]). RC3H1 3'UTR target transcripts are shown in grey and non-targets are shown in black. Several TNFalpha-induced mRNAs, such as A20, IkBalpha and NFKBIZ are targets of RC3H1. Amongst the RC3H1 target transcripts, A20 was the most differentially expressed mRNA upon TNFalpha treatment.

(b) RC3H1 overexpression leads to reduced expression of A20 at each time point. mRNA expression levels of A20 and IkBalpha were measured by qPCR at indicated time points after TNFalpha treatment. Representative data from two independent experiments are shown. Average and standard error of the mean (error bar) are from three technical replicates.

(c) Western blot analyses of NF-kB pathway proteins after TNFα stimulation in cells with DOX-dependent RC3H1 expression. 293 cells were treated with Doxycycline (1 μg/ml; 24 h), to induce HA-RC3H1. Subsequently, cells were treated with TNFα as indicated, lysed and analyzed by Western-blotting with the indicated antibodies. RC3H1-upregulation results in decreased A20 expression, increased IKK activation (T-loop phosphorylation, P-IKK) and phosphorylation of p65 (P-p65). Representative data from two independent experiments are shown.

(d) EMSA analysis of whole-cell extracts for TNFa-induced NF-kB activity. Cells were treated as in c.

(e) Western blot analyses of the NF-kB pathway proteins after TNFa stimulation in mock or RC3H1/2 siRNA-treated HEK293. Cells were treated with TNFa, and analysed by western blot with the indicated antibodies. RC3H1 down-regulation results in mildly increased A20 expression, leading to decreased IKK activation and phosphorylation of p65. Representative data from two independent experiments are shown. '*' indicates phosphorylated form of IKK.

(f) EMSA analysis of whole-cell extracts for TNFα-induced NF-kB activity. Cells were treated as in e. Knockdown of RC3H1 expression reduced the NF-kB activity.

FIG. 7

(a) Western blot analyses for RC3H1, FLAG/HA-RC3H1, and TUBULIN in the presence and absence of doxycycline (1 μg/ml for 9 hours). RC3H1 signal was quantified and normalized for TUBLIN loading control. A bar plot shows relative normalized expression of RC3H1.

(b) Alignment statistics of PAR-CLIP reads prepared from 4SU-2 library. Sense mapping is shown in blue and antisense is shown in red. T to C transitions are prominent and diagnostic for efficient crosslinking.

(c) Alignment statistics of PAR-CLIP reads prepared from 6SG library, as shown in (a).

(d) A length histogram of clusters identified in 4SU-1, 4SU-2, 6SG or consensus PAR-CLIP. RC3H1 PAR-CLIP clusters are typically small with the median cluster length of around 25 to 30 nt.

(e) Top 1000 "consensus set" target genes, ranked by the number of transitions in the 3'UTR, were subjected to enrichment analysis for the KEGG pathway using the on-line DAVID program. The top 10 KEGG pathways are shown. The number of genes falling into each pathway and p-values corrected for multiple comparison by the Benjamini-Hochberg are shown in "count" and "Benjamini" column, respectively.

(f) Mouse RC3H1 target mRNAs identified by Leppek and colleagues are compared to human PAR-CLIP RC3H1 target mRNAs. Out of 95 genes, 91 genes are converted to orthologous human genes, and divided into two groups based on FPKM expression value in HEK293 cells. For each group, number of mRNAs that are overlapping in human PAR-CLIP RC3H1 target mRNAs is shown. Number of mouse CDE containing mRNAs is shown in parentheses.

(g) Distribution of consensus RC3H1 binding cluster along 3'UTRs of mRNA.

(h) Density of predicted conserved miRNA target sites around crosslink sites in 3'UTRs. RC3H1 crosslink sites and miRNA target sites display no tendency for direct overlap but the larger context (10-50 nt) shows mildly elevated seed density. The gray envelope represents the standard error of the mean. RC3H1 target sites identified in 4SU-1 is used in this analysis.

FIG. 8

(a) A RNA structure dot plot for top 1000 RC3H1 consensus targets, ranked by number of T to C transition events in 3'UTR (top right triangular), and control sets of random 3'UTR sequence from RC3H1 target genes (bottom left triangular) demonstrates the stem-loop structure of RC3H1 binding sites. A dot placed in the ith row and jth column of a triangular array represents the base pair between the ith base with jth base, and the size of dot is proportional to the square root of average base paring probability for each base paring.

(b) The 41 nt windows around the preferred crosslink sites for top 10 RC3H1 3' UTR binding sites (ranking is based on PAR-CLIP transition events normalized for expression levels) are in silico folded using the on-line mfold program[53], and the predicted RNA secondary structures are drawn using jViz.RNA 2.0[54].

FIG. 9

(a) Overview of the pSILAC experiment. pSILAC measures changes in protein synthesis. Cellular proteins incorporate either heavy (mock) or medium-heavy (RC3H1 knockdown) amino acids for 24 h. The mass shift allows measurement of the difference in newly synthesized protein between normal and RC3H1 depleted cells.

(b) Western Blot analyses for endogenous RC3H1 knockdown mediated by two distinct siRNAs (siRNA-1 and siRNA-2) against RC3H1 and for TUBULIN as a loading control.

(c) A scatter plot of log 2 fold changes of protein synthesis after siRNA-1 (FIG. 4f) mediated knockdown versus siRNA-2 mediated knockdown. Grey and black dots indicate the PAR-CLIP targets (consensus set) and non-targets, respectively (upper right).

(d) A CDF plot of log 2 fold changes of protein synthesis of consensus RC3H1 targets that have more than 100 transitions on 3'UTR (1561 genes) shown in grey and non-targets shown in black after siRNA-2 mediated knockdown. Protein synthesis of RC3H1 targets is mildly but significantly increased upon RC3H1 knockdown (p-value 0.00015, Wilcoxon's rank sum test). The mean log 2 fold changes of RC3H1 targets (n=390) and non-targets (n=1307) are 0.089 and −0.023, respectively.

FIG. 10

(a) Western blot analyses for FLAG/HA-RC3H1, gammaH2AX (a marker for DNA damage), and vinculin (loading control). Samples are harvested at indicated time points following NCS induced DNA damage. Increased gammaH2AX indicates the proper induction of DNA damage.

(b) A CDF plot of log 2 fold changes upon TNFα treatment (FIG. 6a) is shown for RC3H1 3'UTR targets in grey and for non-targets in black. The mean log 2 fold changes of RC3H1 targets (n=3184) and non-targets (n=10142) are 0.0160 and −0.0146, respectively. The difference is significant with p-value of 0.00015 (Wilcoxon's rank sum test).

EXAMPLES

The invention is further described by the following examples. These are not intended to limit the scope of the invention.

PAR-CLIP Identifies Thousands of Human mRNAs Directly Bound by RC3H1

To identify RC3H1 binding sites at high resolution, we applied photoactivatable-ribonucleoside-enhanced cross-linking and immunoprecipitation (PAR-CLIP) in combination with next-generation sequencing[17]. In PAR-CLIP experiments, nascent RNA is metabolically labeled with the non-perturbing photoreactive ribonucleosides 4-thiouridine (4SU) or 6-thioguanosine (6SG). Crosslinking of protein to 4SU- or 6SG-labeled RNA leads to specific T to C or G to A transitions, respectively, that occur at high-frequency in cDNA sequence reads and mark the protein crosslinking sites on the target RNA[17]. HEK293 cells stably expressing inducible FLAG/HA-tagged RC3H1 (FIG. 7a) were crosslinked after labeling of RNA with either 4SU or 6SG. Immunopurified, ribonuclease-treated and radiolabeled RC3H1-RNA complexes were separated by SDS-PAGE (FIG. 1a). Protein-protected RNA fragments were recovered and converted into a cDNA library amenable to Illumina sequencing.

Figure 7:
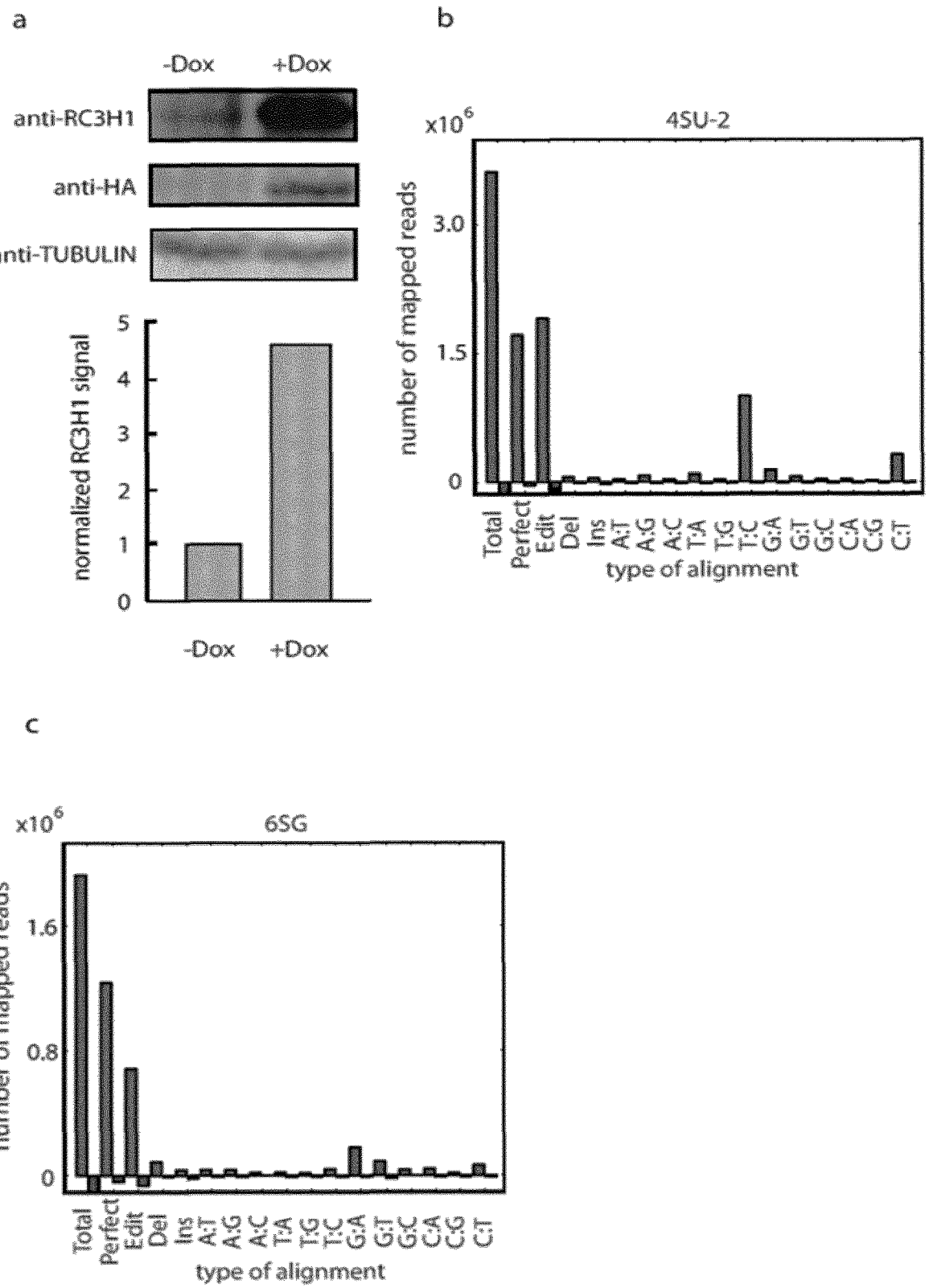
Figure 7:
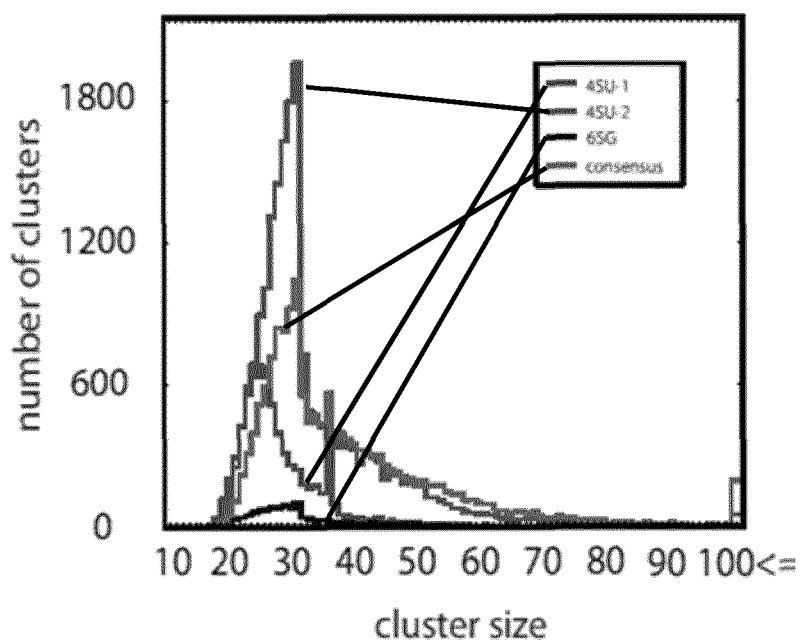
Figure 7:
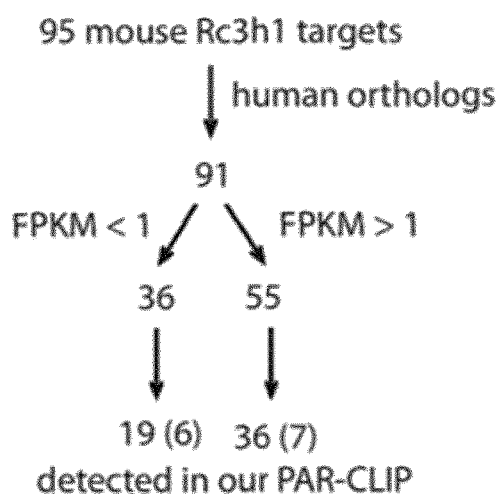
Figure 7:
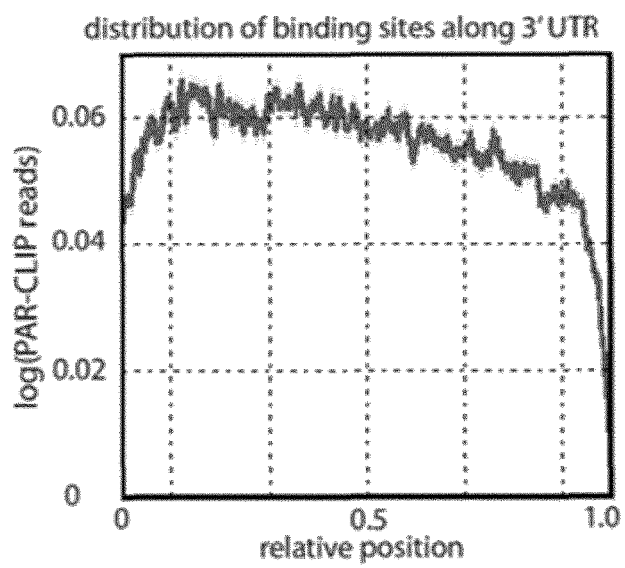
Figure 7:
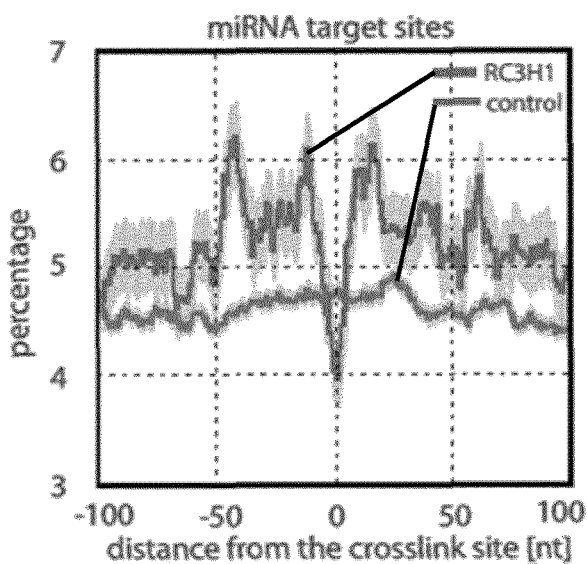

In total we performed three independent PAR-CLIP experiments (two biological replicates with 4SU and one replicate with 6SG). Sequence reads were mapped to the human genome and overlapping reads were used to build RC3H1 binding clusters[20]. In PAR-CLIP experiments using 4SU, diagnostic T to C transitions detected in mapped reads were most highly abundant (FIG. 1b and FIG. 7b). Similarly, but less pronounced, the diagnostic G to A mutation was the most abundant type of mutation for 6SG PAR-CLIP experiments (FIG. 7c). A length histogram of RC3H1 PAR-CLIP clusters shows a median cluster size of around 25 to 30 nt (FIG. 7d).

We identified about 2000 to 4000 RC3H1 mRNA target transcripts in each of the 4SU PAR-CLIP experiments (FIG. 1c). Ninety-three percent of the 481 6SG PAR-CLIP mRNA targets were reproduced in 4SU libraries (FIG. 1c). We combined the reads from all PAR-CLIP experiments to derive a set of consensus binding sites supported by reads from at least two out of three experiments (see Online Methods). Based on this analysis, we identified 16234 RC3H1 binding sites on 3821 protein-coding transcripts as consensus data sets. The position with the highest number of PAR-CLIP derived diagnostic nucleotide transitions for each binding sites was referred to as the preferred crosslinking site.

To gain an insight into the transcripts regulated by RC3H1, genes encoding RC3H1-bound mRNAs were subjected to KEGG pathway and GO term enrichment analysis[22,23]. Interestingly, cell cycle and p53 signaling pathway were overrepresented in the KEGG pathway enrichment analysis (FIG. 7e), suggesting that RC3H1 could play a role in the response to DNA damage. Furthermore, GO term enrichment analysis showed that RC3H1-bound transcripts are highly enriched for regulators of gene expression such as transcription factors, RNA-binding proteins and ubiquitin ligases. In addition, when comparing the human RC3H1 targets with mouse Roquin-bound transcripts[8], we identified 36 of 55 Roquin-interacting mRNAs by PAR-CLIP in HEK293 cells (FIG. 7f).

RC3H1 Binding Sites are Mostly Located in 3'UTR of mRNA Targets

Next we examined the distribution of RC3H1 binding sites along mRNA transcripts. The majority of binding sites (81%) were found to be located in 3'UTRs (FIG. 1d), consistent with previous observations that RC3H1 binds to ICOS and TNF mRNAs through 3'UTR interactions[4,5,24]. A preference for RC3H1 binding within 3'UTRs was not apparent and sequence clusters were almost equally distributed over this transcript region (FIG. 7g). Since a previous study suggested a functional link between RC3H1 binding and microRNA (miRNA) activity[4], we examined the local interactions between RC3H1 and miRNA by computing the density of conserved miRNA target sites around RC3H1 preferred crosslinking sites (FIG. 7h). The observed profile did not show an overrepresentation of miRNA seeds complements overlapping with RC3H1 binding sites, arguing against a general functional link between miRNA regulation and RC3H1 binding.

Identification of U-Rich Sequences and Stem-Loop Secondary Structure as Recognition Element of RC3H1

To investigate the RNA elements recognized by RC3H1, we searched for sequence motifs and secondary structure features in RC3H1 binding sites. First, we examined 7mer occurrences in 41 nt windows centered on preferred crosslinking sites in RC3H1 binding sites. Notably, U-rich sequences were frequently found in RC3H1 binding sites derived from both 4SU and 6SG experiments, suggesting that the frequent observation of U-richness is not due to a bias introduced by using 4SU (FIG. 2a). Furthermore, AU-rich sequences were more highly enriched in RC3H1 consensus binding sites in 3'UTR sequences, when compared to GU-rich 7mer sequences (FIG. 2b). In addition, U-rich sequences were found in close proximity of preferred crosslink sites, suggesting the direct interaction of RC3H1 with these sequences (FIG. 2c). In addition, we examined the occurrence of the previously identified CDE motif[8], and found that core CDE consensus sequence (UCYRYGA) was found in RC3H1 binding sites, but the frequency was less prominent than that of several U-rich sequences (FIG. 2c).

Figure 8:
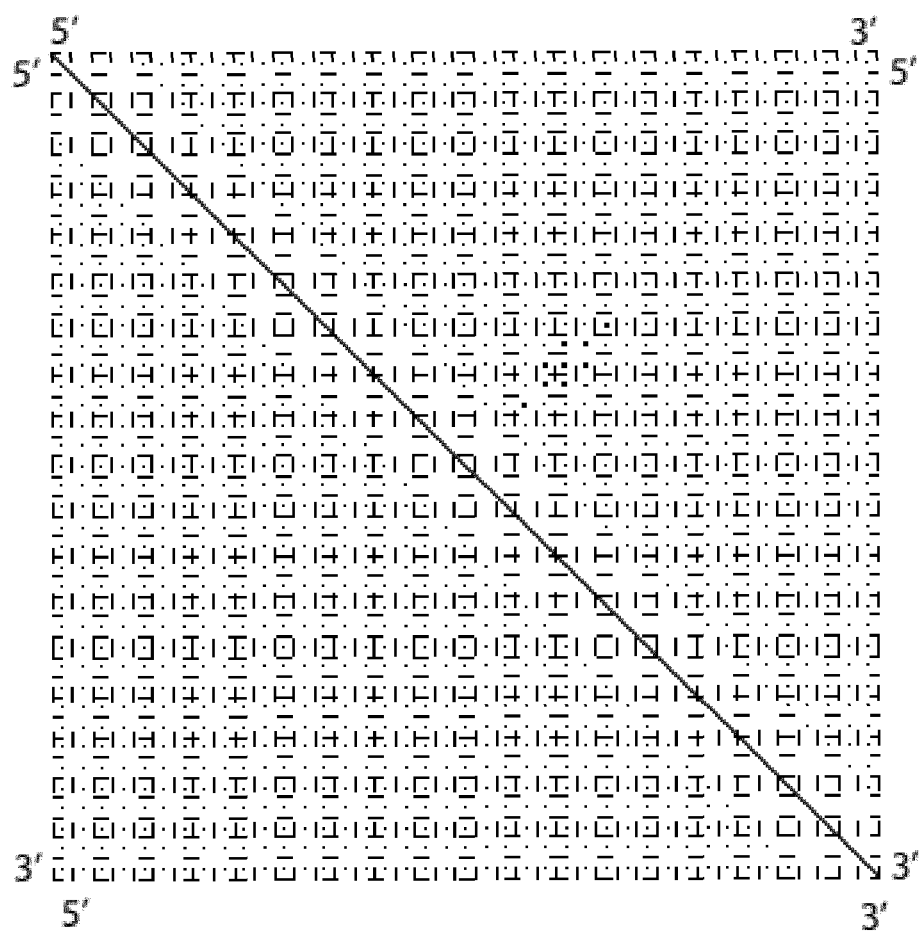
Figure 8:
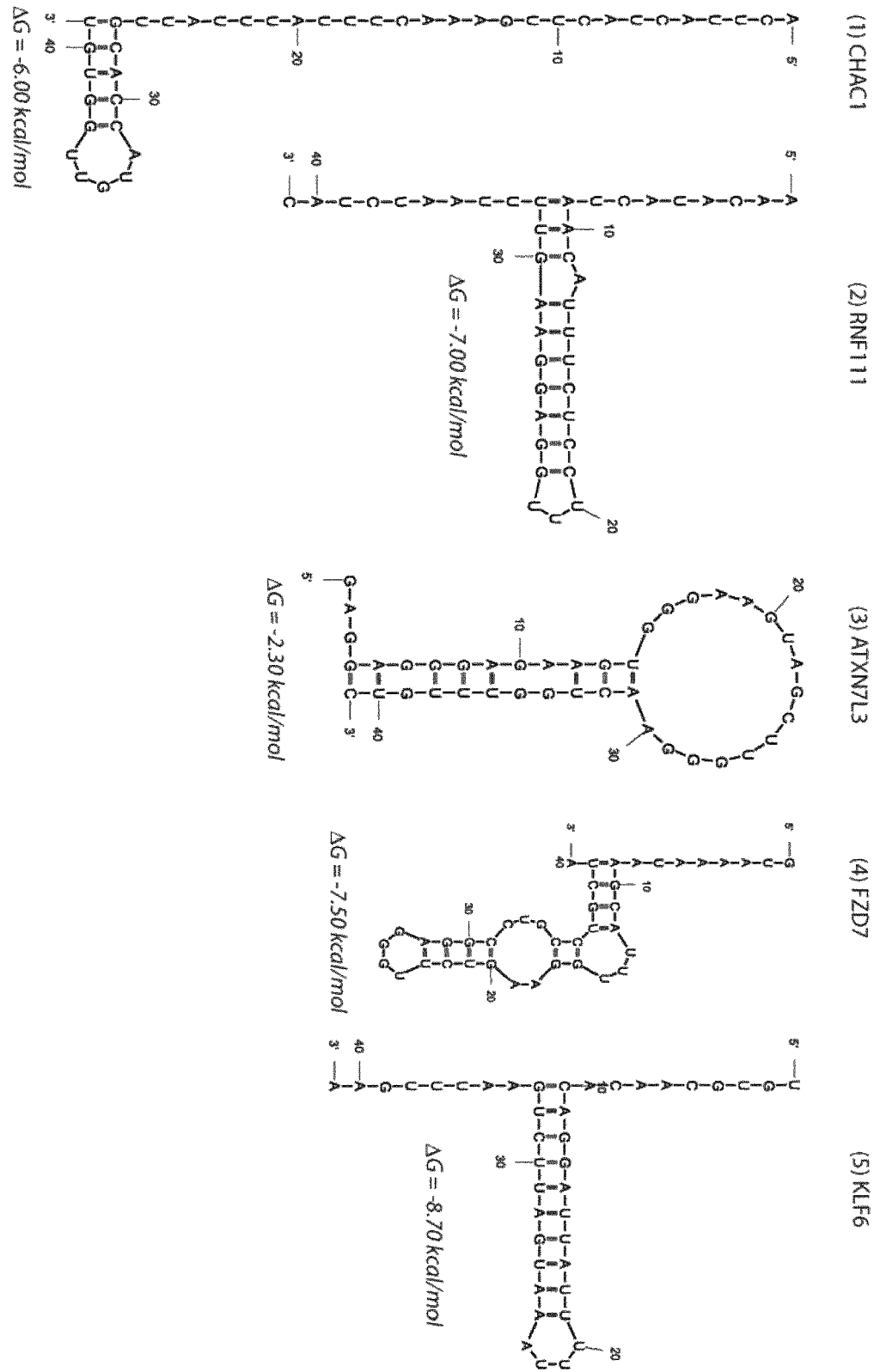
Figure 8:
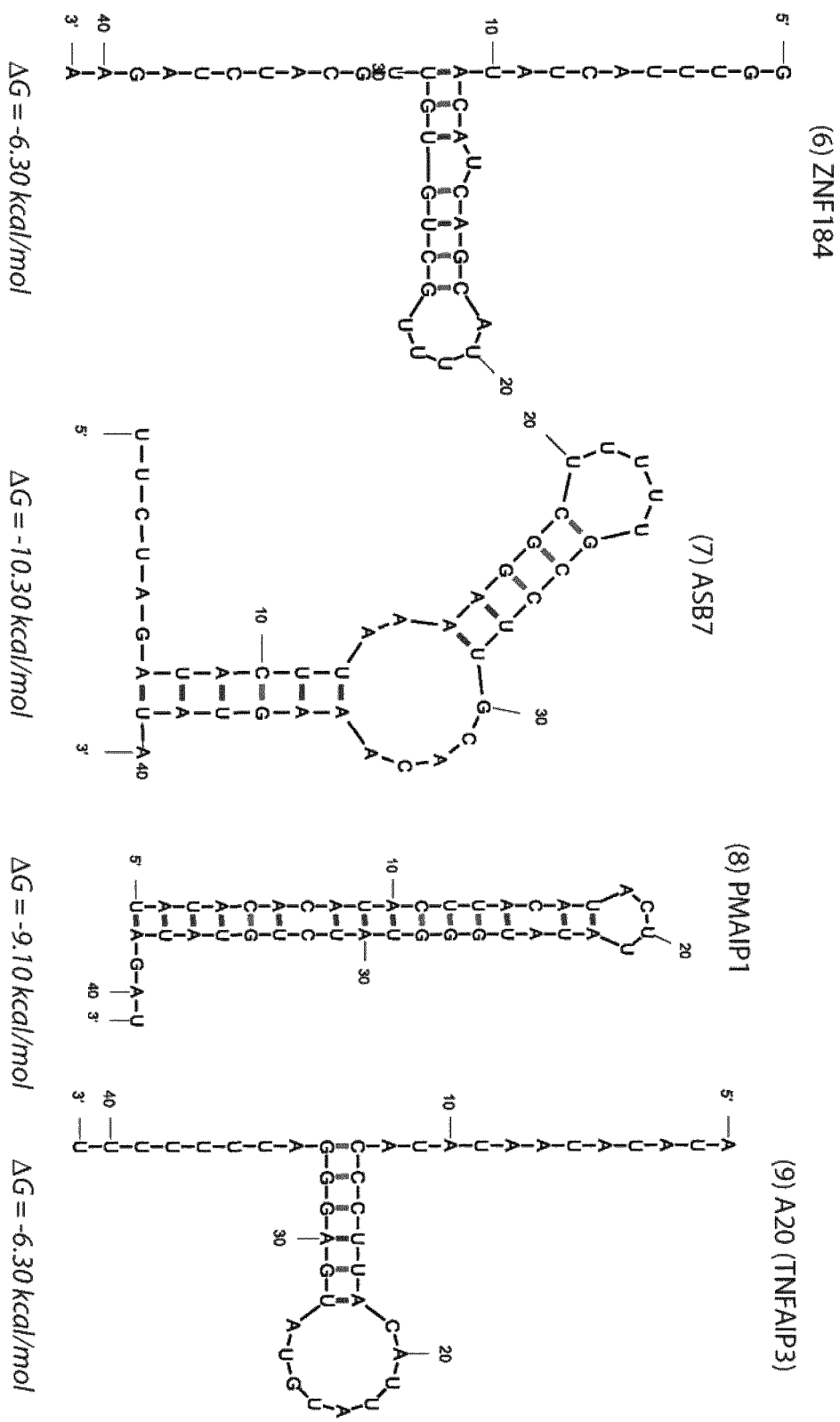

To examine potential secondary structure features in RC3H1 binding sites, we computationally folded a 41 nt sequence stretch centered around preferred crosslinking sites and averaged the resulting base pairing probabilities. Randomly selected RNA regions of the same length within 3'UTRs of RC3H1 mRNA target transcripts served as a background control. In 3'UTR RC3H1 consensus binding sites the base pairing probability was reduced in the vicinity of crosslink sites and increased in the flanking region compared to background, suggesting that RC3H1 binding sites tend to form stem-loop structures (FIG. 2d and FIG. 8). This observation was consistent with a recent finding that RC3H1 contacts the stem-loop structure of the CDE motif via its ROQ domain[8-10]. Since our motif analysis identified AU-rich sequences, we hypothesized that RC3H1 recognition elements might be composed of a combination of structure/sequence specificity features which could be contacted by the different RNA-binding domains of RC3H1. Therefore, we classified RC3H1 binding sites into two groups based on the presence of AU-rich sequences, and independently performed the secondary structure analysis for each group. RC3H1 binding sites which do not contain AU-rich sequences folded into more extended hairpin structure (FIG. 2d), similar to the TNFα CDE, than binding sites containing AU-rich sequences. These sites were also predicted to form stem-loop structures but with lower base pairing probability likely due to the higher AU-content, suggesting that these hairpin structures contained larger loops and shorter stems (FIG. 2d). Together with the observation that AU-rich sequences are located in the direct proximity of crosslink sites (FIG. 2c), which often map to the loop sequence (FIG. 2d), U-rich sequences seem to be embedded in or around the loop. Hairpin structures frequently containing AU-rich sequences and albeit less frequently the CDE consensus sequence were detected as recognition elements of RC3H1.

RC3H1-Bound mRNAs are Short-Lived and Show Increased Protein Synthesis Upon RC3H1 Knockdown To examine whether RC3H1 influences the stability of its target transcripts we performed transcriptome-wide mRNA half-life measurements as described by Dölken and colleagues[27], and compared half-lives of RC3H1-bound and unbound mRNA transcripts. Consistent with the function of RC3H1 in mRNA decay, RC3H1-targeted mRNAs were found to have significantly shorter half-lives than non-targets (FIG. 3c, d). Furthermore, we found that mRNA half-lives of RC3H1-bound transcripts inversely correlated with an expression normalized PAR-CLIP score (FIG. 3e), suggesting that the extent of RC3H1-mRNA binding determined the mRNA half-lives of bound mRNAs.

Figure 9:
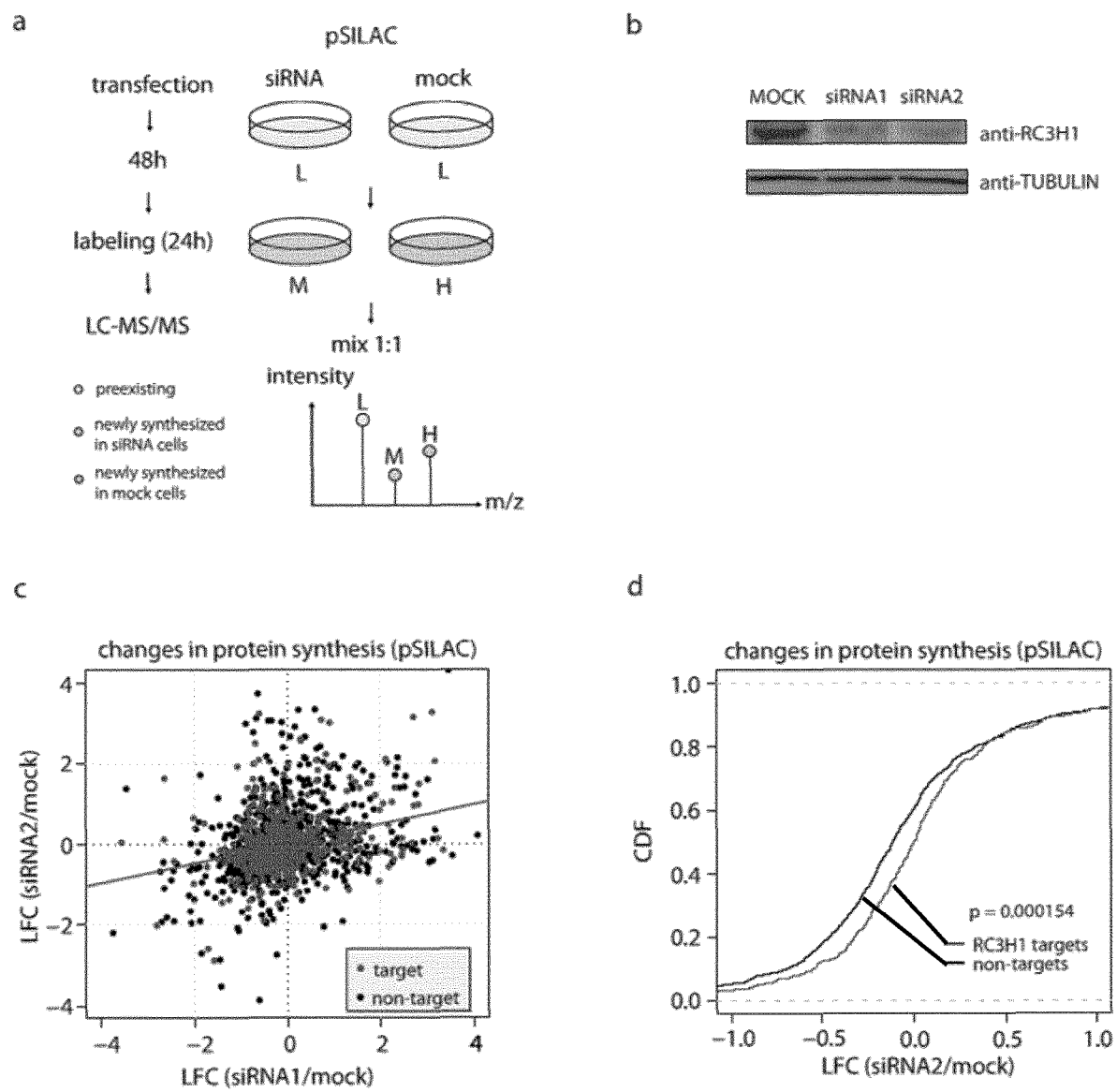

Next, we examined the effect of RC3H1 depletion on the protein synthesis rate of RC3H1-bound mRNAs. For this purpose, we monitored changes in newly synthesized proteins by pSILAC based quantitative proteomics[20,28] upon depletion of endogenous RC3H1 in HEK293 cells (FIG. 9a). The mass shift between the RC3H1 knockdown ("medium" labeled) and mock-treated control ("heavy" labeled) allowed the quantification of changes in protein synthesis of ~2400 proteins (FIG. 9a).

RC3H1 knockdown was confirmed by Western blot analysis (FIG. 9b). A cumulative distribution function showed that the level of protein synthesis of RC3H1-bound mRNAs was significantly increased upon RC3H1 depletion by two siRNAs (FIG. 3f and FIG. 9b,c,d). Taken together, our data indicate that RC3H1-bound mRNAs are short-lived and RC3H1 represses expression of target transcripts, validating the functionality of RC3H1-mRNA interactions.

RC3H1 Interacts with DNA Damage Induced Transcripts

Figure 10:
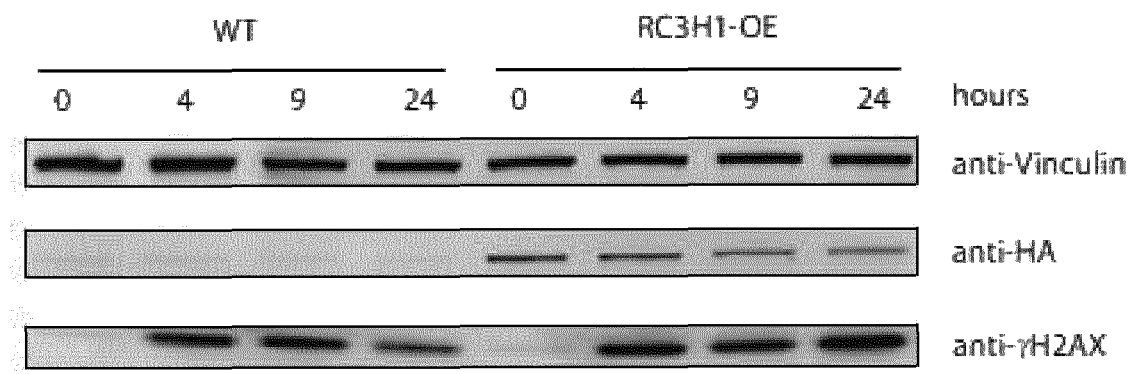
Figure 10:
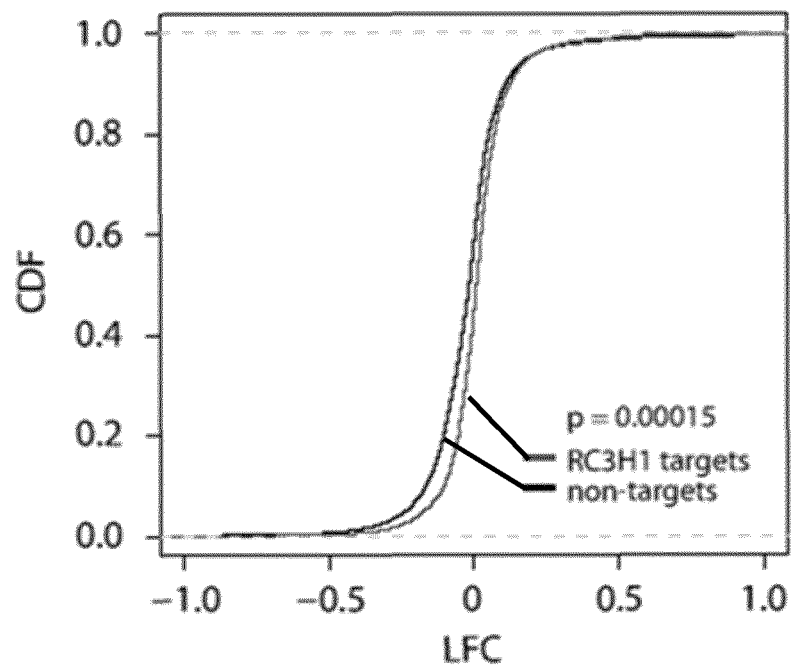

Our KEGG pathway enrichment analysis revealed that RC3H1 mRNA targets are significantly enriched for genes involved in cell cycle regulation and p53 signaling (FIG. 7e) Furthermore, RC3H1 was shown to localize to stress granules upon oxidative stress induced by arsenite exposure[24], suggesting an involvement of RC3H1 in the cellular stress response. To investigate a possible role of RC3H1 in the DNA damage response, we correlated changes in mRNA expression levels upon DNA damage induced by neocarcinostatin (NCS) in HEK293 cells[29] with our RC3H1 PAR-CLIP data (FIG. 4a). Notably, RC3H1-bound transcripts were more induced upon DNA damage than non-targeted mRNAs (FIG. 4b). This finding implies that the expression levels of DNA damage induced genes are likely modulated at the post-transcriptional level at least in part by RC3H1. The A20, a NF-κB target gene that acts as a feedback regulator of NF-κB activation, was amongst the RC3H1 target transcripts and showed the largest increase upon DNA damage. Over-expression of FLAG/HA-tagged RC3H1 resulted in a significant reduction of A20 mRNA (FIG. 4c) upon DNA damage (FIG. 10a). Furthermore, we observed that A20 mRNA half-life was shortened by induction of tagged RC3H1 (FIG. 4d). To provide further support for this finding, we specifically blocked the RC3H1 binding site on A20 mRNA by transfecting an antisense Locked Nucleic Acid (LNA) oligonucleotide and observed an increase in A20 mRNA half-life (FIG. 4e).

RC3H1 Binds to a Composite Structure-Sequence Motif in the 3'UTR of A20

Our PAR-CLIP data indicated a single RC3H1 binding site in the 3'UTR of A20 mRNA. This site folds into a conserved short hairpin structure with an AU-rich sequence located in the loop and another AU-rich sequence upstream of the stem-loop structure. Diagnostic PAR-CLIP T to C transition events, indicating protein-RNA crosslinking sites, were detected in the AU-rich sequence located upstream of the stem-loop structure and within the loop (FIG. 5a).

To examine whether the putative A20-binding site bestows RC3H1-dependent mRNA decay, we cloned a 37-bp sequence covering the crosslinked region into a green fluorescent protein (GFP) reporter and assayed mRNA turnover by quantitative reverse transcription-PCR (qRT-PCR) after blocking transcription using actinomycin D. Indeed, insertion of the RC3H1-bound A20 site into the 3' UTR of the reporter construct destabilized reporter transcripts in mock-transfected cells, but not in RC3H1- and RC3H2-depleted cells (FIG. 5e), indicating that RC3H proteins destabilize the re-porter transcripts through this A20 site.

To examine the RC3H1 interaction with the identified A20 binding site, which differs significantly from the previously described CDE stem-loop structure, we used electrophoretic mobility shift assays (EMSA). Additionally to assess the contribution of the different RC3H1 domains to RNA-binding, we expressed two variants: RC3H1-N1 (aa 2-399) contained the N-terminal RING and ROQ domains, while RC3H1-N2 (aa 2-452) harbored RING, ROQ, and CCCH-type zinc finger domains (FIG. 5b). Both recombinant proteins bound to the ICOS CDE-like stem-loop motif RNA (FIG. 5b). The formation of the protein-RNA complex seemed to be independent of the CCCH-type zinc finger domain. In contrast the 23 nt A20 hairpin RNA was bound by RC3H1-N2 with higher affinity than RC3H1-N1, indicating that the CCCH-type zinc finger domain plays a role in the interaction with the non-CDE-type A20 site. The addition of 14 nucleotides 5' prime of the stem-loop structure (A20 37 nt) further increased the affinity of the RC3H1-N2 variant to the RNA substrate, suggesting that an additional sequence upstream of the A20 hairpin is involved in protein-RNA complex formation.

Moreover, the antisense LNA oligonucleotide, which was used to modulate A20 mRNA stability (FIG. 4e) and hybridizes to the loop and the 3' part of the stem, reduced the binding of RC3H1-N2 to the 37 nt A20 target sequence in vitro, suggesting that the LNA oligonucleotide interferes with the binding of RC3H1 (FIG. 5c). Finally, we examined the functionality of the RC3H1 binding site in the A20 3'UTR in a cellular context. To this end, we generated a destabilized GFP (d2GFP) reporter construct with a 3'UTR harboring the RC3H1 A20 binding site including the upstream AU-rich sequence and stem-loop structure. This construct and variants with mutations in the RC3H1 binding site were co-transfected with a mCherry control plasmid into HEK293 cells. Since the d2GFP protein half-life is shortened to about 2 hours by a C-terminal fusion to a PEST domain[30], the expression level of d2GFP measured by FACS analysis likely approximates the abundance of d2GFP mRNA. Indeed, insertion of the A20 site into the 3'UTR of the reporter construct reduced d2GFP expression, indicating a repressive effect in HEK293 cells (FIG. 5d). Mutations disrupting the base-paring of the stem had no apparent effect on d2GFP expression, whereas mutations of the AU-rich sequence element next to the stem loop partially abrogated repression. An additional mutation of a uridine in the hairpin loop almost completely derepressed d2GFP expression (FIG. 5d), suggesting that sequence-specific contacts by RC3H1 in the AU-rich sequence upstream of the hairpin and the loop are required for repression.

RC3H1 Overexpression Represses A20 Resulting in Increased Phosphorylation of IKK NF-κB is activated by a wide variety of stimuli, including cytokines such as TNFα[33,34]. To examine whether RC3H1 acts in a pathway specific manner, we used previously published mRNA expression data of TNFα-treated HEK 293 cells[35] to correlate RC3H1-bound mRNAs with TNFα-induced transcripts. Interestingly, RC3H1 target transcript showed a greater increase in expression upon TNFα induction than non-targets suggesting that RC3H1 acts posttranscriptionally on NF-κB target genes (FIG. 6a and FIG. 10b). Furthermore we could demonstrate that RC3H1 overexpression causes a reduction of basal and stimulus-dependent A20 mRNA and protein levels (FIG. 6b, c), similar to A20 expression changes observed during the response after DNA damage (FIG. 4c).

Since the A20 expression levels are regulated by RC3H1, enforced expression of RC3H1 could modulate NF-κB pathway activity. NF-κB activation is mediated via the IκB kinase (IKK) complex, which catalyzes the phosphorylation of IκB and NF-κB proteins, as well as of other substrates[32-34,36]. Signaling involves ubiquitin-mediated complex formation of pathway components and is controlled at various levels by negative feedback mechanisms, including ubiquitin-editing enzymes such as A20[37].

Indeed, overexpression of RC3H1 resulted in a significant increase of IKK activation. In line with this, elevated Ser536 phosphorylation of the IKK substrate p65[37] was also observed. However, IκBα degradation was not detectably affected, while IκBα re-synthesis was slightly reduced (FIG. 6c). IκBα was determined as another RC3H1 target (FIG. 6a), indicating RC3H1-mediated mRNA decay.

Knockdown of RC3H1 and RC3H2 in HEK293 cells resulted in a small, but reproducible, upregulation of A20 protein expression (FIG. 6e), which resulted in decreased phosphorylation of IKK (FIG. 6e), decreased phosphorylation of its substrate p65 (FIG. 6e) and reduced NF-kB DNA-binding activity (FIG. 6f). Taken together, the examples demonstrate that RC3H1 regulates the expression of several NF-kB pathway regulators, thereby modulating IKK and NF-kB activity.

Discussion of the Experimental Examples

In the present study, we identified transcriptome-wide RNA binding sites of human RC3H1 at nucleotide resolution in HEK293 cells using PAR-CLIP. Our bioinformatic analyses did not reveal a well-defined motif as observed for a number of RNA-binding proteins (Ray et al Nature 2013), however indicated a sequence-structure binding element with AU-rich sequences frequently embedded in RNA stem-loop structures located in 3'UTRs of target transcripts. Surprisingly, the CDE core consensus motif (UCYRYGA; SEQ ID NO 16) deduced by Leppek and coworkers[8] was present in a minor fraction of identified RC3H1 binding sites. The interaction of RC3H1 with a relaxed CDE consensus is in agreement with recent structural and mutational analyses of roquin binding sites[9] indicating that a shape-specific rather than sequence-specific recognition of CDE RNA hairpins by a monomeric ROQ domain explains the specificity of roquin in the regulation of transcripts containing CDE-like RNA elements.

Interestingly, our finding of a PAR-CLIP cluster in the A20 3'UTR indicated a yet-unrecognized RC3H1 binding mode and specificity. In contrast to a typical CDE stem-loop motif, which is sufficiently bound by the ROQ domain, we provide evidence that the CCCH-type zinc finger domain is involved in contacting the A20 site. A RC3H1 variant containing the CCCH-type zinc finger domain bound with higher affinity to a non-CDE-like stem-loop structure with an additional AU-rich sequence upstream of the hairpin than to the hairpin alone. In contrast, the N-terminal RC3H1 variant lacking the CCCH-type zinc finger domain poorly bound to both of these RNA substrates. In addition nucleotide changes in the upstream AU-rich sequence resulted in partial derepression of a reporter construct, suggesting that the AU-rich sequence next to the hairpin and the short stem-loop structure itself are likely collaboratively bound by the CCCH-type zinc finger and ROQ domains. The makeup of RC3H1 by distinct RNA-binding domains might allow the protein to recognize a wider range of RNA sequences and could function on a larger set of regulatory elements than previously anticipated. The ratio of sequence and structure specificity features, determining the strength of the RC3H1-mRNA association, and the RNA-recognition-element frequency would influence the regulatory capacity of the RNA-binding protein.

In addition our results indicate that RC3H1 target transcripts have in general shorter mRNA half-lives. RC3H1-bound mRNAs are encoded by genes with various biological functions outside of immune response pathways, which is in accordance with the mouse phenotype of Rc3h1 null-knockout that showed perinatal lethality with broad physiological complications[38]. Enriched KEGG pathways included cell cycle, p53 signaling and tumor pathways. By intersecting our PAR-CLIP target mRNAs with mRNA expression data, we found that RC3H1 targets are significantly enriched for mRNAs induced by DNA damage[29] and TNF[35]. As shown for one of the top mRNA targets, A20, we postulate that RC3H1 in general is involved in fine-tuning or clearance of transcriptionally induced mRNAs by shortening their half-lives.

The zinc finger protein A20 is an important negative regulator of inflammation[19] and several studies have highlighted the clinical and biological importance of A20. Vande Walle and colleagues recently showed that negative regulation of the NLRP3 inflammasome by A20 protects against arthritis[39]. Since RC3H1 is a negative regulator of A20, targeting of the RC3H1-A20 mRNA interaction by employing antisense technologies and concomitant upregulation of A20 protein demonstrates beneficial clinical outcomes in certain disease scenarios.

In summary, we identified comprehensive RC3H1 binding sites by PAR-CLIP, revealing a large number of novel mRNA targets as well as novel RC3H1 cis-acting recognition element in the A20 3'UTR.

Materials and Methods Used in the Experimental Examples

Antibodies anti-HA.11 (COVANCE, 16612), anti-FLAG (SIGMA, F1804), anti-myc (SIGMA, 9E10) anti-gamma H2AX (Upstate, JBW301), anti-vinculin (Sigma, hVIN-1), anti-A20 (sc-32525, Santa-Cruz Biotechnology), anti-pIKKalpha (2697, Cell Signal Technology), anti-IKKalpha (556532, BD Pharmingen), anti-IkappaBalpha (sc-371, Santa-Cruz Biotechnology), anti-p65 (sc-8008P, Santa Cruz Biotechnology), anti-p-p65 (3033, cell signaling), polyclonal goat anti-mouse or anti-rabbit immunoglobulins/HRP (DAKO)

```
Oligonucleotides
siRNAs
siRNA 1 for RC3H1:
                                            (SEQ ID NO 17)
5'-GCUGGGAAAUACAAAGGAA[dT][dT]

siRNA 2 for RC3H1:
                                            (SEQ ID NO 18)
5'-CCAAGAAAUGUGUAGAAGA[dT][dT]

qPCR primers
RC3H1
forward:
                                            (SEQ ID NO 19)
5'-tggacaaccagaaccacaaa;

reverse;
                                            (SEQ ID NO 20)
5'-GCTGATCCATTTGGTACATCAC A20
forward:
                                            (SEQ ID NO 21)
5'-TGCACACTGTGTTTCATCGAG;

reverse:
                                            (SEQ ID NO 22)
5'-ACGCTGTGGGACTGACTTTC
```

RPL18A:
forward;
(SEQ ID NO 23)
5'-GGAGAGCACGCCATGAAG;

reverse;
(SEQ ID NO 24)
5'-AAGATTCGCATGCGGTAGAG

GAPDH:
forward;
(SEQ ID NO 25)
5'-AGCCACATCGCTCAGACAC;

reverse;
(SEQ ID NO 26)
5'-GCCCAATACGACCAAATCC

NFKBIA:
forward;
(SEQ ID NO 27)
5'-GAGTCAGAGTTCACGGAGTTC;

reverse;
(SEQ ID NO 28)
5'-CATGTTCTTTCAGCCCCTTTG

DNA oligos for d2GFP-A20 3'UTR reporter
WT
sense:
(SEQ ID NO 29)
5'-GGCCTGTACATATATAATATACCCTTACATTATGTATGAGGGATTTT;

antisense:
(SEQ ID NO 30)
5'-TCGAAAAATCCCTCATACATAATGTAAGGGTATATTATATATGTACA

Mut1
sense:
(SEQ ID NO 31)
5'-GGCCTGTACATATATAATATACCCTTACATAATCTATCAGCGATTTT;

antisense:
(SEQ ID NO 32)
5'-TCGAAAAATCGCTGATAGATTATGTAAGGGTATATTATATATGTACA

Mut2
sense:
(SEQ ID NO 33)
5'-GGCCTGTACAAAAAAAAAAAACCCTTACATAATCTATCAGCGATTTT;

antisense:
(SEQ ID NO 34)
5'-TCGAAAAATCGCTGATAGATTATGTAAGGGTTTTTTTTTTTGTACA

Mut3
sense:
(SEQ ID NO 35)
5'-GGCCTGTACAAAAAAAAAAAACCCTTACATTATGTATGAGGGATTTT;

antisense:
(SEQ ID NO 36)
5'-TCGAAAAATCCCTCATACATAATGTAAGGGTTTTTTTTTTTGTACA

Mut4
sense;
(SEQ ID NO 37)
5'-GGCCTGTACATGTACGATCTGCCCTTACATTATGTATGAGGGATTTT;

antisense:
(SEQ ID NO 38)
5'-TCGAAAAATCCCTCATACATAATGTAAGGGCAGATCGTACATGTACA

Mut5
sense;
(SEQ ID NO 39)
5'-GGCCTGTACATGTACGATCTGCCCTTACATAATCTATCAGCGATTTT;

antisense:
(SEQ ID NO 40)
5'-TCGAAAAATCGCTGATAGATTATGTAAGGGCAGATCGTACATGTACA

Mut6
sense:
(SEQ ID NO 41)
5'-GGCCTGTACATGTACGATCTGCCCTTACAAAATCTATGAGGGATTTT;

antisense:
(SEQ ID NO 42)
5'-TCGAAAAATCCCTCATAGATTTTGTAAGGGCAGATCGTACATGTACA

RNA oligos
ICOS (13 nt):
(SEQ ID NO 43)
5'-AUUUCUGUGAAAU

A20 (23 nt):
(SEQ ID No. 5)
5'-ACCCUUACAUUAUGUAUGAGGGA

A20 (37 nt):
(SEQ ID No. 3)
5'-AUAUAUAAUAUACCCUUACAUUAUGUAUGAGGGAUUU

Plasmids pENTR4 constructs were generated by PCR amplification of the RC3H1 and QKI5 coding sequences (CDS) from cDNA followed by restriction digest and ligation into the pENTR4 (Invitrogen) backbone, which were further recombined into the pFRT/TO/FLAG/HA-DEST destination vector[40] using GATEWAY LR recombinase (Invitrogen) according to manufacturers protocol. Expression plasmids for HA-tagged CNOT1 and CNOT8 were kind gifts from Dr. W Filipowicz. pENTR4 QKI5 were recombined into pFRT/FLAG/HA-DEST (Addgene ID: 26360). The d2GFP reporter plasmids were generated by cloning the d2GFP (Clontech) coding sequence into pcDNA5/FRT, and synthetic DNA oligonucleotides containing the A20 binding site were annealed and ligated into the 3'UTR of d2GFP using the Xho1/Not1 site.

Cell Lines and Culture Conditions

Flp-In 293 T-REx cells (Invitrogen) were grown in DMEM high glucose with 10% (v/v) fetal bovine serum, 2 mM L-glutamine. Cell lines stably expressing FLAG/HA-tagged RC3H1 protein were generated by co-transfection of pFRT/TO/FLAG/HA constructs with pOG44 (Invitrogen). Cells were selected by adding 15 µg/ml blasticidin and 100 µg/ml hygromycin (Invivogen). Expression of epitope-tagged proteins was induced by addition of 1 µg/ml doxycyclin. The expression of FLAG/HA tagged RC3H1 was assessed by Western analysis using mouse anti-HA.11 monoclonal antibody (Covance). For quantitative proteomics, cells were grown in SILAC medium as described before[25,41]. Briefly, Dulbecco's Modified Eagle's Medium (DMEM) Glutamax lacking arginine and lysine (PAA) supplemented with 10% dialyzed fetal bovine serum (dFBS, Gibco) was used. Amino acids (84 mg/I $^{13}C_6^{15}N_4$ L-arginine plus 146 mg/I $^{13}C_6^{15}N_2$ L-lysine or 84 mg/I $^{13}C_6$-L-arginine plus 146 mg/I D4-L-lysine) or the corresponding non-labeled amino acids (Sigma), were added to obtain 'heavy' medium' or 'light' cell culture medium respectively. Labeled amino acids were purchased from Sigma Isotec.

Western Blot Analysis

Total cell lysates were prepared in 1×SDS-PAGE sample loading buffer (50 mM Tris pH7.5, mercaptoethanol, 1% SDS, 0.01% bromophenol blue, 10% glycerol) and resolved by SDS-PAGE. Proteins were transferred to nitrocellulose membrane (Whatman) using a semi-dry blotting apparatus (BioRad) at constant 20V for 1 h. The membrane was blocked in 5% non-fat milk and incubated with primary antibody. Following incubation for 1 h at room temperature, membranes were washed 3 times in TBST (150 mM NaCl, 20 mM Tris-HCl pH 7.5, 0.1% Tween) and incubated with HRP-conjugated secondary antibody for 1 h. Following 3 additional TBST washes, protein bands were visualized using ECL detection reagent (GE Healthcare) and a LAS-4000 imaging system (GE-Healthcare).

PAR-CLIP

Stably transfected and inducible FLAG/HA-RC3H1 expressing cells were labeled with 100 μM 4-thiouridine (4SU) or 6-thioguanosine (6SG) for 9 h. After labeling the cells, PAR-CLIP was performed essentially as described[17]. Briefly, for 4SU-2 and one 6SG, UV-irradiated cells were lysed in NP-40 lysis buffer (50 mM HEPES-KOH at pH 7.4, 150 mM KCl, 2 mM EDTA, 0.5% (v/v) NP40, 0.5 mM DTT, complete EDTA-free protease inhibitor cocktail). After mild treatment with RNaseT1 (Fermentas), immunoprecipitation was carried out with protein G magnetic beads (Invitrogen) coupled to anti-FLAG M2 antibody (SIGMA) from extracts of FLAG/HA-RC3H1 expressing and 4SU labeled HEK 293 cells for 1 h at 4° C. For 4SU-1, a high-salt lysis buffer (50 mM Tris-HCl, 500 mM NaCl, 1% (w/v) NP-40, 1 mM DTT and complete EDTA-free protease inhibitor cocktail) was used for cell lysis followed by sonication. After mild treatment with RNaseT1, purification of the RC3H1/RNA complex was performed with Flag magnetic beads (SIGMA). Following additional digestion by RNase T1 (Fermentas), beads were incubated with calf intestinal phosphatase (NEB) and RNA fragments were radioactively end-labeled using T4 polynucleotide kinase (Fermentas). The crosslinked protein-RNA complexes were resolved on a 4-12% NuPAGE gel (Invitrogen). The SDS-PAGE gel was transferred to a nitrocellulose membrane (Whatman) and the protein-RNA complex migrating at an expected molecular weight was excised. RNA was isolated by Proteinase K (Roche) treatment and phenol-chloroform extraction, ligated to 3' adapter. (5'-AppTCGTATGCCGTCTTCTGCTTG (SEQ ID NO 44)-InvdT for 4SU-1, 5'-AppTCTCGTATCGTATGCCGTCT-TCTGCTTG (SEQ ID NO 45)-InvdT for 4SU-2, 5'-AppTCTCTGCTCGTATGCCGTCTTCTGCTTG (SEQ ID NO 46)-InvdT for 6SG) and 5' adapter (5'-rGrUrUrCrAr-GrArGrUrUrCrUrArCrArGrUrCrCrGrArCrGrArUrC(SEQ ID NO 47)), reverse transcribed and PCR-amplified. The amplified cDNA was sequenced on a HighSeq2000 (Illumina) with a 1×51 nt cycle for 4SU-2 and 6SG and on a Genome Analyzer II with a 1×36 cycle for 4SU-1.

PAR-CLIP Data Processing

The PAR-CLIP cDNA sequencing data were analyzed using the PAR-CLIP analysis pipeline as described previously[20]. Reads mapping uniquely to the genome with up to one mismatch, insertion or deletion were used to build clusters of sequence reads, and filtering was performed to obtain RC3H1 clusters sites at an estimated 5% false-positive rate. For each cluster the position with the highest number of diagnostic transition events was determined and we defined this position as the preferred crosslink site. To define the consensus clusters, we pooled reads from all three experiments while ensuring that transition events are counted appropriately (T to C in reads originating from 4SU experiments and G to A only in reads from the 6SG experiment). Before the cutoff determination, clusters had to pass an additional consensus filter, demanding that reads from at least two out of the three experiments support the cluster. The resulting sets of clusters were denoted as the "consensus" set. Read alignment statistics, cluster length distribution, target gene identification, cluster distribution, cluster coverage profiles, conservation profile and miRNA target scan were generated by the PAR-CLIP analysis pipeline as described previously[20]. KEGG pathway and GO term enrichment analysis was performed using the on-line DAVID program[42,43] The top 1000 transcripts (ranked by the number of PAR-CLIP diagnostic mutations falling into 3'UTR) were used for pathway enrichment analysis.

Motif Analysis

7mer occurrences were counted in 41nt windows around the crosslink site identified in the 4SU and 6SG PAR-CLIP experiments using custom Perl scripts. To examine the enrichment of each 7mer motif, 7mer frequency occurring in RC3H1 consensus 3'UTR binding sites was compared to that occurring in all 3'UTR sequences retrieved from UTRdb[44]. The longest 3'UTR sequence for each gene was used in this analysis. To test whether RC3H1 binding sites showed a preferred secondary structure we used the library routines from the Vienna RNA package 1.8.2[45] to compute base pairing probabilities within 41 nt sequences centered on the preferred crosslink positions of 3'UTR binding sites. The resulting profiles were accumulated and averaged over the following sets of binding sites (1) all 3'UTR consensus binding sites (2) Top 1000 3'UTR binding sites that contain AU-rich sequences defined by 6mer consisting of A or U. Ranking is based on the number of diagnostic PAR-CLIP transition divided by microarray expression level of the gene harboring the binding site. (3) Top 1000 3'UTR binding sites that do not contain AU-rich sequences. (4) Negative control 41 nt sequences randomly selected from the 3'UTRs of RC3H1 target transcripts.

siRNA Knockdown and pSILAC

Flp-In 293 T-REx cells were grown in SILAC medium supplemented with "light" labeled amino acids prior to siRNA knockdown experiments. siRNAs were transfected at a final concentration of 50 nM using Lipofectamine RNAiMAX (Invitrogen). Controls (mock) were treated with transfection reagent only. Following 24 h of incubation, siRNA transfected cells were switched to "medium" labeled SILAC medium, while mock control cells were switched to "heavy" labeled SILAC medium. After 24 h of labeling, cells were harvested and equal amounts of siRNA- and mock-transfected cells were pooled, lysed in urea buffer (8 M urea, 100 mM Tris·HCl, pH 8.3) and sonicated for 20 s (2 pulses, 60% power). Cell debris was removed by centrifugation (14000 g, 5 min). Protein concentration was then measured by the Bradford colorimetric assay. 100 μg of proteins were reduced in 2 mM DTT for 30 min at 25° C. and successively free cysteines were alkylated in 11 mM iodoacetamide for 20 min at room temperature in the dark. LysC digestion was performed by adding LysC (Wako) in a ratio 1:40 (w/w) to the sample and incubating it for 18 h under gentle shaking at 30° C. After LysC digestion, the samples were diluted 3 times with 50 mM ammonium bicarbonate solution, 7 μl of immobilized trypsin (Applied Biosystems) were added and samples were incubated 4 h under rotation at 30° C. Digestion was stopped by acidification with 10 μl of trifluoroacetic acid and trypsin beads were removed by centrifugation. 15 μg of digest were desalted on STAGE Tips, dried and reconstituted to 20 μl of 0.5% acetic acid in water[46]. 5 μl of each sample were injected in duplicate on a LC-MS/MS system (nanoLC-Ultra 1D (Eksigent) coupled to LTQ-Orbitrap Velos (Thermo)), using a 240 min gradient ranging from 5% to 40% of solvent B (80% acetonitrile, 0.1% formic acid; solvent A=5% acetonitrile, 0.1% formic acid). For the chromatographic separation ~25 cm long capillary (75 μm inner diameter) was packed with 1.8 μm C18 beads (Reprosil-AQ, Dr. Maisch). On one end of the capillary nanospray tip was generated using a laser puller (P-2000 Laser Based Micropipette Puller, Sutter Instruments), allowing fritless packing. The nanospray source was operated with spay voltage of 2.1 kV and ion transfer tube temperature of 260° C. Data were acquired in data dependent mode, with one survey MS scan in the Orbitrap mass analyzer (resolution 60000 at m/z 400) followed by up to 20 MS/MS in the ion trap on the most intense ions (intensity threshold=750 counts). Once selected for fragmentation, ions were excluded from further selection for 30 s, in order to increase new sequencing events. Raw data were analyzed using the MaxQuant proteomics pipeline (v1.3.0.5) and the built-in Andromeda search engine[47] with the International Protein Index Human version 3.71 database. Carbamidomethylation of cysteines was chosen as fixed modification, oxidation of methionine and acetylation of N-terminus were chosen as variable modifications. The search engine peptide assignments were filtered at 1% FDR and the feature match between runs was enabled; other parameters were left as default. For SILAC analysis, two ratio counts were set as threshold for quantification Quantitative PCR Cells were harvested and total RNA was isolated using Trizol (Invitrogen) according to manufacturer's protocol. Total RNA was treated with DNaseI (Invitrogen), and complementary DNA (cDNA) synthesis was performed using Superscript III (Invitrogen) with oligo-dT primer (18-20 nt) or random hexamer primer (Invitrogen) according to manufacturer's protocol. qPCR analysis was performed with Power SYBR Green PCR Master Mix (ABI) and ABI light cycler as described in the manufacturers' instructions.

mRNA Decay Assay

Cells were treated with 5 µg/ml of actinomycin D (Sigma-Aldrich) to block the transcription. At 0, 2 and 4 h post actinomycin D treatment, total RNA was harvested using Trizol (Invitrogen) according to manufacturer's protocol. Abundance of specific RNA was quantified by quantitative RT-PCR. mRNA levels were normalized against RPL18A mRNA and plotted against time.

LNA Transfection

LNA oligonucleotide (Exiqon) antisense to the RC3H1 bound stem-loop located in the 3'UTR of A20 (+AA+AT+CC+CT+CA+TA+CA+TAA+T) was transfected at a final concentration of 100 nM using Lipofectamine RNAiMAX (Invitrogen). For control experiment, control LNA (Exiqon) targeting RC3H1 unbound region in the 3'UTR of A20 (+TCCA+CCTC+CCCT+CCC+CC+A) was transfected as above. Note that + indicates that the following nucleobase is present as a Locked Nucleic Acid modified residue. For mRNA decay assay after antisense inhibition at 4 h after the transfection of LNA, medium was replaced with fresh medium containing 250 ng/ml of neocarzinostatin (NCS) (Sigma-Aldrich) to induce DNA damage and A20 expression. At an additional 5 h after induction of DNA damage mRNA decay assay was performed. Random hexamer primers (Invitrogen) were used for cDNA generation.

Global Measurement of mRNA Half-Lives

Measurement of mRNA half-lives was performed as described previously[27].

Recombinant Protein Expression and Purification

DNA encoding the RING and ROQ domains (RC3H1-N1; aa 2-399) or the RING, ROQ and zf domains (RC3H1-N2; aa 2-452) was subcloned into the pQLinkH vector[48]. The genes were expressed as N-terminal His$_7$-tagged proteins at 17° C. in *E. coli* Rosetta™ 2 (DE3) (Novagen) using a LEX ultra-high-throughput bench-top bioreactor (Harbinger Biotech). Cells were grown at 37° C. in Terrific Broth medium and induced at an OD$_{600}$ of 2.0-2.5 with 0.5 mM isopropyl β-D-1-thiogalactopyranoside. For purification, cells were resuspended in phosphate-buffered saline (PBS) lysis buffer (1×PBS pH 7.4, 0.5 M NaCl, 5% (v/v) glycerol, 0.5 mM DTT), supplemented with 0.25% (w/v) 3-[(3-cholamidopropyl) dimethylammonio]-1-propanesulfonate, 0.1 mM phenylmethyl sulfonyl fluoride, 1 U/ml RNase-free DNase I (Qiagen) and one tablet of EDTA-free Complete Protease Inhibitor (Roche). The purification procedure comprises mechanical cell lysis by sonication (SONOPULS HD 2200, Bandelin), an Ni/Zn affinity chromatography on a 5 ml HisTrap FF crude column (GE Healthcare), and a size-exclusion chromatography on a Superdex 200 prep grade column (XK 26×60, GE Healthcare). The His$_7$ tag was cleaved with tobacco etch virus protease prior to the gel-filtration step, followed by a reapplication of the cleaved protein on the Ni/Zn affinity column. The purification of protein constructs comprising the RING, ROQ and zf domains additionally included a cation-exchange chromatography on a Source 30S column (HR 16×10, GE Healthcare).

EMSA

The EMSA was performed as described before[49] with the following modifications: RNA was prepared by 5' end-labeling of commercially synthesized RNA oligonucleotides with [γ-$^{32}$P]-ATP using T4 polynucleotide kinase (NEB). Labeled RNA was gel purified and eluted and adjusted with H$_2$O to 1 pmol/µl. 50 fmol of labelled RNA was used per 20 µl reaction. Prior to binding reactions, a master mix containing labelled RNA, lx binding buffer (20 mM Tris-HCl (pH 7.5), 50 mM KCl, 5 mM MgCl$_2$, 20 µM ZnSO$_4$, 10% glycerol), 2 mM DTT, 0.05 mg/ml BSA, and 5 µg/ml heparin was heated at 90° C. for 1 min and gradually cooled down to room temperature. In parallel, a dilution series of 10× protein stocks was prepared in 1× protein dilution buffer (1× binding buffer, 5 µg/ml heparin). For each binding reaction, 2 µl of the 10× protein stock was added to 18 µl of the mastermix at room temperature for 2 h. After addition of 4 µl 6× loading buffer (30% glycerol, bromphenol blue, xylene cyanol), RNP complexes were resolved by nondenaturing PAGE (6% polyacrylamide, 0.5×TBE, 5% glycerol) in ice-cold 0.5×TBE buffer containing 20 µM ZnSO$_4$ at 100 V for 40 min. The protein-bound RNA and the free RNA were quantified using a phosphorimager.

EMSA to detect DNA binding activity were performed as described [50].

GFP Reporter Experiment

Reporter d2GFP plasmid was transfected together with mCherry-N1 using Lipofectamin 2000 (Invitrogen) according to manufacturer's protocol. At 18 h post transfection, cells were acquired by FACS (BD Fortessa) to measure GFP and mCherry signal using FlowJo 8.8.6 (Tree Star). Mean Fluorescence Intensity (MFI) of GFP from mCherry positive cells were normalized for MFI of mCherry.

Microarray Data Processing

Microarray raw data for DNA damage response and TNF☐ response were retrieved from GEO accessions GSE1676 and GSE28548, respectively. Robust Multi-array Average (RMA) background correction and quantile normalization was applied using affyR Bioconductor packages[51]. For the analysis of Affymetrix Human Genome U133 Plus 2.0 Array, probe set intensities mapping to the same gene were averaged to summarize into gene intensities, and genes with log 2 steady state expression level smaller than 5 were filtered out.

REFERENCES

1. Schoenberg, D. R. & Maquat, L. E. Regulation of cytoplasmic mRNA decay. *Nat Rev Genet* 13, 246-59 (2012).

2. Hao, S. & Baltimore, D. The stability of mRNA influences the temporal order of the induction of genes encoding inflammatory molecules. *Nat Immunol* 10, 281-8 (2009).
3. Vinuesa, C. G. et al. A RING-type ubiquitin ligase family member required to repress follicular helper T cells and autoimmunity. *Nature* 435, 452-8 (2005).
4. Yu, D. et al. Roquin represses autoimmunity by limiting inducible T-cell co-stimulator messenger RNA. *Nature* 450, 299-303 (2007).
5. Glasmacher, E. et al. Roquin binds inducible costimulator mRNA and effectors of mRNA decay to induce microRNA-independent post-transcriptional repression. *Nat Immunol* 11, 725-33 (2010).
6. Pratama, A. et al. Roquin-2 Shares Functions with Its Paralog Roquin-1 in the Repression of mRNAs Controlling T Follicular Helper Cells and Systemic Inflammation. *Immunity* 38, 669-80 (2013).
7. Vogel, K. U. et al. Roquin Paralogs 1 and 2 Redundantly Repress the Icos and Ox40 Costimulator mRNAs and Control Follicular Helper T Cell Differentiation. *Immunity* 38, 655-68 (2013).
8. Leppek, K. et al. Roquin promotes constitutive mRNA decay via a conserved class of stem-loop recognition motifs. *Cell* 153, 869-81 (2013).
9. Schlundt, A. et al. Structural basis for RNA recognition in roquin-mediated post-transcriptional gene regulation. *Nat Struct Mol Biol* (2014).
10. Tan, D., Zhou, M., Kiledjian, M. & Tong, L. The ROQ domain of Roquin recognizes mRNA constitutive-decay element and double-stranded RNA. *Nat Struct Mol Biol* (2014).
11. Maruyama, T. et al. Roquin-2 promotes ubiquitin-mediated degradation of ASK1 to regulate stress responses. *Sci Signal* 7, ra8 (2014).
12. Brooks, S. A. & Blackshear, P. J. Tristetraprolin (TTP): Interactions with mRNA and proteins, and current thoughts on mechanisms of action. *Biochim Biophys Acta* (2013).
13. Mukherjee, N. et al. Global target mRNA specification and regulation by the RNA-binding protein ZFP36. *Genome Biol* 15, R12 (2014).
14. Shaw, G. & Kamen, R. A conserved AU sequence from the 3' untranslated region of GM-CSF mRNA mediates selective mRNA degradation. *Cell* 46, 659-67 (1986).
15. Caput, D. et al. Identification of a common nucleotide sequence in the 3'-untranslated region of mRNA molecules specifying inflammatory mediators. *Proc Natl Acad Sci USA* 83, 1670-4 (1986).
16. Chen, C. Y. & Shyu, A. B. AU-rich elements: characterization and importance in mRNA degradation. *Trends Biochem Sci* 20, 465-70 (1995).
17. Hafner, M. et al. Transcriptome-wide identification of RNA-binding protein and microRNA target sites by PAR-CLIP. *Cell* 141, 129-41 (2010).
18. Shembade, N. & Harhaj, E. W. Regulation of NF-kappaB signaling by the A20 deubiquitinase. *Cell Mol Immunol* 9, 123-30 (2012).
19. Ma, A. & Malynn, B. A. A20: linking a complex regulator of ubiquitylation to immunity and human disease. *Nat Rev Immunol* 12, 774-85 (2012).
20. Lebedeva, S. et al. Transcriptome-wide analysis of regulatory interactions of the RNA-binding protein HuR. *Mol Cell* 43, 340-52 (2011).
21. Anders, G. et al. doRiNA: a database of RNA interactions in post-transcriptional regulation. *Nucleic Acids Res* 40, D180-6 (2012).
22. Ogata, H. et al. KEGG: Kyoto Encyclopedia of Genes and Genomes. *Nucleic Acids Res* 27, 29-34 (1999).
23. Ashburner, M. et al. Gene ontology: tool for the unification of biology. The Gene Ontology Consortium. *Nat Genet* 25, 25-9 (2000).
24. Athanasopoulos, V. et al. The ROQUIN family of proteins localizes to stress granules via the ROQ domain and binds target mRNAs. *FEBS J* 277, 2109-27 (2010).
25. Ong, S. E., Foster, L. J. & Mann, M. Mass spectrometric-based approaches in quantitative proteomics. *Methods* 29, 124-30 (2003).
26. Doidge, R., Mittal, S., Aslam, A. & Winkler, G. S. Deadenylation of cytoplasmic mRNA by the mammalian Ccr4-Not complex. *Biochem Soc Trans* 40, 896-901 (2012).
27. Dolken, L. et al. High-resolution gene expression profiling for simultaneous kinetic parameter analysis of RNA synthesis and decay. *RNA* 14, 1959-72 (2008).
28. Selbach, M. et al. Widespread changes in protein synthesis induced by microRNAs. *Nature* 455, 58-63 (2008).
29. Elkon, R., Linhart, C., Sharan, R., Shamir, R. & Shiloh, Y. Genome-wide in silico identification of transcriptional regulators controlling the cell cycle in human cells. *Genome Res* 13, 773-80 (2003).
30. Corish, P. & Tyler-Smith, C. Attenuation of green fluorescent protein half-life in mammalian cells. *Protein Eng* 12, 1035-40 (1999).
31. Arlt, A. & Schafer, H. Role of the immediate early response 3 (IER3) gene in cellular stress response, inflammation and tumorigenesis. *Eur J Cell Biol* 90, 545-52 (2011).
32. Renner, F. & Schmitz, M. L. Autoregulatory feedback loops terminating the NF-kappaB response. *Trends Biochem Sci* 34, 128-35 (2009).
33. Napetschnig, J. & Wu, H. Molecular basis of NF-kappaB signaling. *Annu Rev Biophys* 42, 443-68 (2013).
34. Huang, T. T., Wuerzberger-Davis, S. M., Wu, Z. H. & Miyamoto, S. Sequential modification of NEMO/IKK-gamma by SUMO-1 and ubiquitin mediates NF-kappaB activation by genotoxic stress. *Cell* 115, 565-76 (2003).
35. Grimley, R. et al. Over expression of wild type or a catalytically dead mutant of Sirtuin 6 does not influence NFkappaB responses. *PLoS One* 7, e39847 (2012).
36. Hayden, M. S. & Ghosh, S. NF-kappaB, the first quarter-century: remarkable progress and outstanding questions. *Genes Dev* 26, 203-34 (2012).
37. Hinz, M. & Scheidereit, C. The IkappaB kinase complex in NF-kappaB regulation and beyond. *EMBO Rep* 15, 46-61 (2014).
38. Bertossi, A. et al. Loss of Roquin induces early death and immune deregulation but not autoimmunity. *J Exp Med* 208, 1749-56 (2011).
39. Walle, L. V. et al. Negative regulation of the NLRP3 inflammasome by A20 protects against arthritis. *Nature* (2014).
40. Baltz, A. G. et al. The mRNA-bound proteome and its global occupancy profile on protein-coding transcripts. *Mol Cell* 46, 674-90 (2012).
41. Schwanhausser, B., Gossen, M., Dittmar, G. & Selbach, M. Global analysis of cellular protein translation by pulsed SILAC. *Proteomics* 9, 205-9 (2009).
42. Huang da, W., Sherman, B. T. & Lempicki, R. A. Systematic and integrative analysis of large gene lists using DAVID bioinformatics resources. *Nat Protoc* 4, 44-57 (2009).

43. Huang da, W., Sherman, B. T. & Lempicki, R. A. Bioinformatics enrichment tools: paths toward the comprehensive functional analysis of large gene lists. *Nucleic Acids Res* 37, 1-13 (2009).
44. Grillo, G. et al. UTRdb and UTRsite (RELEASE 2010): a collection of sequences and regulatory motifs of the untranslated regions of eukaryotic mRNAs. *Nucleic Acids Res* 38, D75-80 (2010).
45. Hofacker, I. L. RNA secondary structure analysis using the Vienna RNA package. Curr Protoc Bioinformatics Chapter 12, Unit 12 2 (2004).
46. Rappsilber, J., Ishihama, Y. & Mann, M. Stop and go extraction tips for matrix-assisted laser desorption/ionization, nanoelectrospray, and LC/MS sample pretreatment in proteomics. *Anal Chem* 75, 663-70 (2003).
47. Cox, J. et al. Andromeda: a peptide search engine integrated into the MaxQuant environment. *J Proteome Res* 10, 1794-805 (2011).
48. Scheich, C., Kummel, D., Soumailakakis, D., Heinemann, U. & Bussow, K. Vectors for co-expression of an unrestricted number of proteins. *Nucleic Acids Res* 35, e43 (2007).
49. Ryder, S. P., Recht, M. I. & Williamson, J. R. Quantitative analysis of protein-RNA interactions by gel mobility shift. *Methods Mol Biol* 488, 99-115 (2008).
50. Hinz, M. et al. A cytoplasmic ATM-TRAF6-cIAP1 module links nuclear DNA damage signaling to ubiquitin-mediated NF-kappaB activation. *Mol Cell* 40, 63-74 (2010).
51. Gautier, L., Cope, L., Bolstad, B. M. & Irizarry, R. A. affy—analysis of Affymetrix GeneChip data at the probe level. Bioinformatics 20, 307-15 (2004).
52. Raue, A. et al. Lessons learned from quantitative dynamical modeling in systems biology. *PLoS One* 8, e74335 (2013).
53. Zuker, M. Mfold web server for nucleic acid folding and hybridization prediction. *Nucleic Acids Res* 31, 3406-15 (2003).
54. Wiese, K. C., Glen, E. & Vasudevan, A. jViz.Rna—a java tool for RNA secondary structure visualization. *NanoBioscience, IEEE Transactions on* 4, 212-218 (2005).

---

The invention claimed is:

1. An antisense oligonucleotide of 15 to 50 nucleobases in length, in single stranded form, comprising a sequence that specifically hybridizes/binds to the 3' untranslated region (3' UTR) of a TNF Alpha Induced Protein 3 (TNFAIP3) (A20) transcript according to SEQ ID No. 3, wherein said oligonucleotide comprises an at least 12-nucleobase portion with 100% sequence identity to a portion of SEQ ID NO: 3, and comprises at least one structural modification that provides improved stability and/or half-life of said oligonucleotide post-administration in a cell and/or organism compared to a structurally unmodified oligonucleotide of the same sequence, wherein the structural modification occurs in the backbone, one or more linkages, nucleobase(s) and/or sugar structure(s) of the oligonucleotide.

2. The antisense oligonucleotide according to claim 1, wherein said oligonucleotide specifically hybridizes with the RC3H1 binding site of the 3' UTR of a TNFAIP3 (A20) transcript according to SEQ ID No. 3 and comprises an at least 15-nucleobase portion with 100% sequence identity to a portion of SEQ ID NO: 3.

3. The antisense oligonucleotide according to claim 1, wherein said oligonucleotide specifically hybridizes with an at least 8-nucleobase portion of the RC3H1 binding site of the 3' UTR of a TNFAIP3 (A20) transcript according to SEQ ID No. 5.

4. The antisense oligonucleotide according to claim 1, wherein said oligonucleotide consists of a sequence of SEQ ID No. 6, SEQ ID No. 5 or SEQ ID No. 3 or complement, RNA, DNA or LNA counterpart thereof.

5. The antisense oligonucleotide according to claim 1, wherein said oligonucleotide comprises a modified internucleoside linkage.

6. The antisense oligonucleotide according to claim 5, wherein the modified internucleoside linkage is a phosphorothioate linkage.

7. The antisense oligonucleotide according to claim 1, wherein said oligonucleotide comprises at least one modified sugar moiety.

8. The antisense oligonucleotide according to claim 7, wherein the one modified sugar moiety is a 2'-O-methoxyethyl (2'-MOE) sugar moiety or a bicyclic sugar moiety.

9. The antisense oligonucleotide of claim 1 comprising at least one modified sugar moiety, wherein the modified sugar moiety is a bicyclic sugar moiety that has a $(\text{-CH2-})_n$ group forming a bridge between the 2' oxygen and the 4' carbon atoms of the sugar ring, wherein n is 1 or 2.

10. The antisense oligonucleotide according to claim 1, wherein, upon binding of said oligonucleotide to its target, said oligonucleotide:
   inhibits or disrupts the binding of RC3H1 protein to the 3' UTR of the TNFAIP3 (A20) transcript,
   increases the expression, amount of and/or activity of TNFAIP3 (A20), and/or increases IκB kinase activity.

11. A pharmaceutical composition comprising the antisense oligonucleotide of claim 1 or a pharmaceutically acceptable salt thereof and a pharmaceutically acceptable carrier.

* * * * *

SEQUENCE LISTING

<160> NUMBER OF SEQ ID NOS: 77

<210> SEQ ID NO 1
<211> LENGTH: 2010
<212> TYPE: RNA
<213> ORGANISM: Homo sapiens

<400> SEQUENCE: 1

| | | | | | |
|---|---|---|---|---|---|
| ccggaaacag | gugggucacc | uccugcaaga | aguggggccu | cgagcuguca | gucaucaugg | 60 |
| ugcuauccuc | ugaaccccuc | agcugccacu | gcaacagugg | gcuuaagggu | gucugagcag | 120 |
| gagaggaaag | auaagcucuu | cguggugccc | acgaugcuca | gguuugguaa | cccgggagug | 180 |
| uucccaggug | gccuuagaaa | gcaaagcuug | uaacuggcaa | gggaugaugu | cagauucagc | 240 |
| ccaagguucc | uccucuccua | ccaagcagga | ggccaggaac | uucuuuggac | uuggaaggug | 300 |
| ugcggggacu | ggccgaggcc | ccugcacccu | gcgcaucagg | acugcuucau | cgucuuggcu | 360 |
| gagaaaggga | aaagacacac | aagucgcgug | gguuggagaa | gccagagcca | uuccaccucc | 420 |
| ccucccccag | caucucucag | agaugugaag | ccagauccuc | auggcagcga | ggcccucugc | 480 |
| aagaagcuca | aggaagcuca | gggaaaaugg | acguauucag | agaguguuug | uaguucaugg | 540 |
| uuuuucccua | ccugcccggu | uccuuuccug | aggaccggc | agaaaugcag | aaccauccau | 600 |
| ggacugugau | ucugaggcug | cugagacuga | acauguucac | auugacagaa | aaacaagcug | 660 |
| cucuuuauaa | uaugcaccuu | uuaaaaaauu | agaauauuuu | acugggaaga | cguguaacuc | 720 |
| uuuggguuau | uacugucuuu | acuucaaag | aaguuagcuu | gaacugagga | guaaaagugu | 780 |
| guacauauau | aauauacccu | uacauuaugu | augagggauu | uuuuuaaauu | auauugaaau | 840 |
| gcugcccuag | aaguacaaua | ggaaggcuaa | auaauaauaa | ccuguuuucu | gguuguuguu | 900 |
| ggggcaugag | cuuguguaua | cacugcuugc | auaaacucaa | ccagcugccu | uuuuaaggg | 960 |
| agcucuaguc | cuuuuugugu | aauucacuuu | auuuauuuua | uuacaaacuu | caagauuauu | 1020 |
| uaagugaaga | uauuucuuca | gcucugggga | aaaugccaca | guguucuccu | gagagaacau | 1080 |
| ccuugcuuug | agucaggcug | uggcaaguu | ccugaccaca | gggaguaaau | uggccucuuu | 1140 |
| gauacacuuu | ugcuugccuc | cccaggaaag | aaggaauugc | auccaaggua | uacauacaua | 1200 |
| uucaucgaug | uuucgugcuu | cuccuuauga | aacuccagcu | auguaauaaa | aaacuauacu | 1260 |

```
cuguguucug uuaaugccuc ugagugaccu accuccuugg agaugagaua ggaaggagc     1320 agggaugaga cuggcaaugg ucacagggaa agauguggcc uuuugugaug guuuauuuu     1380 cuguuaacac uguguccugg gggggcuggg aagucccug cauccauggu uacccuggua     1440
uugggacagc aaaagccagu aaccaugagu augaggaaau cucuuucugu ugcuggcuua    1500
caguuucucu gugugcuuug ugguugcugu cauauuugcu cuagaagaaa aaaaaaaag     1560 gaggggaaau gcauuuccc cagagauaaa ggcugccauu uggggcucu guacuuaugg      1620 ccugaaaaua uuugugaucc auaacucuac acagccuuua ucauacuau uaggcacacu     1680 uuccccuuag agcccccuaa guuuuuccca gacgaaucuu uauaauuucu uuccaaagau    1740
accaaauaaa cuucagugcu ucaucuaau ucucuuaaag uugauaucuu aauauuugu      1800 guugaucauu auuccauuc uuaaugaa aaaaaguaau uauuuauacu uauuauaaaa       1860
aguauuugaa auuugcacau uuaauugcc cuaauagaaa gccaccuauu cuuguugga     1920 uuucucaag uuuuucuaaa uaaaugaac uuuucacaag agucaacauu aaaaaauaaa     1980
uuauuuaaga acagaaaaaa aaaaaaaaaaa                                    2010
```

<210> SEQ ID NO 2
<211> LENGTH: 59
<212> TYPE: RNA
<213> ORGANISM: Homo sapiens

<400> SEQUENCE: 2

```
uacauauaua auauacccuu acauuaugua ugagggauuu uuuuaaauua uauugaaau     59
```

<210> SEQ ID NO 3
<211> LENGTH: 37
<212> TYPE: RNA
<213> ORGANISM: Homo sapiens

<400> SEQUENCE: 3

```
auauauaaua uacccuuaca uuauguauga gggauuu                             37
```

<210> SEQ ID NO 4
<211> LENGTH: 159
<212> TYPE: RNA
<213> ORGANISM: Homo sapiens

<400> SEQUENCE: 4

```
acugucuuua cuucuaaaga aguuagcuug aacugaggag uaaagugug uacauauaua     60 auauacccuu acauuaugua ugagggauuu uuuuaaauua uauugaaaug cugcccuaga    120
aguacaauag gaaggcuaaa uaauaauaac cuguuuucu                           159
```

<210> SEQ ID NO 5
<211> LENGTH: 23
<212> TYPE: RNA
<213> ORGANISM: Homo sapiens

<400> SEQUENCE: 5

```
acccuuacau uauguaugag gga                                            23
```

<210> SEQ ID NO 6
<211> LENGTH: 18
<212> TYPE: DNA
<213> ORGANISM: Homo sapiens

<400> SEQUENCE: 6

```
aaatccctca tacataat                                                  18
```

```
<210> SEQ ID NO 7
<211> LENGTH: 43
<212> TYPE: DNA
<213> ORGANISM: Homo sapiens

<400> SEQUENCE: 7
tgtacatata taatataccc ttacattatg tatgagggat ttt          43

<210> SEQ ID NO 8
<211> LENGTH: 21
<212> TYPE: RNA
<213> ORGANISM: Homo sapiens

<400> SEQUENCE: 8
cccuuacauu auguaugagg g                                  21

<210> SEQ ID NO 9
<211> LENGTH: 35
<212> TYPE: DNA
<213> ORGANISM: Homo sapiens

<400> SEQUENCE: 9
catatataat ataccettac attatgtatg aggga                   35

<210> SEQ ID NO 10
<211> LENGTH: 35
<212> TYPE: DNA
<213> ORGANISM: Homo sapiens

<400> SEQUENCE: 10
catatataat ataccettac ataatctatc agcga                   35

<210> SEQ ID NO 11
<211> LENGTH: 35
<212> TYPE: DNA
<213> ORGANISM: Homo sapiens

<400> SEQUENCE: 11
caaaaaaaaa aaaccettac ataatctatc agcga                   35

<210> SEQ ID NO 12
<211> LENGTH: 35
<212> TYPE: DNA
<213> ORGANISM: Homo sapiens

<400> SEQUENCE: 12
caaaaaaaaa aaaccettac attatgtatg aggga                   35

<210> SEQ ID NO 13
<211> LENGTH: 35
<212> TYPE: DNA
<213> ORGANISM: Homo sapiens

<400> SEQUENCE: 13
catgtacgat ctgcccttac attatgtatg aggga                   35

<210> SEQ ID NO 14
<211> LENGTH: 35
<212> TYPE: DNA
<213> ORGANISM: Homo sapiens

<400> SEQUENCE: 14
catgtacgat ctgcccttac ataatctatc agcga                   35
```

```
<210> SEQ ID NO 15
<211> LENGTH: 35
<212> TYPE: DNA
<213> ORGANISM: Homo sapiens

<400> SEQUENCE: 15
catgtacgat ctgcccttac aaaatctatg aggga                              35

<210> SEQ ID NO 16
<211> LENGTH: 7
<212> TYPE: RNA
<213> ORGANISM: Homo sapiens

<400> SEQUENCE: 16 ucyryga                                                              7

<210> SEQ ID NO 17
<211> LENGTH: 19
<212> TYPE: RNA
<213> ORGANISM: Homo sapiens

<400> SEQUENCE: 17
gcugggaaau acaaaggaa                                                19

<210> SEQ ID NO 18
<211> LENGTH: 19
<212> TYPE: RNA
<213> ORGANISM: Homo sapiens

<400> SEQUENCE: 18
ccaagaaaug uguagaaga                                                19

<210> SEQ ID NO 19
<211> LENGTH: 20
<212> TYPE: DNA
<213> ORGANISM: Homo sapiens

<400> SEQUENCE: 19
tggacaacca gaaccacaaa                                               20

<210> SEQ ID NO 20
<211> LENGTH: 22
<212> TYPE: DNA
<213> ORGANISM: Homo sapiens

<400> SEQUENCE: 20
gctgatccat ttggtacatc ac                                            22

<210> SEQ ID NO 21
<211> LENGTH: 21
<212> TYPE: DNA
<213> ORGANISM: Homo sapiens

<400> SEQUENCE: 21
tgcacactgt gtttcatcga g                                             21

<210> SEQ ID NO 22
<211> LENGTH: 20
<212> TYPE: DNA
<213> ORGANISM: Homo sapiens

<400> SEQUENCE: 22
acgctgtggg actgactttc                                               20
```

```
<210> SEQ ID NO 23
<211> LENGTH: 18
<212> TYPE: DNA
<213> ORGANISM: Homo sapiens

<400> SEQUENCE: 23
ggagagcacg ccatgaag                                                 18

<210> SEQ ID NO 24
<211> LENGTH: 20
<212> TYPE: DNA
<213> ORGANISM: Homo sapiens

<400> SEQUENCE: 24
aagattcgca tgcggtagag                                               20

<210> SEQ ID NO 25
<211> LENGTH: 19
<212> TYPE: DNA
<213> ORGANISM: Homo sapiens

<400> SEQUENCE: 25
agccacatcg ctcagacac                                                19

<210> SEQ ID NO 26
<211> LENGTH: 19
<212> TYPE: DNA
<213> ORGANISM: Homo sapiens

<400> SEQUENCE: 26
gcccaatacg accaaatcc                                                19

<210> SEQ ID NO 27
<211> LENGTH: 21
<212> TYPE: DNA
<213> ORGANISM: Homo sapiens

<400> SEQUENCE: 27
gagtcagagt tcacggagtt c                                             21

<210> SEQ ID NO 28
<211> LENGTH: 21
<212> TYPE: DNA
<213> ORGANISM: Homo sapiens

<400> SEQUENCE: 28
catgttcttt cagccccttt g                                             21

<210> SEQ ID NO 29
<211> LENGTH: 47
<212> TYPE: DNA
<213> ORGANISM: Homo sapiens

<400> SEQUENCE: 29
ggcctgtaca tatataatat acccttacat tatgtatgag ggattttt                47

<210> SEQ ID NO 30
<211> LENGTH: 47
<212> TYPE: DNA
<213> ORGANISM: Homo sapiens

<400> SEQUENCE: 30
tcgaaaaatc cctcatacat aatgtaaggg tatattatat atgtaca                 47
```

```
<210> SEQ ID NO 31
<211> LENGTH: 47
<212> TYPE: DNA
<213> ORGANISM: Homo sapiens

<400> SEQUENCE: 31
ggcctgtaca tatataatat acccttacat aatctatcag cgatttt         47

<210> SEQ ID NO 32
<211> LENGTH: 47
<212> TYPE: DNA
<213> ORGANISM: Homo sapiens

<400> SEQUENCE: 32
tcgaaaaatc gctgatagat tatgtaaggg tatattatat atgtaca         47

<210> SEQ ID NO 33
<211> LENGTH: 47
<212> TYPE: DNA
<213> ORGANISM: Homo sapiens

<400> SEQUENCE: 33
ggcctgtaca aaaaaaaaaa acccttacat aatctatcag cgatttt         47

<210> SEQ ID NO 34
<211> LENGTH: 47
<212> TYPE: DNA
<213> ORGANISM: Homo sapiens

<400> SEQUENCE: 34
tcgaaaaatc gctgatagat tatgtaaggg tttttttttt ttgtaca         47

<210> SEQ ID NO 35
<211> LENGTH: 47
<212> TYPE: DNA
<213> ORGANISM: Homo sapiens

<400> SEQUENCE: 35
ggcctgtaca aaaaaaaaaa acccttacat tatgtatgag ggatttt         47

<210> SEQ ID NO 36
<211> LENGTH: 47
<212> TYPE: DNA
<213> ORGANISM: Homo sapiens

<400> SEQUENCE: 36
tcgaaaaatc cctcatacat aatgtaaggg tttttttttt ttgtaca         47

<210> SEQ ID NO 37
<211> LENGTH: 47
<212> TYPE: DNA
<213> ORGANISM: Homo sapiens

<400> SEQUENCE: 37
ggcctgtaca tgtacgatct gcccttacat tatgtatgag ggatttt         47

<210> SEQ ID NO 38
<211> LENGTH: 47
<212> TYPE: DNA
<213> ORGANISM: Homo sapiens

<400> SEQUENCE: 38
tcgaaaaatc cctcatacat aatgtaaggg cagatcgtac atgtaca         47
```

```
<210> SEQ ID NO 39
<211> LENGTH: 47
<212> TYPE: DNA
<213> ORGANISM: Homo sapiens

<400> SEQUENCE: 39
ggcctgtaca tgtacgatct gcccttacat aatctatcag cgattttt        47

<210> SEQ ID NO 40
<211> LENGTH: 47
<212> TYPE: DNA
<213> ORGANISM: Homo sapiens

<400> SEQUENCE: 40
tcgaaaaatc gctgatagat tatgtaaggg cagatcgtac atgtaca         47

<210> SEQ ID NO 41
<211> LENGTH: 47
<212> TYPE: DNA
<213> ORGANISM: Homo sapiens

<400> SEQUENCE: 41
ggcctgtaca tgtacgatct gcccttacaa atctatgag ggattttt         47

<210> SEQ ID NO 42
<211> LENGTH: 47
<212> TYPE: DNA
<213> ORGANISM: Homo sapiens

<400> SEQUENCE: 42
tcgaaaaatc cctcatagat tttgtaaggg cagatcgtac atgtaca         47

<210> SEQ ID NO 43
<211> LENGTH: 13
<212> TYPE: RNA
<213> ORGANISM: Homo sapiens

<400> SEQUENCE: 43
auuucuguga aau                                              13

<210> SEQ ID NO 44
<211> LENGTH: 21
<212> TYPE: DNA
<213> ORGANISM: Homo sapiens

<400> SEQUENCE: 44
tcgtatgccg tcttctgctt g                                     21

<210> SEQ ID NO 45
<211> LENGTH: 28
<212> TYPE: DNA
<213> ORGANISM: Homo sapiens

<400> SEQUENCE: 45
tctcgtatcg tatgccgtct tctgcttg                              28

<210> SEQ ID NO 46
<211> LENGTH: 28
<212> TYPE: DNA
<213> ORGANISM: Homo sapiens

<400> SEQUENCE: 46
tctctgctcg tatgccgtct tctgcttg                              28
```

```
<210> SEQ ID NO 47
<211> LENGTH: 52
<212> TYPE: RNA
<213> ORGANISM: Homo sapiens

<400> SEQUENCE: 47
rgrururcra rgrargruru rcrurarcra rgrurcrcrg rarcrgraru rc            52

<210> SEQ ID NO 48
<211> LENGTH: 7
<212> TYPE: RNA
<213> ORGANISM: Homo sapiens

<400> SEQUENCE: 48 uuuuuaa                                                              7

<210> SEQ ID NO 49
<211> LENGTH: 7
<212> TYPE: RNA
<213> ORGANISM: Homo sapiens

<400> SEQUENCE: 49 uuuuaaa                                                              7

<210> SEQ ID NO 50
<211> LENGTH: 7
<212> TYPE: RNA
<213> ORGANISM: Homo sapiens

<400> SEQUENCE: 50 uuuauuu                                                              7

<210> SEQ ID NO 51
<211> LENGTH: 7
<212> TYPE: RNA
<213> ORGANISM: Homo sapiens

<400> SEQUENCE: 51 uuauuuu                                                              7

<210> SEQ ID NO 52
<211> LENGTH: 7
<212> TYPE: RNA
<213> ORGANISM: Homo sapiens

<400> SEQUENCE: 52 uuuucuu                                                              7

<210> SEQ ID NO 53
<211> LENGTH: 7
<212> TYPE: RNA
<213> ORGANISM: Homo sapiens

<400> SEQUENCE: 53 uauuuau                                                              7

<210> SEQ ID NO 54
<211> LENGTH: 7
<212> TYPE: RNA
<213> ORGANISM: Homo sapiens

<400> SEQUENCE: 54 cugaacc                                                              7
```

```
<210> SEQ ID NO 55
<211> LENGTH: 7
<212> TYPE: RNA
<213> ORGANISM: Homo sapiens

<400> SEQUENCE: 55 gguauau                                                                    7

<210> SEQ ID NO 56
<211> LENGTH: 7
<212> TYPE: RNA
<213> ORGANISM: Homo sapiens

<400> SEQUENCE: 56 uuuguu                                                                     7

<210> SEQ ID NO 57
<211> LENGTH: 7
<212> TYPE: RNA
<213> ORGANISM: Homo sapiens

<400> SEQUENCE: 57 uuuaaaa                                                                    7

<210> SEQ ID NO 58
<211> LENGTH: 7
<212> TYPE: RNA
<213> ORGANISM: Homo sapiens

<400> SEQUENCE: 58 uuuuuua                                                                    7

<210> SEQ ID NO 59
<211> LENGTH: 7
<212> TYPE: RNA
<213> ORGANISM: Homo sapiens

<400> SEQUENCE: 59 uuuuuuu                                                                    7

<210> SEQ ID NO 60
<211> LENGTH: 7
<212> TYPE: RNA
<213> ORGANISM: Homo sapiens

<400> SEQUENCE: 60 auuuuuu                                                                    7

<210> SEQ ID NO 61
<211> LENGTH: 7
<212> TYPE: RNA
<213> ORGANISM: Homo sapiens

<400> SEQUENCE: 61 uauuuuu                                                                    7

<210> SEQ ID NO 62
<211> LENGTH: 7
<212> TYPE: RNA
<213> ORGANISM: Homo sapiens

<400> SEQUENCE: 62 aaauuuu                                                                    7
```

```
<210> SEQ ID NO 63
<211> LENGTH: 7
<212> TYPE: RNA
<213> ORGANISM: Homo sapiens

<400> SEQUENCE: 63 aauuuuu                                                              7

<210> SEQ ID NO 64
<211> LENGTH: 7
<212> TYPE: RNA
<213> ORGANISM: Homo sapiens

<400> SEQUENCE: 64 uuuuauu                                                              7

<210> SEQ ID NO 65
<211> LENGTH: 7
<212> TYPE: RNA
<213> ORGANISM: Homo sapiens

<400> SEQUENCE: 65 auuuuaa                                                              7

<210> SEQ ID NO 66
<211> LENGTH: 7
<212> TYPE: RNA
<213> ORGANISM: Homo sapiens

<400> SEQUENCE: 66 auuuuau                                                              7

<210> SEQ ID NO 67
<211> LENGTH: 59
<212> TYPE: DNA
<213> ORGANISM: Homo sapiens

<400> SEQUENCE: 67
tacatatata atataccctt acattatgta tgagggattt ttttaaatta tattgaaat     59

<210> SEQ ID NO 68
<211> LENGTH: 41
<212> TYPE: RNA
<213> ORGANISM: Homo sapiens

<400> SEQUENCE: 68
acuuacuacu ugaaacuuua uuuauugcac cauguuggug u                        41

<210> SEQ ID NO 69
<211> LENGTH: 41
<212> TYPE: RNA
<213> ORGANISM: Homo sapiens

<400> SEQUENCE: 69
aacauacuaa cauuucuccu uuggaggaag uuuuaaucua c                        41

<210> SEQ ID NO 70
<211> LENGTH: 41
<212> TYPE: RNA
<213> ORGANISM: Homo sapiens

<400> SEQUENCE: 70
gaggagggag aagugggaag uagcuuggga acugguuugu c                        41
```

```
<210> SEQ ID NO 71
<211> LENGTH: 41
<212> TYPE: RNA
<213> ORGANISM: Homo sapiens

<400> SEQUENCE: 71 guaaauaag cauuuggaag ucuugggagg ccugccugcu a        41

<210> SEQ ID NO 72
<211> LENGTH: 41
<212> TYPE: RNA
<213> ORGANISM: Homo sapiens

<400> SEQUENCE: 72
ugugcaacac aggauuauuu uuaaaugauu cugaauuuga a        41

<210> SEQ ID NO 73
<211> LENGTH: 41
<212> TYPE: RNA
<213> ORGANISM: Homo sapiens

<400> SEQUENCE: 73
gguuuacuau acaucagcau uuugcugugu ugcaucuaga a        41

<210> SEQ ID NO 74
<211> LENGTH: 40
<212> TYPE: RNA
<213> ORGANISM: Homo sapiens

<400> SEQUENCE: 74
uucuagauac uuaaaaggcu uuugccuugc acaaaguaua          40

<210> SEQ ID NO 75
<211> LENGTH: 41
<212> TYPE: RNA
<213> ORGANISM: Homo sapiens

<400> SEQUENCE: 75
uauacacaua cuuacauacu uauaugggua ucuguauaga u        41

<210> SEQ ID NO 76
<211> LENGTH: 41
<212> TYPE: RNA
<213> ORGANISM: Homo sapiens

<400> SEQUENCE: 76
auauauaaua uacccuuaca uuauguauga gggauuuuuu u        41

<210> SEQ ID NO 77
<211> LENGTH: 99
<212> TYPE: RNA
<213> ORGANISM: Homo sapiens

<400> SEQUENCE: 77
aacugaggag uaaagugug uacauauaua auauacccuu acauuaugua ugagggauuu   60
uuuuaaauua uauugaaaug cugcccuaga aguacaaua                        99
```